United States Patent
El-Araby et al.

(10) Patent No.: US 11,155,528 B2
(45) Date of Patent: *Oct. 26, 2021

(54) BIS-PROPENAMIDE COMPOUNDS AND METHODS OF TREATING CANCER

(71) Applicant: King Abdulaziz University, Jeddah (SA)

(72) Inventors: Moustafa E. El-Araby, Jeddah (SA); Abdelsattar M. Omar, Jeddah (SA); Martin K. Safo, Jeddah (SA); Radwan S. Elhaggar, Jeddah (SA); Tamer M. Abdelghany, Jeddah (SA); Mostafa H. Ahmed, Jeddah (SA)

(73) Assignee: King Abdulaziz University, Jeddah (SA)

( * ) Notice: Subject to any disclaimer, the term of this patent is extended or adjusted under 35 U.S.C. 154(b) by 46 days.

This patent is subject to a terminal disclaimer.

(21) Appl. No.: 16/663,861

(22) Filed: Oct. 25, 2019

(65) Prior Publication Data
US 2021/0122721 A1    Apr. 29, 2021

(51) Int. Cl.

| | |
|---|---|
| *C07D 295/108* | (2006.01) |
| *C07D 307/52* | (2006.01) |
| *C07D 209/14* | (2006.01) |
| *C07D 213/75* | (2006.01) |
| *C07D 295/15* | (2006.01) |
| *C07D 207/06* | (2006.01) |
| *C07D 233/40* | (2006.01) |
| *C07D 333/24* | (2006.01) |
| *C07D 241/04* | (2006.01) |
| *C07D 295/13* | (2006.01) |
| *C07C 233/40* | (2006.01) |

(52) U.S. Cl.
CPC ........ *C07D 295/108* (2013.01); *C07C 233/40* (2013.01); *C07D 207/06* (2013.01); *C07D 209/14* (2013.01); *C07D 213/75* (2013.01); *C07D 241/04* (2013.01); *C07D 295/13* (2013.01); *C07D 307/52* (2013.01); *C07D 333/24* (2013.01)

(58) Field of Classification Search
CPC .............. C07D 295/108; C07D 295/13; C07D 207/06; C07D 209/14; C07D 213/75; C07D 241/04; C07D 307/52; C07D 333/24
See application file for complete search history.

(56) References Cited

U.S. PATENT DOCUMENTS

| | | | | |
|---|---|---|---|---|
| 4,310,517 A | * | 1/1982 | Etschenberg | A61P 35/00 514/21.91 |
| 10,836,736 B1 | * | 11/2020 | El-Araby | C07D 213/75 |
| 2012/0082657 A1 | | 4/2012 | Land et al. | |
| 2012/0114670 A1 | | 5/2012 | Land et al. | |

FOREIGN PATENT DOCUMENTS

| | | |
|---|---|---|
| WO | WO 2009/045443 A2 | 4/2009 |
| WO | WO 2012/100248 A1 | 7/2012 |

OTHER PUBLICATIONS

Mustafa et al., Justus Liebigs Annalen der Chemie, vol. 714, pp. 146-154, 1968.*
S-Y Ju, et al., "Identification of thiostrepton as a novel therapeutic agent that targets human colon cancer stem cells", Cell Death and Disease, vol. 6, No. 7, e108, 2015, pp. 1-11.
Yaman Musdal, et al., "FDA-approved drugs and other compounds tested as inhibitors of human glutathione transferase P1-1", Chemico-Biological Interactions, vol. 205, Issue 1, Sep. 5, 2013, pp. 53-62 (Abstract only).
Vishal M. Gohil, et al., "Nutrient-sensitized screening for drugs that shift energy metabolism from mitochondrial respiration to glycolysis", Nature Biotechnology, vol. 28, No. 3, 2010, pp. 1-9.

* cited by examiner

*Primary Examiner* — Rebecca L Anderson
(74) *Attorney, Agent, or Firm* — Oblon, McClelland, Maier & Neustadt, L.L.P.

(57) ABSTRACT

A compound of formula (I),

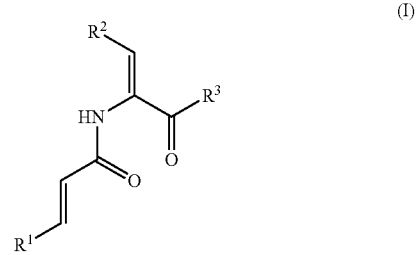

wherein $R^1$ is an optionally substituted aryl or an optionally substituted heteroaryl, $R^2$ is an optionally substituted aryl or an optionally substituted heteroaryl, and $R^3$ is an optionally substituted alkylamino, an optionally substituted cycloalkylamino, an optionally substituted arylamino, an optionally substituted heterocyclylamino, an optionally substituted heterocyclyl, and an optionally substituted dialkylamino. A pharmaceutical composition which includes the compound of formula (I) and a pharmaceutically acceptable carrier and/or excipient. A method of treating colorectal cancer in a subject, whereby a therapeutically effective amount of the compound of formula (I) is administered to the subject.

2 Claims, 9 Drawing Sheets

Bis-(propenamide) scafflod
Compounds
MOS-1501 to MOS-5112

Final Compounds ical Field

The present disclosure relates to a family of therapeutic compounds having a bis-propenamide scaffold, a pharmaceutical composition containing the compounds, and a method for treating cancer with the compounds.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Several Michael acceptors (MAs) have been developed or are currently being developed as therapeutic agents. For instance, Afatinib (FIG. 1A) a target-specific MA selectively inhibits mutated HER2 kinase, and is approved by the FDA for the treatment of non-small cell lung cancer. See Minkovsky, N.; Berezov, A., BIBW-2992, a dual receptor tyrosine kinase inhibitor for the treatment of solid tumors. *Curr Opin Investig Drugs* 2008, 9 (12), 1336-46; and Suzawa, K.; Toyooka, S.; Sakaguchi, M.; Morita, M.; Yamamoto, H.; Tomida, S.; Ohtsuka, T.; Watanabe, M.; Hashida, S.; Maki, Y.; Soh, J.; Asano, H.; Tsukuda, K.; Miyoshi, S., Antitumor effect of afatinib, as a HER2-targeted therapy, in lung cancers harboring HER2 oncogene alterations. *Cancer Sci* 2015, each incorporated herein by reference in their entirety. Other examples include ibrutinib (BTK inhibitor) and neratinib (HER-2 inhibitor) that have been developed for B-cell cancers and solid tumors, respectively. See Singh, J.; Petter, R. C.; Baillie, T. A.; Whitty, A., The resurgence of covalent drugs. *Nat Rev Drug Discov* 2011, 10 (4), 307-17; and Lanning, B. R.; Whitby, L. R.; Dix, M. M.; Douhan, J.; Gilbert, A. M.; Hett, E. C.; Johnson, T. O.; Joslyn, C.; Kath, J. C.; Niessen, S.; Roberts, L. R.; Schnute, M. E.; Wang, C.; Hulce, J. J.; Wei, B.; Whiteley, L. O.; Hayward, M. M.; Cravatt, B. F., A road map to evaluate the proteome-wide selectivity of covalent kinase inhibitors. *Nat Chem Biol* 2014, 10 (9), 760-7, each incorporated herein by reference in their entirety. Mechanistically, the MAs cause cancer cell apoptosis by increasing the oxidative stress inside these cells. The cellular prooxidant induction by MAs is attributed to ligation of SH groups of certain targets involved in regeneration of reduced glutathione (GSH). This results in accumulation of reactive oxygen species (ROS) which cause cancer cell cycle exits and apoptosis. See Wondrak, G. T., Redox-directed cancer therapeutics: molecular mechanisms and opportunities. *Antioxid Redox Signal* 2009, 11 (12), 3013-69, incorporated herein by reference in its entirety.

Acrolein (FIG. 1A) is a highly reactive and non-selective MA toxin and environmental pollutant with well-known carcinogenic activity. Interestingly, acrolein is also known to cause inhibition of the β-subunit of the proliferative anti-apoptotic protein NFκB via covalent binding with the nucleophilic Cys-61 and Arg-307 leading to cytotoxicity and cell death of cancer cells. See Chan, K.; Poon, R.; O'Brien, P. J., Application of structure-activity relationships to investigate the molecular mechanisms of hepatocyte toxicity and electrophilic reactivity of alpha,beta-unsaturated aldehydes. *J Appl Toxicol* 2008, 28 (8), 1027-39, incorporated herein by reference in its entirety. Thus despite its apparent toxic effect, acrolein like other MAs has potential as a therapeutic agent. Replacement of the aldehyde group of acrolein with an amide group (acrylamide moiety) is known to attenuate the reactivity of the MA moiety leading to less toxic compounds. See Schwobel, J. A.; Wondrousch, D.; Koleva, Y. K.; Madden, J. C.; Cronin, M. T.; Schuurmann, G., Prediction of michael-type acceptor reactivity toward glutathione. *Chem Res Toxicol* 2010, 23 (10), 1576-85, incorporated herein by reference in its entirety. Safe natural MA products that are common in domestic condiments, such as trans-cinnamaldehyde (tCA) and curcumin (FIG. 1), are known to cause cancer cell death via redox mechanisms. See Wondrak, G. T., Redox-directed cancer therapeutics: molecular mechanisms and opportunities, *Antioxid Redox Signal* 2009, 11 (12), 3013-69; Noh, J.; Kwon, B.; Han, E.; Park, M.; Yang, W.; Cho, W.; Yoo, W.; Khang, G.; Lee, D., Amplification of oxidative stress by a dual stimuli-responsive hybrid drug enhances cancer cell death. *Nature communications* 2015, 6, 6907; Lin, L. T.; Tai, C. J.; Chang, S. P.; Chen, J. L.; Wu, S. J.; Lin, C. C., Cinnamaldehyde-induced apoptosis in human hepatoma PLC/PRF/5 cells involves the mitochondrial death pathway and is sensitive to inhibition by cyclosporin A and z-VAD-fmk. *Anticancer Agents Med Chem* 2013, 13 (10), 1565-74; Wondrak, G. T.; Villeneuve, N. F.; Lamore, S. D.; Bause, A. S.; Jiang, T.; Zhang, D. D., The cinnamon-derived dietary factor cinnamic aldehyde activates the Nrf2-dependent antioxidant response in human epithelial colon cells. *Molecules* 2010, 15 (5), 3338-55; Kwon, H. K.; Hwang, J. S.; So, J. S.; Lee, C. G.; Sahoo, A.; Ryu, J. H.; Jeon, W. K.; Ko, B. S.; Im, C. R.; Lee, S. H.; Park, Z. Y.; Im, S. H., Cinnamon extract induces tumor cell death through inhibition of NFkappaB and AP. *BMC Cancer* 2010, 10, 392; Cabello, C. M.; Bair, W. B., 3rd; Lamore, S. D.; Ley, S.; Bause, A. S.; Azimian, S.; Wondrak, G. T., The cinnamon-derived Michael acceptor cinnamic aldehyde impairs melanoma cell proliferation, invasiveness, and tumor growth. *Free Radic Biol Med* 2009, 46 (2), 220-31; Ka, H.; Park, H. J.; Jung, H. J.; Choi, J. W.; Cho, K. S.; Ha, J.; Lee, K. T., Cinnamaldehyde induces apoptosis by ROS-mediated mitochondrial permeability transition in human promyelocytic leukemia HL-60 cells. *Cancer Lett* 2003, 196 (2), 143-52; and Aggarwal, B. B.; Surh, Y.-J.; Shishodia, S., The molecular targets and therapeutic uses of curcumin in health and disease. Springer Science & Business Media: 2007; Vol. 595, each incorporated herein by reference in their entirety. However, there still exists a need for new MA anticancer agents with a large therapeutic window, that is, that exhibit potent anti-proliferative effects against cancerous cells without significantly effecting normal cells.

In view of the forgoing, one objective of the present disclosure is to provide safe therapeutic compounds with antiproliferative activities based on a bis-propenamide scaffold having a cinnamoyl-type appendage, a pharmaceutical composition containing the compounds, and a method for treating cancer with the compounds.

BRIEF SUMMARY OF THE INVENTION

Accordingly, it is one object of the present invention to provide compounds with bis(propenamide) scaffolds based on trans-cinnamaldehyde (3-phenylpropenal or tCA) and curcumin structural features, which are non-toxic and have excellent pharmacologic properties.

It is another object of the present invention to provide pharmaceutical compositions containing the compounds.

It is yet another object of the present invention to provide methods for treating cancer with the compounds.

Thus, the present invention provides:

A compound of formula (I),

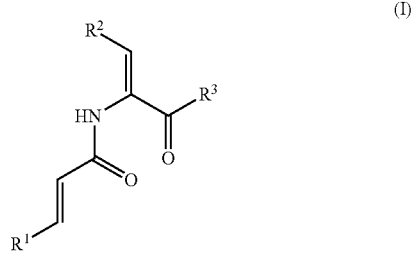

or a pharmaceutically acceptable salt, solvate, tautomer, or stereoisomer thereof, wherein:

$R^1$ is an optionally substituted aryl or an optionally substituted heteroaryl;

$R^2$ is an optionally substituted aryl or an optionally substituted heteroaryl; and $R^3$ is an optionally substituted alkylamino, an optionally substituted cycloalkylamino, an optionally substituted arylamino, an optionally substituted heterocyclylamino, an optionally substituted heterocyclyl, and an optionally substituted dialkylamino.

In some embodiments, $R^1$ is an optionally substituted phenyl or an optionally substituted thienyl.

In some embodiments, $R^1$ is phenyl, a 4-halophenyl, a 4-alkoxyphenyl, a 4-alkylphenyl, and a thienyl.

In some embodiments, $R^1$ is selected from the group consisting of phenyl, 4-chlorophenyl, 4-methoxyphenyl, 4-methylphenyl, and 2-thienyl.

In some embodiments, $R^1$ is phenyl or 2-thienyl.

In some embodiments, $R^2$ is an optionally substituted phenyl, an optionally substituted indolyl, or an optionally substituted pyridyl.

In some embodiments, $R^2$ is phenyl, a 4-halophenyl, a 4-dialkylaminophenyl, 3-alkoxy-4-hydroxyphenyl, a 4-nitrophenyl, a 1H-indolyl, and a pyridyl.

In some embodiments, $R^2$ is selected from the group consisting of phenyl, 4-fluorophenyl, 4-dimethylaminophenyl, 3-methoxy-4-hydroxyphenyl, 4-nitrophenyl, 1H-indol-3-yl, and 3-pyridyl.

In some embodiments, $R^2$ is phenyl or 1H-indol-3-yl.

In some embodiments, $R^3$ is an optionally substituted $C_1$ to $C_4$ alkylamino, an optionally substituted $C_5$ to $C_{10}$ cycloalkylamino, an optionally substituted phenylamino, an optionally substituted pyridylamino, an optionally substituted N-piperazinylamino, an optionally substituted morpholinyl, an optionally substituted pyrrolidinyl, and an optionally substituted di-($C_1$ to $C_3$ alkyl)amino.

In some embodiments, $R^3$ is selected from the group consisting of cyclopentylamino, 1-adamantylamino, 3-pyridylamino, 4-methyl-1-piperazinylamino, ethylamino, n-propylamino, n-butylamino, sec-butylamino, 3-cyanophenylamino, 4-fluorophenylamino, furfurylamino, 2-morpholinoethylamino, 2-hydroxyethylamino, 4-morpholinyl, 1-pyrrolidinyl, and methylethylamino.

In some embodiments, $R^3$ is a $C_3$ to $C_4$ alkylamino, a $C_5$ to $C_{10}$ cycloalkylamino, or a di-($C_1$ to $C_3$ alkyl)amino In some embodiments, $R^3$ is n-propylamino.

The present invention also provides a pharmaceutical composition, which includes the compound of formula (I) and a pharmaceutically acceptable carrier and/or excipient.

In some embodiments, the pharmaceutical composition is in the form of an aqueous suspension, and wherein the pharmaceutically acceptable carrier and/or excipient is a non-ionic surfactant in water.

In some embodiments, the pharmaceutical composition contains 5 to 15 wt. % of the compound of formula (I), relative to a total weight of the pharmaceutical composition.

The present invention also provides a method for treating colorectal cancer in a subject, by administering to the subject a therapeutically effective amount of the compound of formula (I).

In some embodiments, the therapeutically effective amount of the compound of formula (I) is from 0.1 to 2,000 mg/kg of the compound of formula (I) per body weight of the subject.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1A:
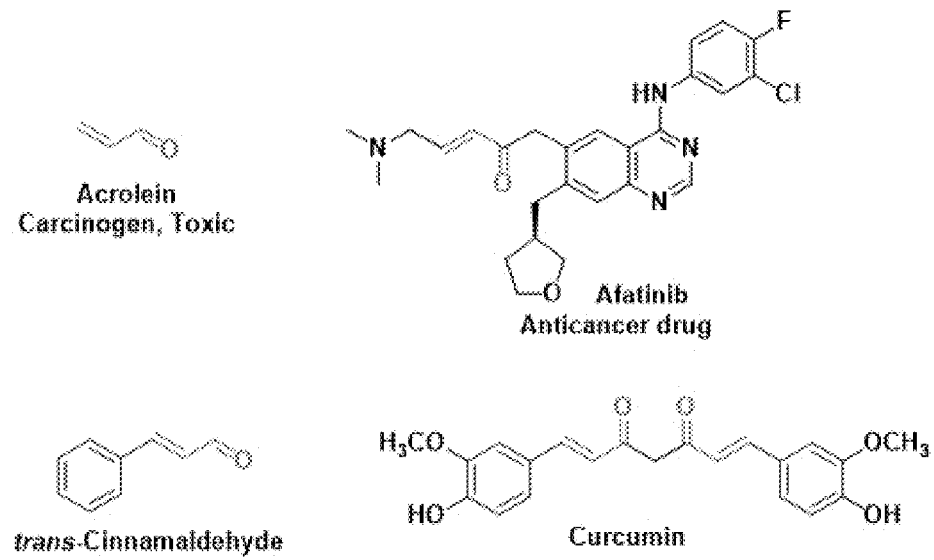
FIG. 1A illustrates Michael acceptor (MA)-based drugs, flavors and poisons.
Figure 1B:
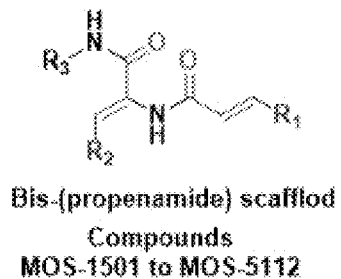
FIG. 1B illustrates the bis-propenamide scaffold of the compounds of the present disclosure.

Embodiments of the present disclosure will now be described more fully hereinafter with reference to the accompanying drawings, in which some, but not all embodiments of the disclosure are shown.

Definitions

As used herein, the terms "compound", "complex", and "product" are used interchangeably, and are intended to refer to a chemical entity, whether in the solid, liquid or gaseous phase, and whether in a crude mixture or purified and isolated.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the disclosure. Many geometric isomers of C=C double bonds, C=N double bonds, ring systems, and the like can also be present in the compounds, and all such stable isomers are contemplated in the present disclosure. Cis- and trans-(or E- and Z-) geometric isomers of the compounds of the present disclosure are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present disclosure and intermediates made therein are considered to be part of the present disclosure. When enantiomeric or diastereomeric products are prepared, they may be separated by conventional methods, for example, by chromatography, fractional crystallization, or through the use of a chiral agent. Depending on the process conditions the end products of the present disclosure are obtained either in free (neutral) or salt form. Both the free form and the salts of these end products are within the scope of the disclosure. If so desired, one form of a compound may be converted into another form. A free base or acid may be converted into a salt; a salt may be converted into the free compound or another salt; a mixture of isomeric compounds of the present disclosure may be separated into the individual isomers. Compounds of the present disclosure, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the disclosure. Further, a given chemical formula or name shall encompass all conformers, rotamers, or conformational isomers thereof where such isomers exist. Different conformations can have different energies, can usually interconvert, and are very rarely isolatable. There are some molecules that can be isolated in several conformations. For example, atropisomers are isomers resulting from hindered rotation about single bonds where the steric strain barrier to rotation is high enough to allow for the isolation of the conformers. It should be understood that all conformers, rotamers, or conformational isomer forms, insofar as they may exist, are included within the present disclosure.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, isobutanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g., polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those of ordinary skill in the art.

As used herein, "pharmaceutically acceptable salt" refers to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like. The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 18th Edition, Mack Publishing Company, Easton, Pa. (1990), the disclosure of which is hereby incorporated by reference.

As used herein, the term "alkyl" unless otherwise specified refers to both branched and straight chain aliphatic (non-aromatic) hydrocarbons which may be primary, secondary, and/or tertiary hydrocarbons typically having 1 to 32 carbon atoms (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, etc.) and specifically includes, but is not limited to, saturated alkyl groups such as methyl, ethyl, propyl, isopropyl, butyl, isobutyl, t-butyl, pentyl, isopentyl, neopentyl, hexyl, isohexyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, tetradecyl, pentadecyl, hexadecyl, heptadecyl, octadecyl, nonadecyl, eicosyl, guerbet-type alkyl groups (e.g., 2-methylpentyl, 2-ethylhexyl, 2-proylheptyl, 2-butyloctyl, 2-pentylnonyl, 2-hexyldecyl, 2-heptylundecyl, 2-octyldodecyl, 2-nonyltridecyl, 2-decyltetradecyl, and 2-undecylpentadecyl), as well as unsaturated alkenyl and alkynyl variants such as vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, oleyl, linoleyl, and the like.

The term "cycloalkyl" refers to cyclized alkyl groups. Exemplary cycloalkyl groups include, but are not limited to, saturated cycloalkyl groups such as cyclopropyl, cyclobutyl, cyclopentyl, cyclohexyl, norbornyl, and adamantyl, branched cycloalkyl groups such as 1-methylcyclopropyl and 2-methylcyclopropyl, and cycloalkenyl groups such as cyclobutenyl, cyclopentenyl, and cyclohexenyl.

The term "aryl" means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, anthracenyl, indanyl, 1-naphthyl, 2-naphthyl, and tetrahydronaphthyl. The fused aryls may be connected to another group either at a suitable position on the cycloalkyl/cycloalkenyl ring or the aromatic ring.

The term "arylalkyl", as used herein, refers to a straight or branched chain alkyl moiety (as defined above) that is substituted by an aryl group (as defined above), examples of which include, but are not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

The term "alkoxy" refers to an —O-alkyl group. Example alkoxy groups include, but are not limited to, methoxy, ethoxy, propoxy (e.g., n-propoxy and isopropoxy), and t-butoxy.

As used herein, the term "heterocycle" or "heterocyclyl" is intended to mean a stable 3-, 4-, 5-, 6-, or 7-membered monocyclic, 7-, 8-, 9-, 10-, or 11-membered bicyclic, or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any bicyclic or polycyclic group in which any of the above-defined heterocyclic rings is fused to a carbocyclic ring, the carbocyclic ring being either saturated, unsaturated, or aromatic (e.g., a benzene ring). The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include "heteroaryl" (which will be defined below). Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furyl, furazanyl, imidazolidinyl, imidazolinyl, imidazolyl, 1H-indazolyl, imidazolopyridinyl, indolenyl, indolinyl, indolizinyl, indolyl (e.g., 1H-indolyl), isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, homopiperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles. Examples of 5- to 10-membered heterocycles include, but are not limited to, pyridinyl, thienyl, pyrrolyl, furyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, IH-indazolyl, benzofuranyl, benzothiofuranyl, benztetrazolyl, benzo triazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl. Examples of 5- to 6-membered heterocycles include, but are not limited to, pyridinyl, furyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles. Examples of a bicyclic heterocyclic group include, but are not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydroquinoxalinyl, and 1,2,3,4-tetrahydro-quinazolinyl.

The term "heteroaryl" is intended to mean stable monocyclic and polycyclic aromatic hydrocarbons that include at least one heteroatom ring member such as sulfur, oxygen, or nitrogen. Heteroaryl groups are heterocyclyl groups which are aromatic, and may include, without limitation, pyridyl, pyrrolyl, pyrimidinyl, pyrazinyl, pyridazinyl, triazinyl, furyl, quinolyl, isoquinolyl, thienyl, imidazolyl, thiazolyl, indolyl (e.g., 1H-indolyl), pyrroyl, oxazolyl, benzofuryl, benzothienyl, benzthiazolyl, isoxazolyl, pyrazolyl, triazolyl, tetrazolyl, indazolyl (e.g., 1H-indazolyl), 1,2,4-thiadiazolyl, isothiazolyl, purinyl, carbazolyl, benzimidazolyl, indolinyl, benzodioxolanyl, and benzodioxane. Heteroaryl groups may be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→0 and S(O)$_p$, wherein p is 0, 1 or 2).

The term "halo" or "halogen" includes fluoro, chloro, bromo and iodo.

As used herein, the term "substituted" refers to at least one hydrogen atom that is replaced with a non-hydrogen group, provided that normal valencies are maintained and that the substitution results in a stable compound. When a substituent is noted as "optionally substituted", the substituent(s) are selected from alkyl, halo (e.g., chloro, bromo, iodo, fluoro), hydroxyl, alkoxy, oxo, alkanoyl, aryloxy, alkanoyloxy, amino (—NH$_2$), alkylamino (—NHalkyl), cycloalkylamino (—NHcycloalkyl), arylamino (—NHaryl), arylalkylamino (—NHarylalkyl), disubstituted amino (e.g., in which the two amino substituents are selected from alkyl, aryl or arylalkyl, including substituted variants thereof, with specific mention being made to dimethylamino), alkanoylamino, aroylamino, arylalkanoylamino, thiol, alkylthio, arylthio, arylalkylthio, alkylthiono, arylthiono, arylalkylthiono, alkylsulfonyl, arylsulfonyl, arylalkylsulfonyl, sulfonamide (e.g., —SO$_2$NH$_2$), substituted sulfonamide (e.g., —SO$_2$NHalkyl, —SO$_2$NHaryl, —SO$_2$NHarylalkyl, or cases where there are two substituents on one nitrogen selected from alkyl, aryl, or alkylalkyl), nitro, cyano, carboxy, unsubstituted amide (i.e. —CONH$_2$), substituted amide (e.g., —CONHalkyl, —CONHaryl, —CONHarylalkyl or cases where there are two substituents on one nitrogen selected from alkyl, aryl, or alkylalkyl), alkoxycarbonyl, aryl, guanidine, heterocyclyl (e.g., pyridyl, furyl, morpholinyl, pyrrolidinyl, piperazinyl, indolyl, imidazolyl, thienyl, thiazolyl, pyrrolidyl, pyrimidyl, piperidinyl, homopiperazinyl), and mixtures thereof. The substituents may themselves be optionally substituted, and may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

In cases wherein there are nitrogen atoms (e.g., amines) on compounds of the present disclosure, these may be converted to N-oxides by treatment with an oxidizing agent (e.g., mCPBA and/or hydrogen peroxides) to afford other compounds of this disclosure. Thus, shown and claimed nitrogen atoms are considered to cover both the shown nitrogen and its N-oxide (NO) derivative.

Compounds

In a first aspect, the present disclosure provides a compound of formula (I),

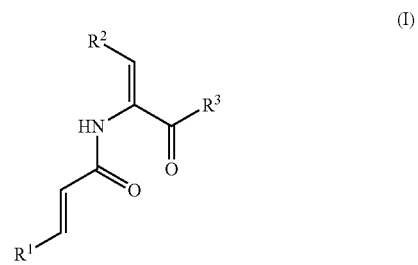

or a pharmaceutically acceptable salt, solvate, tautomer, or stereoisomer thereof, wherein:

$R^1$ is an optionally substituted aryl or an optionally substituted heteroaryl;

$R^2$ is an optionally substituted aryl or an optionally substituted heteroaryl; and $R^3$ is an optionally substituted alkylamino, an optionally substituted cycloalkylamino, an optionally substituted arylamino, an optionally substituted heterocyclylamino, an optionally substituted heterocyclyl, and an optionally substituted dialkylamino.

In preferred embodiments, the double bond formed between the enamine functionality and the $R^2$ substituent adopts a Z-configuration, that is, the enamine nitrogen and the $R^2$ substituent reside on the same side of the double bond. The double bond formed between the amide and the $R^1$ substituent may adopt either an E- or Z-configuration, preferably an E-configuration. That is, it is preferred that the amide functional group and the $R^1$ substituent reside on opposite sides of the double bond.

In some embodiments, $R^1$ is an aromatic moiety (e.g., aryl or heteroaryl) with a direct bond between the aromatic moiety and the double bond to which it is attached (such that the double bond is in conjugation with the aromatic group of $R^1$), thereby forming a cinnamamide-type moiety or a heteroarylacrylamide-type moiety. $R^1$ may be an optionally substituted monocyclic aryl or heteroaryl group or an optionally substituted bicyclic aryl or heteroaryl group, preferably $R^1$ is an optionally substituted monocyclic aryl or heteroaryl group. In some embodiments, $R^1$ may contain anywhere from 4 to 10 total carbon atoms, including any carbon atoms of substituents present, preferably 4 to 8 total carbon atoms, preferably 4 to 7 carbon atoms.

When $R^1$ is an optionally substituted heteroaryl group, it is preferred that $R^1$ is a sulfur-containing heteroaryl substituent, for example, thienyl, benzothienyl, benzisothiazolyl, isothiazolyl, isothiazolopyridinyl, benzthiazolyl, phenothiazinyl, thiazolyl, thiadiazolyl (e.g., 1,2,3-thiadiazolyl, 1,2,4-thiadiazolyl, 1,2,5-thiadiazolyl, 1,3,4-thiadiazolyl), thiazolopyridinyl, thienothiazolyl, thienooxazolyl, and thienoimidazolyl, just to name a few. Preferably, $R^1$ is an unsubstituted heteroaryl group, with specific mention being made to thienyl, preferably 2-thienyl.

When $R^1$ is an optionally substituted aryl group, it is preferred that $R^1$ is phenyl (unsubstituted) or a substituted phenyl group. When $R^1$ is a substituted phenyl group, the phenyl moiety is preferably substituted with one or more substituents selected from a halo, preferably chloro or fluoro, preferably a chloro; an alkoxy, preferably a $C_1$ to $C_4$ alkoxy, preferably a $C_1$ to $C_3$ alkoxy, preferably a $C_1$ to $C_2$ alkoxy (e.g., methoxy or ethoxy), preferably a $C_1$ alkoxy (e.g., methoxy); and an alkyl, preferably a $C_1$ to $C_4$ alkyl, preferably a $C_1$ to $C_3$ alkyl, preferably a $C_1$ to $C_2$ alkyl (e.g., methyl or ethyl), preferably a $C_1$ alkyl (e.g., methyl). In preferred embodiments, when $R^1$ is a substituted phenyl, the phenyl group is substituted (at least) in the 4-position (para to the connection to the rest of the compound of formula (I)), preferably the phenyl group contains a single substituent at the 4-position, and $R^1$ is a 4-halophenyl, a 4-alkoxyphenyl, or 4-alkylphenyl, preferably 4-chlorophenyl, 4-methoxyphenyl, or 4-methylphenyl.

In some embodiments, $R^2$ is an aromatic moiety (e.g., aryl or heteroaryl) with a direct bond between the aromatic moiety and the double bond to which it is attached, such that the double bond is in conjugation with the aromatic group of $R^2$. In some embodiments, $R^2$ may be an optionally substituted monocyclic aryl or heteroaryl group or an optionally substituted bicyclic aryl or heteroaryl group, preferably $R^2$ is an optionally substituted monocyclic aryl group or an optionally substituted bicyclic heteroaryl group. In some embodiments, $R^2$ may contain anywhere from 5 to 10 total carbon atoms, including any carbon atoms of substituents present, preferably 6 to 8 total carbon atoms, preferably 7 to 8 carbon atoms.

When $R^2$ is an optionally substituted heteroaryl group, it is preferred that $R^2$ is a nitrogen-containing heteroaryl substituent, for example, pyridyl, pyrrolyl, pyrimidinyl, pyrazinyl, pyridazinyl, triazinyl, quinolyl, isoquinolyl, imidazolyl, indolyl (e.g., 1H-indolyl), pyrroyl, oxazolyl, isoxazolyl, pyrazolyl, triazolyl, tetrazolyl, indazolyl (e.g., 1H-indazolyl), 1,2,4-thiadiazolyl, isothiazolyl, purinyl, carbazolyl, and benzimidazolyl, just to name a few. In some embodiments, $R^2$ is an optionally substituted indolyl or pyridyl, preferably a 1H-indolyl or 3-pyridyl. Preferably, $R^2$ is an unsubstituted heteroaryl group. In preferred embodiments, $R^2$ is a nitrogen-containing heteroaryl substituent having a protic —NH— group, preferably a bicyclic nitrogen-containing heteroaryl substituent having a protic —NH— group, with specific mention being made to indolyl (e.g., 1H-indolyl), benzimidazole, and indazolyl (e.g., 1H-indazolyl), preferably indolyl. In preferred embodiments, $R^2$ is 1H-indol-3-yl.

When $R^2$ is an optionally substituted aryl group, it is preferred that $R^2$ is phenyl (unsubstituted) or a substituted phenyl group. When $R^2$ is a substituted phenyl group, the phenyl moiety is preferably substituted with one or more substituents selected from a halo, preferably chloro or fluoro, preferably fluoro; a dialkylamino, preferably a di-($C_1$ to $C_4$ alkyl)amino, preferably a di-($C_1$ to $C_3$ alkyl)amino, preferably a di-($C_1$ to $C_2$ alkyl)amino, preferably a di-($C_1$ alkyl)amino (e.g., dimethylamino); an alkoxy, preferably a $C_1$ to $C_3$ alkoxy, preferably a $C_1$ to $C_2$ alkoxy (e.g., methoxy or ethoxy), preferably a $C_1$ alkoxy (e.g., methoxy); a hydroxy; and a nitro. In preferred embodiments, when $R^2$ is a substituted phenyl, the phenyl group is mono- or di-substituted, and preferably is substituted (at least) in the 4-position (para to the connection to the rest of the compound of formula (I)). In preferred embodiments, $R^2$ is a 4-halophenyl, a 4-dialkylaminophenyl, 3-alkoxy-4-hydroxyphenyl, or a 4-nitrophenyl, preferably 4-fluorophenyl, 4-dimethylaminophenyl, 3-methoxy-4-hydroxyphenyl, or 4-nitrophenyl.

$R^3$ may an optionally substituted alkylamino (—NHalkyl), an optionally substituted cycloalkylamino (—NHcycloalkyl), an optionally substituted arylamino (—NHaryl), an optionally substituted heterocyclylamino (—NH-heterocyclyl, where a nitrogen atom which is not part of the heterocyclic ring is bonded to the carbonyl group of the compound of formula (I)), an optionally substituted heterocyclyl (-heterocyclyl, where a heterocyclic ring nitrogen is directly bonded the carbonyl group of the compound of formula (I)), and an optionally substituted dialkylamino (—N(alkyl)(alkyl)).

In preferred embodiments, $R^3$ represents an amino group which is not located within a ring and which is directly bonded to one or more aliphatic hydrocarbon moieties. In some embodiments, $R^3$ is an unsubstituted $C_1$ to $C_4$ alkylamino, for example, ethylamino, n-propylamino, n-butylamino, and sec-butylamino, preferably a $C_2$ to $C_4$ alkylamino, preferably a $C_3$ to $C_4$ alkylamino, preferably a $C_3$ alkylamino. In preferred embodiments, $R^3$ is a linear unsubstituted $C_1$ to $C_4$ alkylamino, preferably n-propylamino (—NHCH$_2$CH$_2$CH$_3$). In some embodiments, $R^3$ is a substituted $C_1$ to $C_4$ alkylamino, for example, a $C_2$ to $C_4$ alkylamino in which the alkyl group is substituted with a hydroxy, an alkoxy, or a heterocyclyl group, with specific mention being made to morpholinyl, and furyl substituents (e.g., where $R^3$ is furfurylamino or 2-morpholinoethylamino). In some embodiments, $R^3$ is an optionally substituted $C_5$ to $C_{10}$ cycloalkylamino, preferably $C_5$ to $C_8$ cycloalkylamino, preferably $C_5$ to $C_6$ cycloalkylamino, for example cyclopentylamino, cyclohexylamino, and 1-adamantylamino, preferably cyclopentylamino (—NHC$_5$H$_9$). In some embodiments, $R^3$ is an optionally substituted di-($C_1$ to $C_3$ alkyl)amino, where each alkyl group attached to the amino group can be the same or different, preferably different. Preferably, $R^3$ is a di-($C_1$ to $C_2$ alkyl)amino, with specific mention being made to methylethylamino (—N(Me)Et). Most preferably, $R^3$ is a non-aromatic amino group such as an alkylamino, a cycloalkylamino, or a dialkylamino group which is either unsubstituted or which is substituted with non-aromatic substituents.

Alternatively, $R^3$ may be an amino group which is directly bonded to an aromatic moiety such as an aryl or heteroaryl group ($R^3$ is an arylamino group or a heteroarylamino group) or another heteroatom or may be an amino group in which the nitrogen that is bonded to the carbonyl group of the compound of formula (I) is present within a ring (e.g., the nitrogen is a ring nitrogen of a heterocyclic ring). For example, $R^3$ may be an optionally substituted phenylamino (e.g., phenylamino, 3-cyanophenylamino, 4-fluorophenylamino), an optionally substituted pyridylamino, an optionally substituted N-piperazinylamino ($R^3$ is a 1-piperazinylamino), an optionally substituted morpholinyl, or an optionally substituted pyrrolidinyl, In some embodiments, $R^3$ is selected from the group consisting of cyclopentylamino, 1-adamantylamino, 3-pyridylamino, 4-methyl-1-piperazinylamino, ethylamino, n-propylamino, n-butylamino, sec-butylamino, 3-cyanophenylamino, 4-fluorophenylamino, furfurylamino, 2-morpholinoethylamino, 2-hydroxyethylamino, 4-morpholinyl, 1-pyrrolidinyl, and methylethylamino. Most preferably, $R^3$ is n-propylamino.

The compound of formula (I) may be selected from the group consisting of
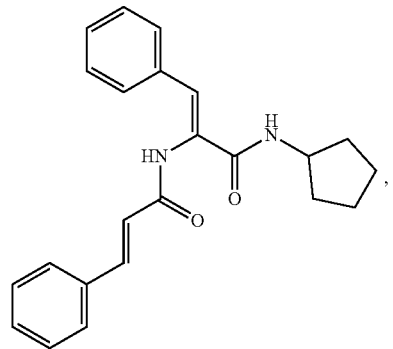
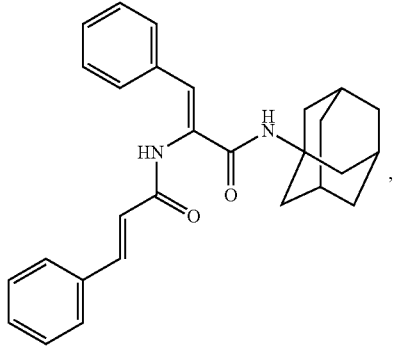
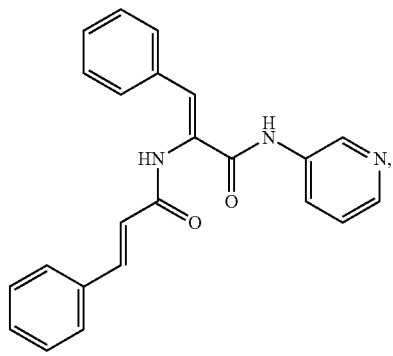
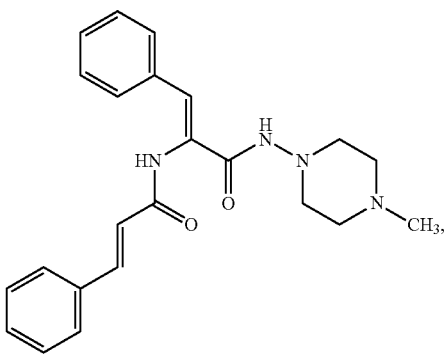
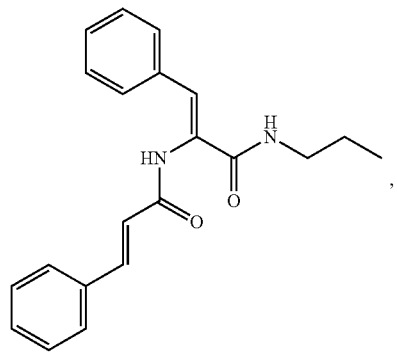
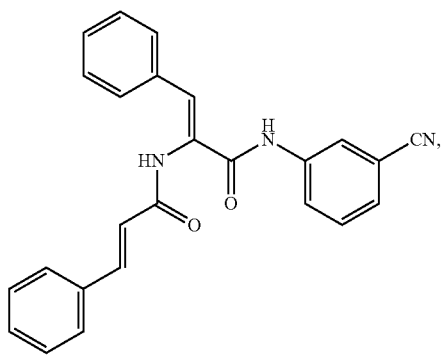
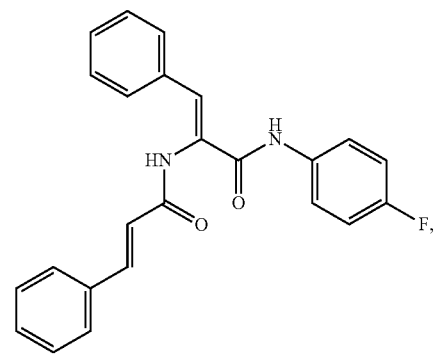
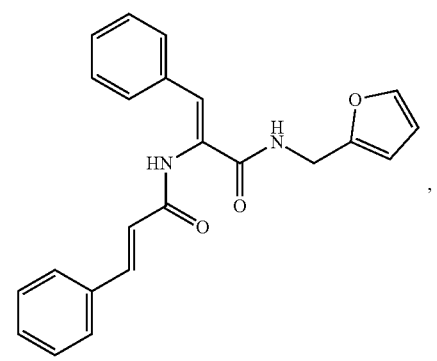

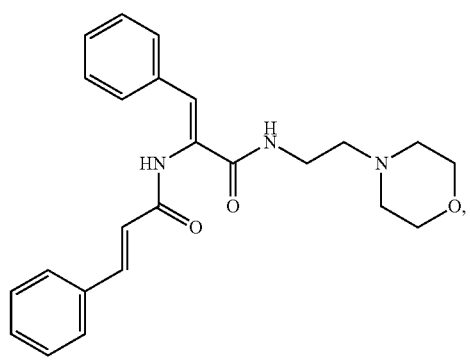
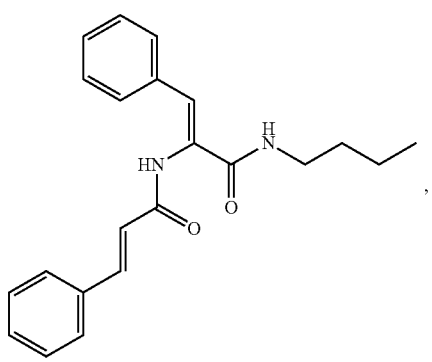
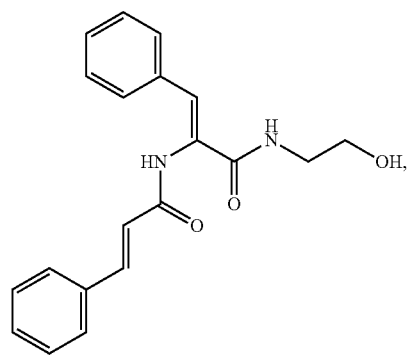
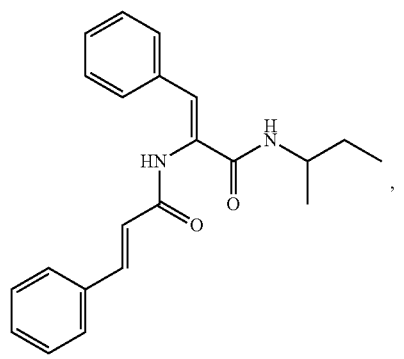
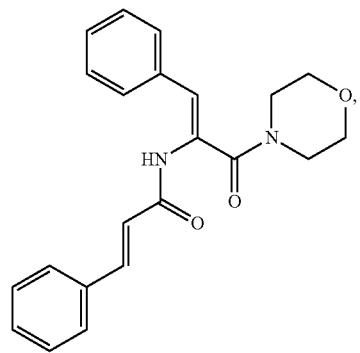
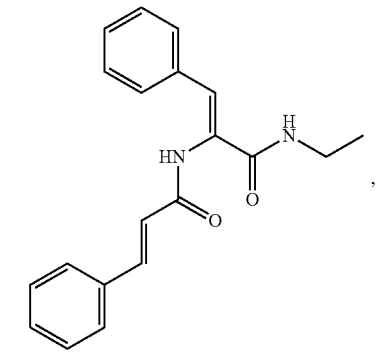
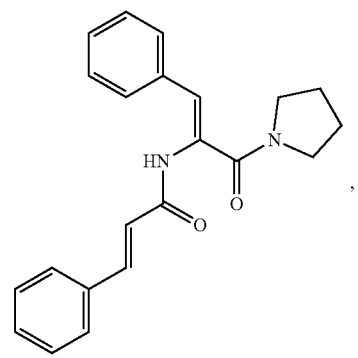
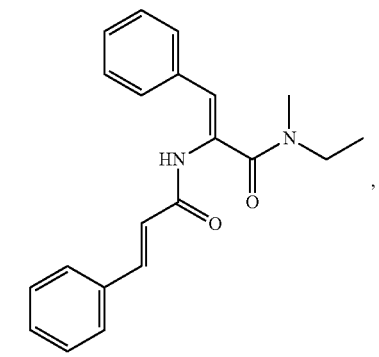

17
-continued
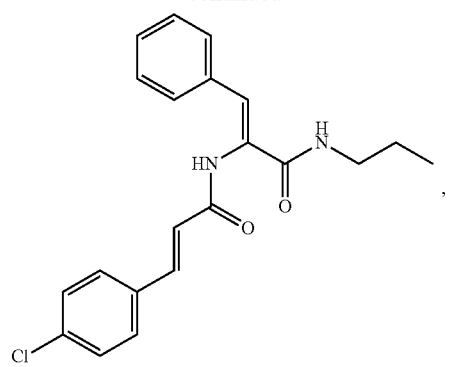
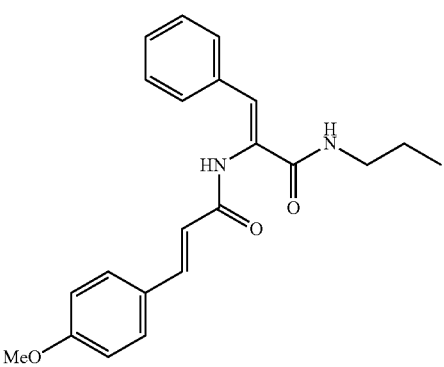
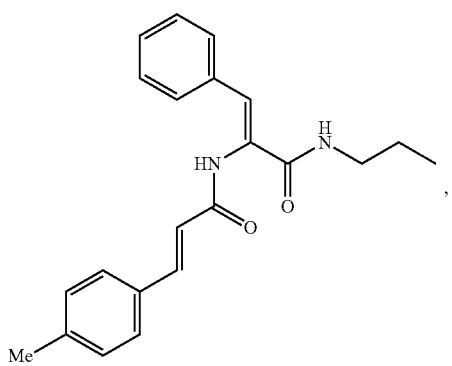
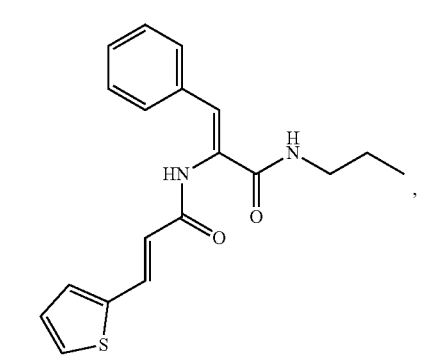
18
-continued
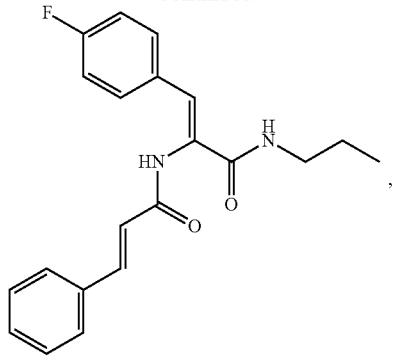
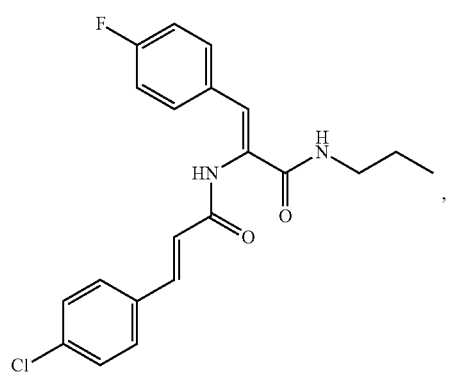
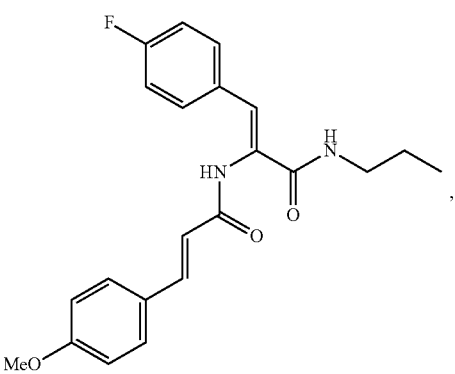
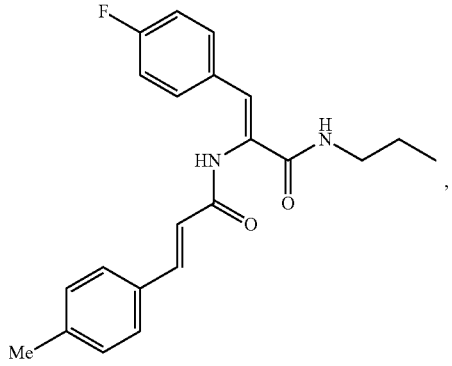

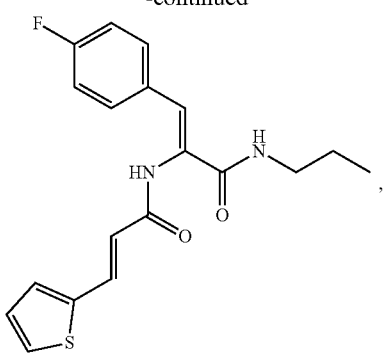
,
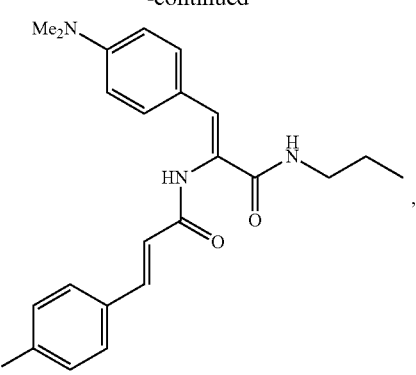
,
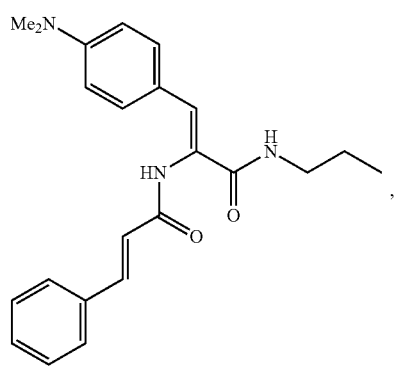
,
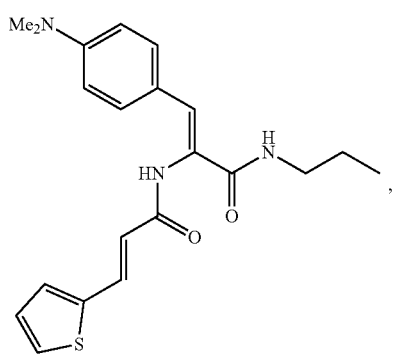
,
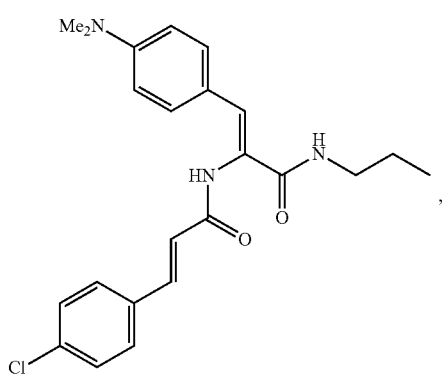
,
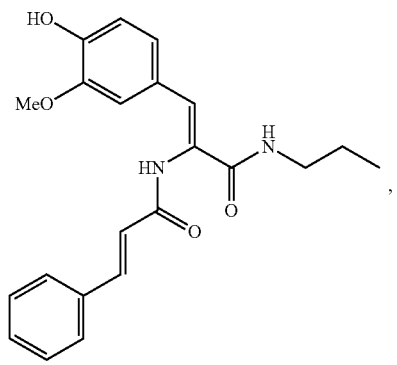
,
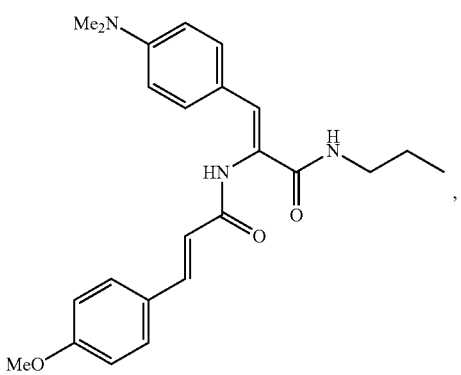
,
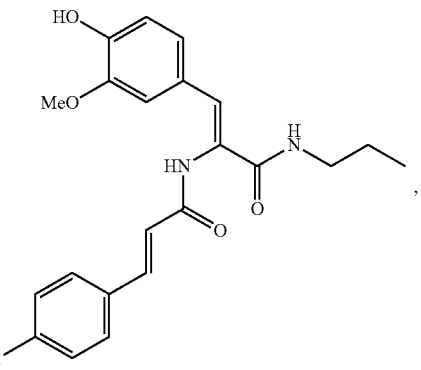
,

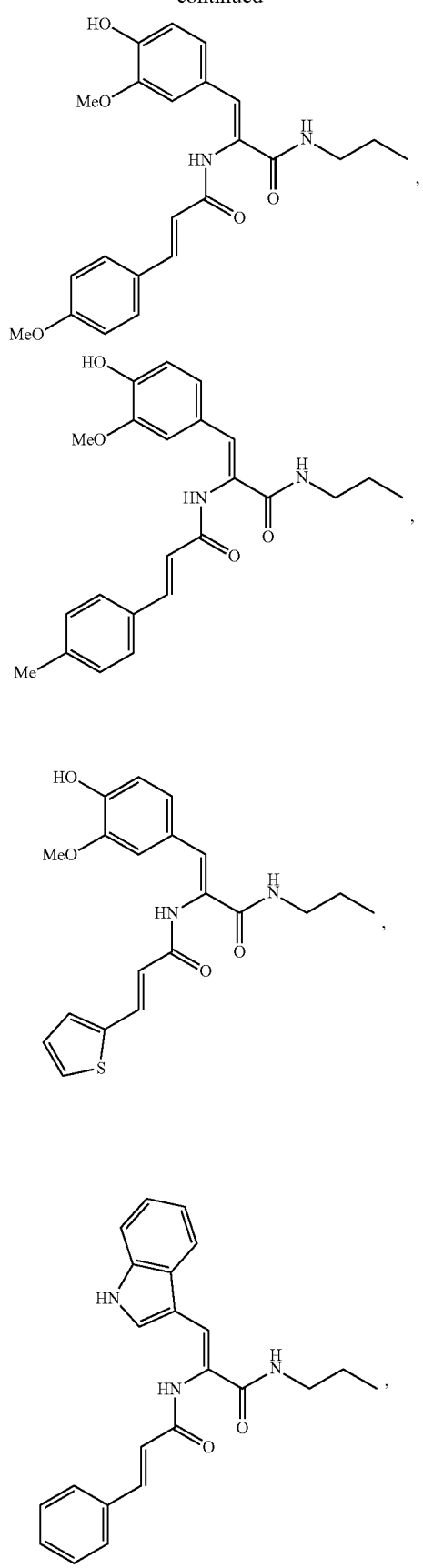

23
-continued
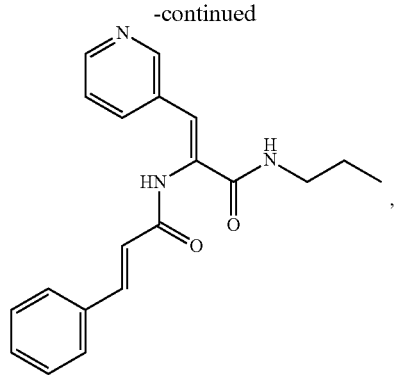
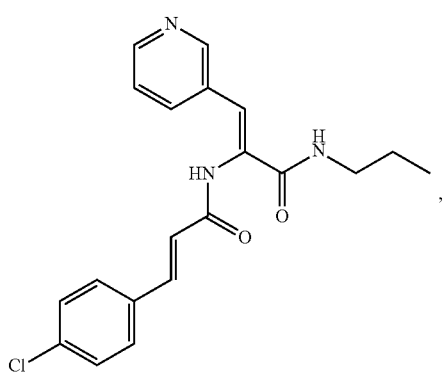
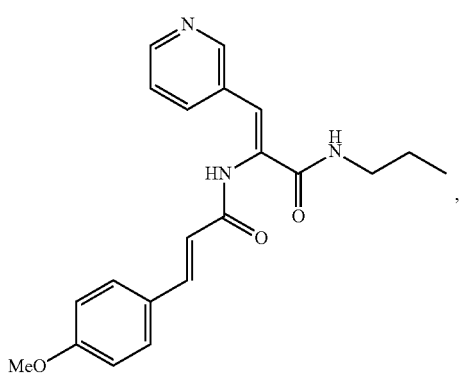
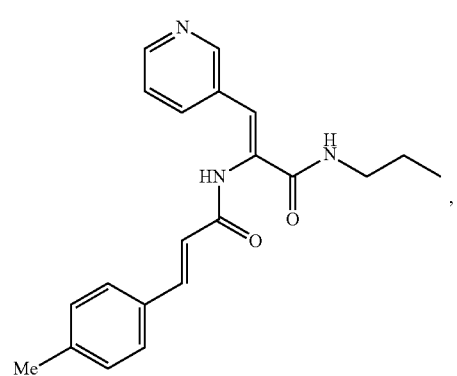
24
-continued
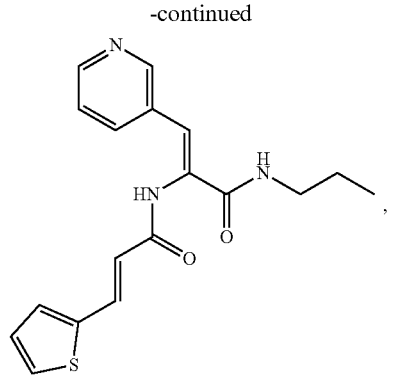
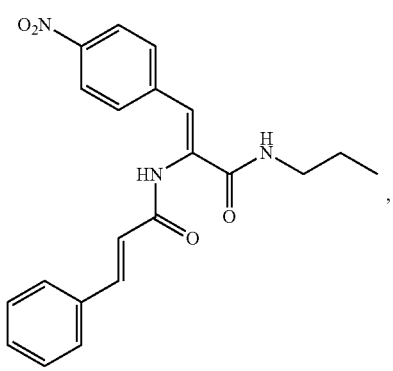
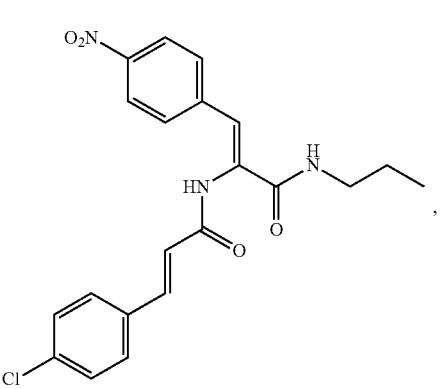
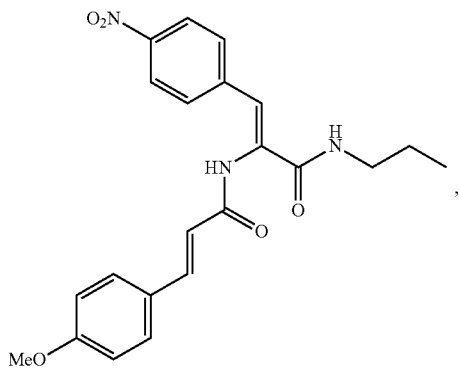

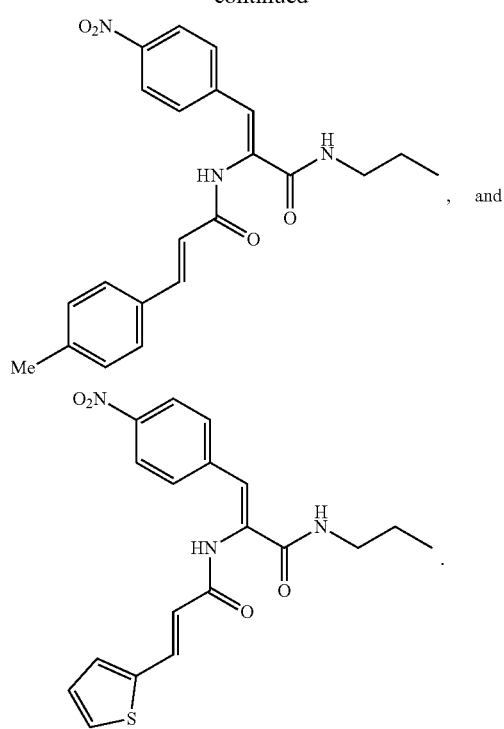
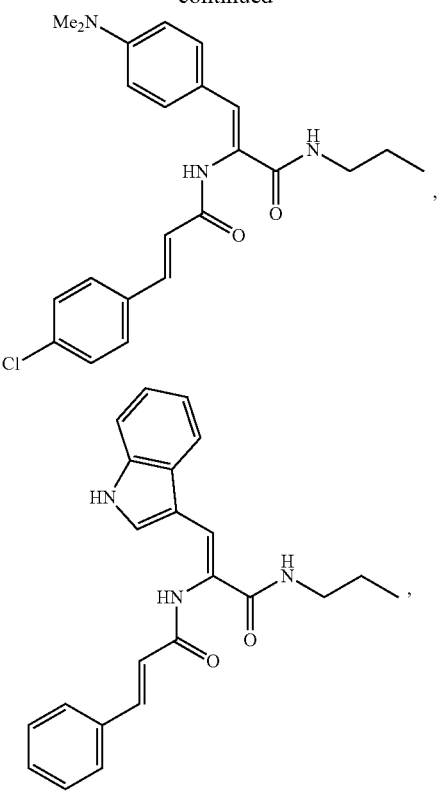
In preferred embodiments, the compound of formula (I) is selected from the group consisting of
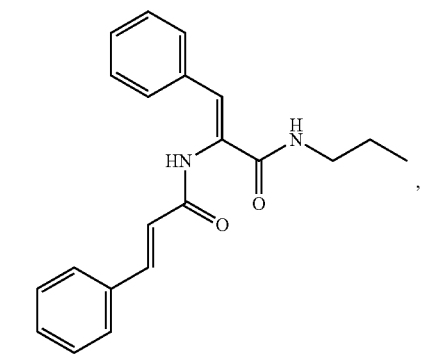
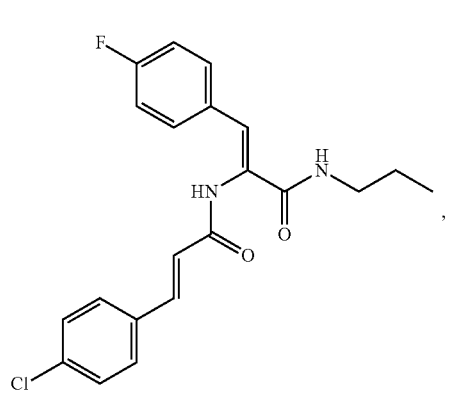
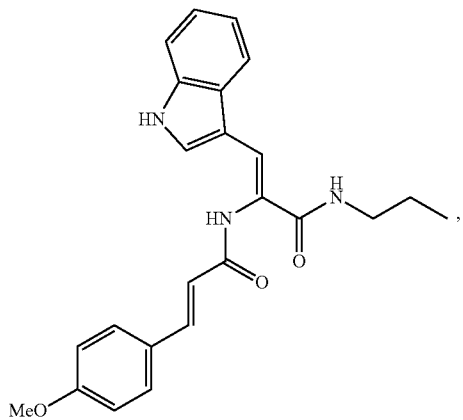

-continued

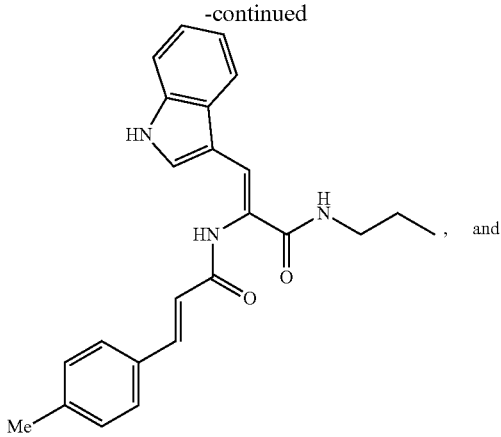

, and

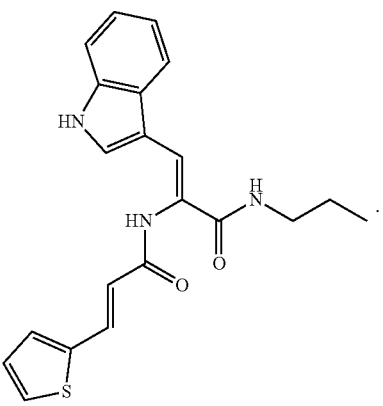

.

The compounds of the present disclosure may be prepared by methods known to those of ordinary skills in the art. The following methods set forth below are provided for illustrative purposes and are not intended to limit the scope of the disclosure.

Figure 1C:
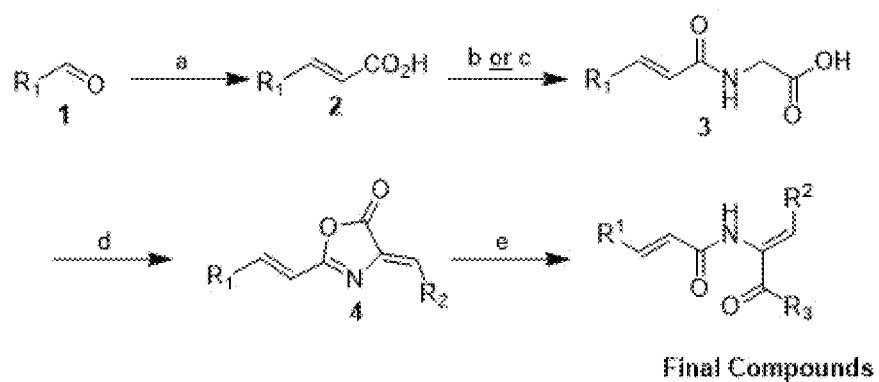
FIG. 1C illustrates a synthetic scheme used to for the synthesis of the compounds of the present disclosure: (a) malonic acid, pyridine, heat; (b) oxalyl chloride, DCM, DMF (cat.) then glycine sodium carbonate, THF, water; (c) ethyl glycinate hydrochloride, $Et_3N$, EDCI, DCM; (d) aryl aldehyde ($R_2CHO$), acetic anhydride, heat, 15 min; (e) amine form of $R_3$ in (i) DMF, microwave heating or (ii) ethanol, room temperature.

The compounds of formula (I) may, for example, be synthesized according to a Erlenmeyer-Plöchl azlactone synthetic route illustrated in FIG. 1C. Briefly, the compounds may be formed starting from an aldehyde of formula R¹CHO, which may be subjected to a condensation reaction, for example using malonic acid, an organic base (e.g., pyridine), and heat, to form a cinnamic acid compound of formula (II),

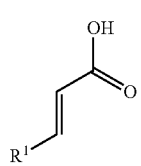

(II)

wherein R¹ is as defined previously.

The cinnamic acid compound of formula (II) may be subjected to amidation with glycine, or a salt or an ester thereof (e.g., ethylglycinate) using any known peptide bond forming technique known to those of ordinary skill in the art to form cinnamoylglycine analogs of formula (III)

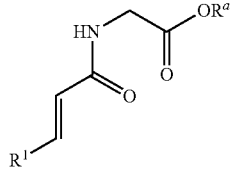

(III)

wherein $R^a$ is hydrogen (formula III is cinnamoylglycine type) or an alkyl group (formula III is cinnamoylglycinate ester type). Such peptide bond forming reactions may be accomplished using reagents including, but not limited to, carbodiimides [e.g., dicyclohexylcarbodiimide (DCC), 1-ethyl-3-(3-dimethylaminopropyl)carbodiimide (EDC or EDCI), N-cyclohexyl-N'-(2-morpholinoethyl)carbodiimide-methyl-p-toluenesulfonate (CMC)], triazolopyridines and salts thereof [e.g., 1-[bis(dimethylamino)methylene]-1H-1,2,3-triazolo[4,5-b]pyridinium 3-oxid hexafluorophosphate (HATU), 7-aza-1-hydroxybenzotriazole (HOAt)], benzotriazoles and salts thereof [e.g., 2-(1H-benzotriazol-1-yl)-1,1,3,3-tetramethyluronium hexafluorophosphate (HBTU), (benzotriazol-1-yloxy)tris(dimethylamino)phosphonium hexafluorophosphate (BOP), benzotriazol-1-yl-oxytripyrrolidinophosphonium hexafluorophosphate (PyBOP), 1-hydroxybenzotriazole (HOBt)], benzotriazin-4-ones [e.g., 3-(diethoxyphosphoryloxy)-1,2,3-benzotriazin-4(3H)-one], carbonyldiimidazole (CDI), phosgene, triphosgene, benzoates (e.g., methyl benzoate), chloroformates [e.g., butyl-, t-butyl-, isobutyl-, isopropyl-, and 4-nitrophenyl chloroformate], cyanuric chlorides and cyanuric fluorides including derivatives of cyanuric chlorides/fluorides [e.g., 2-chloro-4,6-dimethoxy-1,3,5-triazine (CDMT),4-(4,6-dimethoxy-[1,3,5]triazin-2-yl)-4-methylmorpholin-4-ium chloride (DMTMM)], N-hydroxyphthalimide, aminopyridines (e.g., 4-(dimethylamino)pyridine), thionyl chloride, oxalyl chloride, phosphorous pentachloride, bis(2-methoxyethyl)aminosulfur trifluoride, diethylaminosulfur trifluoride, and propylphosphonic anhydride (T3P). Preferably, the cinnamoylglycine analogs of formula (III) are prepared using the consecutive addition of oxalyl chloride and glycine or a salt thereof, or alternatively using a peptide coupling reagent such as EDCI and ethyl glycinate or a salt thereof.

Cyclocondensation of the cinnamoylglycine analogs of formula (III) may next be effected under Erlenmeyer conditions, for example, heating the cinnamoylglycine analogs of formula (III) in the presence of an aldehyde of formula R²CHO and a carboxylic acid anhydride (e.g., acetic anhydride), to form an azlactone (also known as an oxazolone) of formula IV

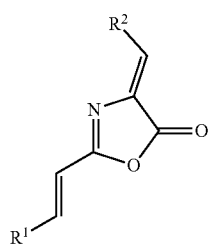

(IV)

wherein R¹ and R² are as defined previously, and the newly formed double bond adopts a Z-configuration where the azlactone ring nitrogen and the $R^2$ substituent reside on the same side of the double bond.

The azlactone of formula IV may then be reacted with a variety of aliphatic and aromatic amines (the amine form of $R^3$ whereby a nucleophilic amine group present in $R^3$ reacts with the azlactone carbonyl group) to form the compounds of formula (I). In general, reactive amines such as aliphatic and benzylic amines may react with the azlactone of formula IV under room temperature conditions, for example in an alcoholic solvent such as methanol, ethanol, propanol, isopropanol, n-butanol, isobutanol, n-pentanol, n-hexanol, 3-methyl-3-buten-1-ol, ethylene glycol, diethylene glycol, triethylene glycol, tetraethylene glycol, propylene glycol, dipropylene glycol, 1,3-propanediol, etc., while less reactive amines such as aromatic amines may be reacted with the azlactone of formula IV using heat (e.g., microwave heat) and high boiling solvents such as dimethylformamide.

The progress of any such reactions may be monitored by methods known to those of ordinary skill in the art, such as thin layer chromatography, gas chromatography, nuclear magnetic resonance, infrared spectroscopy, and high pressure liquid chromatography combined with ultraviolet detection or mass spectroscopy. The compounds of formula (I) may be isolated and purified by methods known to those of ordinary skill in the art, such as one or more of crystallization, precipitation, filtration, solvent evaporation, aqueous work-up, solvent extraction, drying, distillation, column chromatography, high pressure liquid chromatography (HPLC), lyophilization, and the like.

Of course, it should be understood that the compounds of formula (I) may be synthesized through various other synthetic schemes, reactions types and conditions, and isolation/purification procedures and still be considered a part of the present disclosure.

Pharmaceutical Compositions

According to a second aspect, the present disclosure relates to a pharmaceutical composition which comprises a therapeutically effective amount of one or more of the compounds of formula (I), formulated together with one or more pharmaceutically acceptable carriers and/or excipients, and optionally, one or more additional therapeutic agents. As described in detail below, the pharmaceutical compositions of the present disclosure may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, a "composition" or a "pharmaceutical composition" refers to a mixture of an active ingredient(s) with other chemical components, such as pharmaceutically acceptable carriers and/or excipients. One purpose of a composition is to facilitate administration of the compounds disclosed herein in any of its embodiments to a subject. Pharmaceutical compositions of the present disclosure may be manufactured by processes well known in the art, e.g., by means of conventional mixing, dissolving, granulating, dragee-making, levigating, emulsifying, encapsulating, entrapping or lyophilizing processes. Depending on the intended mode of administration (e.g., oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient" or "active compound", as used herein, refers to an ingredient in the composition that is biologically active, for example, one or more compounds represented by formula (I), a salt thereof, a solvate thereof, a tautomer thereof, a stereoisomer thereof, or any mixtures thereof. In some embodiments, additional therapeutic agents, in addition to the compound of the current disclosure, may be incorporated into a pharmaceutical composition, for example, a second active ingredient which is chemically distinct from the compounds of formula (I).

When the compounds of formula (I) are administered as pharmaceuticals, to humans and animals, they can be given per se or as a pharmaceutical composition containing, for example, 0.1 to 99 wt. % of active ingredient(s) in combination with a pharmaceutically acceptable carrier and/or excipient. In some embodiments, the pharmaceutical composition comprises 0.01 to 99 wt. % of the compound of formula (I) relative to a total weight of the pharmaceutical composition. For example, the pharmaceutical composition may contain at least 0.01 wt. %, at least 0.05 wt. %, at least 0.1 wt. %, at least 0.5 wt. %, at least 5 wt. %, at least 10 wt. %, at least 15 wt. %, at least 20 wt. %, at least 25 wt. %, at least 30 wt. %, at least 35 wt. %, at least 40 wt. %, at least 45 wt. %, at least 50 wt. %, at least 55 wt. %, at least 60 wt. %, at least 65 wt. %, at least 70 wt. %, and up to 99 wt. %, up to 98 wt. %, up to 95 wt. %, up to 90 wt. %, up to 85 wt. %, up to 80 wt. %, up to 75 wt. % of the compound of formula (I) relative to a total weight of the pharmaceutical composition. In preferred embodiments, the pharmaceutical composition includes 5 to 15 wt. %, preferably 6 to 14 wt. %, preferably 7 to 13 wt. %, preferably 8 to 12 wt. %, preferably 9 to 11 wt. %, preferably 10 wt. % of the compound of formula (I), based on a total weight of the pharmaceutical composition.

In some embodiments, the active ingredient of the current disclosure, e.g., the compound of formula (I), a salt thereof, a solvate thereof, a tautomer thereof, a stereoisomer thereof, or any mixtures thereof, may provide utility as an anticancer agent in reducing the viability of cancer cells derived from human cancer cell lines including, but not limited to, breast cancer cell lines (e.g., MDA-MB-231, MCF-7, SK-BR-3, T47D, VP303); stomach cancer cell lines (e.g., N87, SNU-16, SNU-5, SNU-1, KATO III, AGS); colon/colorectal cancer cell lines (e.g., HCT-116, CACO-2, HT-29, HCT15, MDST8, GP5d, DLD1, SW620, SW403, T84); leukemia cell lines (e.g., HL-60, CESS, CCRF-CEM, CEM/C1, KASUMI-1, ARH-77); liver cancer cell lines (e.g., HepG2, PLC/PRF/5, THLE-3, C3A, SNU-182, SNU-398, SNU-387, SNU-423, SNU-475, SNU-449, and Hep 3B2.1-7); lung cancer cell lines (e.g., A549, NCI-H460, SHP-77, COR-L23/R, NCI-H69/LX20); brain tumor cell lines (e.g., U251);

ovarian cancer cell lines (e.g., NCI-ADR/RES, OVCAR-03, A2780, A2780cis, OV7, PEO23); prostate cancer cell lines (e.g., PC-3); renal cancer cell lines (e.g., 786-0); and skin cancer or melanoma cell lines (e.g., UACC-62, C32TG, A375, MCC26). Preferably, the active ingredient of the current disclosure, e.g., the compound of formula (I), a salt thereof, a solvate thereof, a tautomer thereof, a stereoisomer thereof, or any mixtures thereof, provides utility as an anticancer agent in reducing the viability of cancer cells derived from human colon/colorectal cancer cell lines (e.g., HCT-116, CACO-2, HT-29).

In some embodiments, the cancer cells are collected from a human patient who is at risk of having, is suspected of having, has been diagnosed with, or is being monitored for recurrence of at least one type of cancer, preferably colon/colorectal cancer.

In some embodiments, the ability of the active ingredient to reduce the viability of cancer cells may be determined by contacting the pharmaceutical composition with the cancer cells and then performing cell viability assays. Methods of such assays include, but are not limited to, sulforhodamine-B (SRB) assay, ATP test, Calcein AM assay, clonogenic assay, ethidium homodimer assay, Evans blue assay, 2',7'-dichlorofluorescin diacetate (DCFDA) staining assay, fluorescein diacetate hydrolysis/propidium iodide staining assay, annexin V/fluorescein isothiocyanate (FITC)/propidium iodide staining assay, flow cytometry, Formazan-based assays (MTT, XTT), green fluorescent protein assay, lactate dehydrogenase (LDH) assay, methyl violet assay, propidium iodide assay, Resazurin assay, trypan blue assay, 4',6'-diamidino-2-phenylindole (DAPI) assay, TUNEL assay, and primary (1°) colonosphere formation assay. In a preferred embodiment, a MTT assay is used. In another preferred embodiment, a Resazurin assay is used.

As is well understood in the art, the $IC_{50}$ value of a compound/mixture is a concentration of that compound/mixture which causes the death of 50% of the cellular population to which the compound/mixture is added. In some embodiments, the $IC_{50}$ of the compound of formula (I), the salt thereof, the solvate thereof, the tautomer thereof, the stereoisomer thereof, or the mixture thereof against colorectal cancer cells, for example HCT-116, CACO-2, and HT-29 human cancer cell lines, is less than 200 μM, preferably less than 150 μM, preferably less than 100 μM, preferably less than 90 μM, preferably less than 80 μM, preferably less than 70 μM, preferably less than 60 μM, preferably less than 50 μM, preferably less than 40 μM, preferably less than 30 μM, preferably less than 25 μM, preferably less than 20 μM, preferably less than 15 μM, preferably less than 10 μM, preferably less than 5 μM, preferably less than 4 μM, preferably less than 3 μM, preferably less than 2 μM, preferably less than 1 μM, for example, from 0.8 to 20 μM, preferably from 0.9 to 15 μM, preferably from 1 to 10 μM, preferably from 1.5 to 8 μM, preferably from 2 to 6 μM.

In some embodiments, additional therapeutic agents in addition to the compound of the current disclosure may be incorporated into the pharmaceutical composition. In some embodiments, the pharmaceutical composition includes an additional therapeutic agent that is chemically distinct from the compound of formula (I), such as a chemotherapeutic agent or an anticancer agent, for the treatment or prevention of neoplasm, of tumor or cancer cell division, growth, proliferation and/or metastasis in the subject; induction of death or apoptosis of tumor and/or cancer cells; and/or any other forms of proliferative disorder.

The additional therapeutic agent may be an anticancer agent and may include, but is not limited to, at least one of a mitotic inhibitor; an alkylating agent; an antimetabolite; a cell cycle inhibitor; an enzyme; a topoisomerase inhibitor; a biological response modifier; an anti-hormone; a tubulin inhibitor; a tyrosine-kinase inhibitor; an antiangiogenic agent such as MMP-2, MMP-9 and COX-2 inhibitor; an anti-androgen; a platinum coordination complex (oxaliplatin, carboplatin); a substituted urea such as hydroxyurea; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane).

Exemplary additional therapeutic agents include, but are not limited to, tubulin binding agents including paclitaxel, epothilone, docetaxel, discodermolide, etoposide, vinblastine, vincristine, teniposide, vinorelbine, and vindesine; tyrosine-kinase inhibitors including imatinib, nilotinib, dasatinib, bosutinib, ponatinib, and bafetinib; alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; cytotoxic antibiotics including daunorubicin, doxorubicin, idarubicin, mitomycin, actinomycin, epirubicin; topoisomerase inhibitors including irinotecan, mitoxantrone, topotecan, and mixtures thereof.

As used herein, the phrase "pharmaceutically acceptable carrier and/or excipient" means a pharmaceutically acceptable material, composition or vehicle, such as a liquid or solid filler, carrier, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations, such as cyclodextrins, liposomes, and micelle forming agents, e.g., bile acids, just to name a few.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the pharmaceutical compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Methods of preparing these pharmaceutical compositions include the step of bringing into association a compound of formula (I) with the pharmaceutically acceptable carrier and/or excipient, and, optionally, one or more accessory ingredients. In general, the compositions are prepared by uniformly and intimately bringing into association a compound of the present disclosure with liquid carriers, or finely divided solid carriers, or both, and then, if necessary, shaping the product.

Pharmaceutical compositions of the present disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of formula (I) as an active ingredient. A compound of formula (I) of the present disclosure may also be administered as a bolus, electuary or paste.

In solid dosage forms of the present disclosure for oral administration (capsules, tablets, pills, dragees, powders, granules, troches and the like), the active ingredient is mixed with one or more pharmaceutically acceptable carriers and/or excipients, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants (e.g., fatty acid esters of sorbitan and polyalkolyated fatty acid esters of sorbitan such as TWEEN 80, available from Sigma-Aldrich); (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like. A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered compound moistened with an inert liquid diluent. The tablets, and other solid dosage forms of the pharmaceutical compositions of the present disclosure may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above described excipients.

Liquid dosage forms for oral administration of the compounds of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, com, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compound, may contain suspending agents as, for example, ethoxylated isostearyl alcohols, polyoxyethylene sorbitol and sorbitan esters (including polyoxyethylene fatty acid esters of sorbitan, e.g., TWEEN 80), microcrystalline cellulose, aluminum metahydroxide, bentonite, agar-agar and tragacanth, and mixtures thereof. In preferred embodiments, the pharmaceutical composition is in the form of a suspension, comprising, consisting of, or consisting essentially of the compound of formula (I) and the pharmaceutically acceptable carrier and/or excipient, which is preferably a suspending agent (preferably a polyoxyethylene sorbitan ester, preferably a polyoxyethylene fatty acid ester of sorbitan, e.g., TWEEN 80) in an inert diluent (preferably water). Preferably the content of the suspending agent in the suspension ranges from 0.01 to 1 wt. %, preferably 0.05 to 0.8 wt. %, preferably 0.1 to 0.6 wt. %, preferably 0.5 wt. %, based on a total weight of the suspension.

Formulations of the pharmaceutical compositions of the disclosure for rectal or vaginal administration may be presented as a suppository, which may be prepared by mixing one or more compounds of formula (I) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound(s).

Formulations of the pharmaceutical compositions which are suitable for vaginal administration also include pessaries, tampons, creams, gels, pastes, foams or spray formulations containing such carriers as are known in the art to be appropriate.

Dosage forms for the topical or transdermal administration of a compound of this disclosure include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this disclosure, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this disclosure.

Pharmaceutical compositions of this disclosure suitable for parenteral administration comprise one or more compounds of formula (I) in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants (e.g., TWEEN 80).

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the pharmaceutical compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly (anhydrides). Depot injectable formulations are also prepared by entrapping the drug in liposomes or microemulsions which are compatible with body tissue.

In some embodiments, the pharmaceutical composition contains 1 to 99.9 wt. %, preferably 5 to 95 wt. %, preferably 10 to 90 wt. %, preferably 15 to 85 wt. %, preferably 20 to 80 wt. %, preferably 30 to 75 wt. %, preferably 40 to 70 wt. %, preferably 50 to 65 wt. % of the pharmaceutically acceptable carrier and/or excipient, relative to a total weight of the pharmaceutical composition.

Therapeutic Applications and Methods

According to a third aspect, the present disclosure relates to a method for treating a proliferative disorder. The method involves administering a therapeutically effective amount of one or more compounds of formula (I) per se, or a pharmaceutical composition of the second aspect to a subject.

In some embodiments, the proliferative disorder is cancer. Types of cancers that may be treated with the compounds of this disclosure include, but are not limited to, brain cancers, skin cancers, bladder cancers, ovarian cancers, breast cancers, gastric cancers, pancreatic cancers, prostate cancers, colon/colorectal cancers, blood cancers, lung cancers and bone cancers. In some embodiments, the compounds of this disclosure can be used for the treatment of any cancer type that fails to undergo apoptosis in a patient. This includes, but is not limited to: solid tumors, including but not limited to carcinomas; sarcomas including Kaposi's sarcoma; erythroblastoma; glioblastoma; meningioma; astrocytoma; melanoma; and myoblastoma. Treatment or prevention of non-solid tumor cancers, such as leukemia, is also contemplated by this invention.

Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Bur-kitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse laige B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma. In preferred embodiments, the cancer is colon or colorectal cancer.

As used herein, the terms "treat", "treatment", and "treating" in the context of the administration of a therapy to a subject in need thereof refers to the reduction or inhibition of the progression and/or duration of a disease (e.g., cancer), the reduction or amelioration of the severity of the disease, the amelioration of one or more symptoms thereof resulting from the administration of one or more therapies, preventing the disease from occurring in a subject that may be predisposed to the disease but does not yet experience or exhibit symptoms of the disease (prophylactic treatment), slowing or arresting disease development, ameliorating the disease, providing relief from the symptoms or side-effects of the disease (including palliative treatment), and causing regression of the disease. Specific to cancer, and in particular colon or colorectal cancer, these terms may refer to: (1) a stabilization, reduction (e.g., by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g., by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g., colectomy, mastectomy), and (14) preventing or reducing (e.g., by more than 10%, more than 30%, preferably by more than 60% of the population of metastasized cancer cells before administration) the metastasis of cancer cells.

The term "subject" and "patient" are used interchangeably. As used herein, they refer to any subject for whom or which therapy, including with the compositions according to the present disclosure is desired. In most embodiments, the subject is a mammal, including but not limited to a human, a non-human primate such as a chimpanzee, a domestic livestock such as a cattle, a horse, a swine, a pet animal such as a dog, a cat, and a rabbit, and a laboratory subject such as a rodent, e.g., a rat, a mouse, and a guinea pig. In preferred embodiments, the subject is a human.

The subject may be any subject already with the disease, a subject which does not yet experience or exhibit symptoms of the disease, or a subject predisposed to the disease. In preferred embodiments, the subject is a person who is predisposed to cancer, e.g., a person with a family history of cancer. Women who have (i) certain inherited genes (e.g., mutated BRCA1 and/or mutated BRCA2), (ii) been taking estrogen alone (without progesterone) after menopause for many years (at least 5, at least 7, or at least 10), and/or (iii) been taking fertility drug clomiphene citrate, are at a higher risk of contracting breast cancer. People who (i) consumes a diet high in salty and smoked foods and/or low in fruits and vegetables, (ii) had infection with *Helicobacter pylori*, and/or (iii) long-term stomach inflammation are at a higher risk of contracting stomach cancer. People who (i) had chemotherapy and radiation therapy for other cancers, (ii) has genetic disorders, such as Down syndrome, and/or (iii) exposure to certain chemicals, such as benzene are at a higher risk of contracting leukemia. People who (i) had inflammatory bowel disease, or a genetic syndrome such as familial adenomatous polyposis (FAP) and hereditary non-polyposis colorectal cancer (Lynch syndrome), and/or (ii) consumes a low-fiber and high-fat diet are at a higher risk of contracting colon cancer. Any subject with such predispositions, in combination with sound medical judgment, may be candidates for the treatment methods described herein.

In some embodiments, the subject has leukemia, stomach, colon, and/or breast cancer and is currently undergoing, or has completed one or more chemotherapy regimens. In some embodiments, the subject has been previously administered/treated with, or is being currently administered/treated with, a thymidylate synthase inhibitor (e.g., capecitabine, fluorouracil (5-FU)), a thymidine phosphorylase (TPase) inhibitor (e.g., tipiracil, trifluridine), topoisomerase I inhibitor (e.g., irinotecan), a DNA synthesis inhibitor (e.g., oxaliplatin), and/or a targeted therapy (e.g., cetuximab, bevacizumab, panitumumab, zivaflibercept, ramucirumab). In some embodiments, the subject has been previously administered/treated with, or is being currently administered/treated with, a tubulin binding drug such as paclitaxel, epothilone, docetaxel, discodermolide, etoposide, vinblastine, vincristine, teniposide, vinorelbine, and vindesine, and developed resistance to the tubulin binding drug. In some embodiments, the subject has been previously administered/treated with, or is being currently administered/treated with, a tyrosine-kinase inhibitor such as imatinib, nilotinib, dasatinib, bosutinib, ponatinib, and bafetinib, and developed drug resistance via (i) Bcr-Abl dependent mechanisms involving Bcr-Abl duplication, Bcr-Abl mutation, T315I mutation, and/or P-loop mutations, or (ii) Bcr-Abl Independent mechanisms involving drug efflux caused by P-glycoproteins, drug import by organic cation transporter 1, and/or alternative signaling pathway activation.

The terms "administer", "administering", "administration", and the like, as used herein, refer to the methods that may be used to enable delivery of the active ingredient and/or the pharmaceutical composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed. In preferred embodiments, the active ingredient (e.g., the compound of formula (I)) or the pharmaceutical composition described herein are administered orally, preferably as an oral suspension.

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", or "pharmaceutically effective amount" refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. Typically, an effective amount of the compound of formula (I) to treat cancers such as colon or colorectal cancer, in terms of mg of the compound of formula (I) per body weight of the subject (kg), ranges from 0.1 to 2,000 mg/kg, preferably 1 to 1,500 mg/kg, preferably 5 to 1,000 mg/kg, preferably 10 to 900 mg/kg, preferably 15 to 800 mg/kg, preferably 20 to 700 mg/kg, preferably 30 to 600 mg/kg, preferably 40 to 500 mg/kg, preferably 50 to 400 mg/kg, preferably 60 to 300 mg/kg, preferably 70 to 200 mg/kg, preferably 80 to 150 mg/kg, preferably 90 to 100 mg/kg.

Compounds of the disclosure may be useful for sensitizing cells to apoptotic signals. Thus, in some embodiments, the compounds of the disclosure are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin ortopotecan; (vii) topoisomerase II poisons, (viii) microtubule-directed agents, (ix) kinase inhibitors (x) miscellaneous investigational agents (xi) hormones, (xii) hormone antagonists, and (xii) targeted therapies. It is contemplated that compounds of the disclosure may be useful in combination with any known agents falling into the above 13 classes as well as any future agents that are currently in development. In particular, it is contemplated that compounds of the disclosure may be useful in combination with current Standards of Care as well as any that evolve over the foreseeable future. Specific dosages and dosing regimens would be based on physicians' evolving knowledge and the general skill in the art.

Examples of second therapeutic agents include, but are not limited to, a mitotic inhibitor; an alkylating agent; an antimetabolite; a cell cycle inhibitor; an enzyme; a topoisomerase inhibitor; a biological response modifier; an antihormone; a tubulin inhibitor; a tyrosine-kinase inhibitor; an antiangiogenic agent such as MMP-2, MMP-9 and COX-2 inhibitor; an anti-androgen; a platinum coordination complex (oxaliplatin, carboplatin); a substituted urea such as hydroxyurea; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane); a thymidylate synthase inhibitor; a thymidine phosphorylase (TPase) inhibitor; a DNA synthesis inhibitor; and/or a targeted therapy. Exemplary second therapeutic agents include, but are not limited to, tubulin binding agents including paclitaxel, epothilone, docetaxel, discodermolide, etoposide, vinblastine, vincristine, teniposide, vinorelbine, and vindesine; tyrosine-kinase inhibitors including imatinib, nilotinib, dasatinib, bosutinib, ponatinib, and bafetinib; alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; cytotoxic antibiotics including daunorubicin, doxorubicin, idarubicin, mitomycin, actinomycin, epirubicin; topoisomerase inhibitors including irinotecan, mitoxantrone, topotecan; thymidine phosphorylase (TPase) inhibitors such as tipiracil and trifluridine; DNA synthesis inhibitors such as oxaliplatin; targeted therapies such as cetuximab, bevacizumab, panitumumab, zivafliber- cept, ramucirumab; and mixtures thereof.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A treatment method may comprise administering the compound of formula (I) or a pharmaceutical composition containing the compound of formula (I) of the current disclosure in any of its embodiments as a single dose or multiple individual divided doses. In some embodiments, the composition is administered at various dosages (e.g., a first dose with an effective amount of 200 mg/kg and a second dose with an effective amount of 50 mg/kg). In some embodiments, the interval of time between the administration of the pharmaceutical composition and the administration of one or more second therapies may be about 1 to 5 minutes, 1 to 30 minutes, 30 minutes to 60 minutes, 1 hour, 1 to 2 hours, 2 to 6 hours, 2 to 12 hours, 12 to 24 hours, 1 to 2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11 to 15 weeks, 15 to 20 weeks, 20 to 30 weeks, 30 to 40 weeks, 40 to 50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, at least 5 days, at least 6 days, or at least 7 days. In some embodiments, the pharmaceutical composition and optionally one or more second therapies are administered less than 1 day, less than 1 week, less than 2 weeks, less than 3 weeks, less than 4 weeks, less than 1 month, less than 2 months, less than 3 months, less than 6 months, less than 1 year, less than 2 years, or less than 5 years apart.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, at least 10%, at least 15%, at least 20%, at least 25%, at least 30%, at least 40%, at least 50%, at least 60%, at least 70%, at least 75%, at least 80%, at least 85%, at least 90%, at least 95%, at least 99%, or 100%, relative to the tumor size before treatment. In some embodiments, the size of a tumor after treatment is not reduced but is maintained at the same size as before treatment. Methods of assessing tumor size include, but are not limited to, CT scan, MRI, DCE-MRI and PET scan.

The method may further comprise measuring a concentration of a biomarker and/or detecting a mutation in a biomarker before and/or after the pharmaceutical composition comprising the compound of formula (I) of the present disclosure is administered. Generic cancer biomarkers include circulating tumor DNA (ctDNA) and circulating tumor cells (CTC). Exemplary biomarkers for colon cancer include, without limitation, carcinoembryonic antigen (CEA), carbohydrate antigen 242 (CA 242), CA 195, CA 19-9, MS1, and 18qLOH. Exemplary biomarkers for breast cancer include, without limitation, BRCA1, BRCA2, HER-2, estrogen receptor, progesterone receptor, cancer antigen 15-3, cancer antigen 27.29, carcinoembryonic antigen, Ki67, cyclin D1, cyclin E, and ERβ. Exemplary biomarkers for stomach cancer include, without limitation, carcinoembryonic antigen (CEA), CA19-9, carbohydrate antigen (CA) 72-4, alpha-fetoprotein, carbohydrate antigen (CA)12-5, SLE, BCA-225, hCG, and pepsinogen I/II.

Potentially predictive cancer biomarkers include, without limitation, mutations in genes BRCA1 and BRCA2 for breast cancer, overexpressions of TYMS, mutations in genes p53 and KRAS for colon cancer, and high concentration levels of AFP, and overexpressions of HSP90α for liver cancer.

The mutation in the biomarker may be detected by procedures such as restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA). The procedures to detect the mutation are well-known to those of ordinary skill in the art.

The concentration level of the cancer biomarker in a sample (i.e., biological sample obtained from the subject in need of therapy including a single cell, multiple cells, fragments of cells, a tissue sample, and/or body fluid, for example red blood cells, white blood cells, platelets, hepatocytes, epithelial cells, endothelial cells, a skin biopsy, a mucosa biopsy, an aliquot of urine, saliva, whole blood, serum, plasma, lymph) may be measured for example by an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

In some embodiments, a concentration of the biomarker is measured before and after the administration. When the concentration of the biomarker is maintained, the method may further comprise increasing the effective amount of the compound of formula (I) by at least 5%, at least 10%, or at least 30%, and up to 80%, up to 60%, or up to 50% of an initial effective amount. The subject may be administered with the increased dosage for a longer period (e.g., 1 week more, 2 weeks more, or 2 months more) than the duration prescribed with the initial effective amount.

In some embodiments, the administration is stopped once the subject is treated.

The examples below are intended to further illustrate protocols for preparing, characterizing, and using the compounds of the present disclosure, and are not intended to limit the scope of the claims.

Where a numerical limit or range is stated herein, the endpoints are included. Also, all values and subranges within a numerical limit or range are specifically included as if explicitly written out.

The terms "comprise(s)", "include(s)", "having", "has", "can", "contain(s)", and variants thereof, as used herein, are intended to be open-ended transitional phrases, terms, or words that do not preclude the possibility of additional acts or structures. The present disclosure also contemplates other embodiments "comprising", "consisting of" and "consisting essentially of", the embodiments or elements presented herein, whether explicitly set forth or not.

As used herein, the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

EXAMPLES

Results

Chemical Synthesis of 3-aryl-2-[(3-arylpropenoyl)amino]-N-substituted-propenamide Derivatives (MOS-1503 to MOS-5112)

Figure 2:
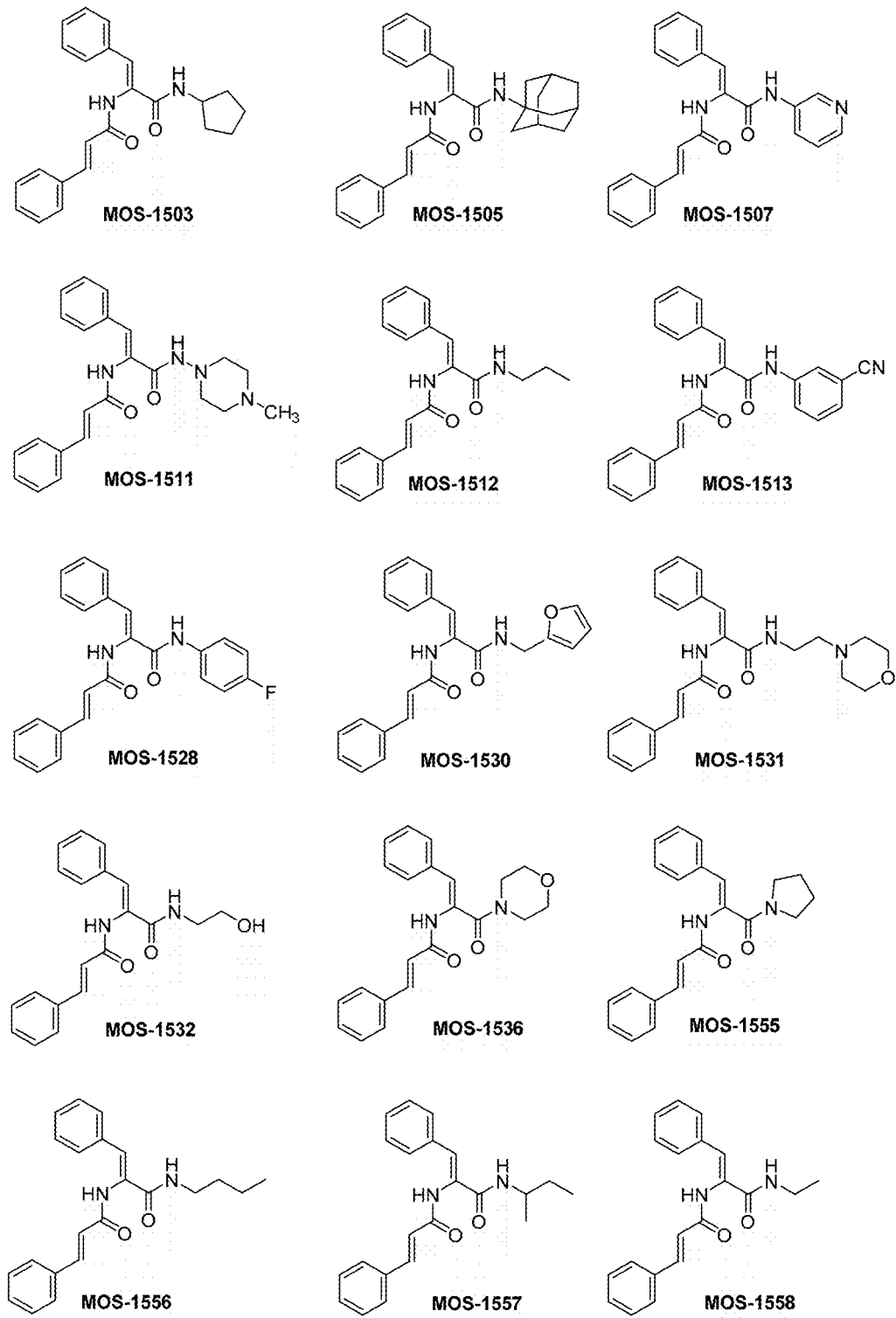
FIG. 2 illustrates compounds of the disclosure.
Figure 2:
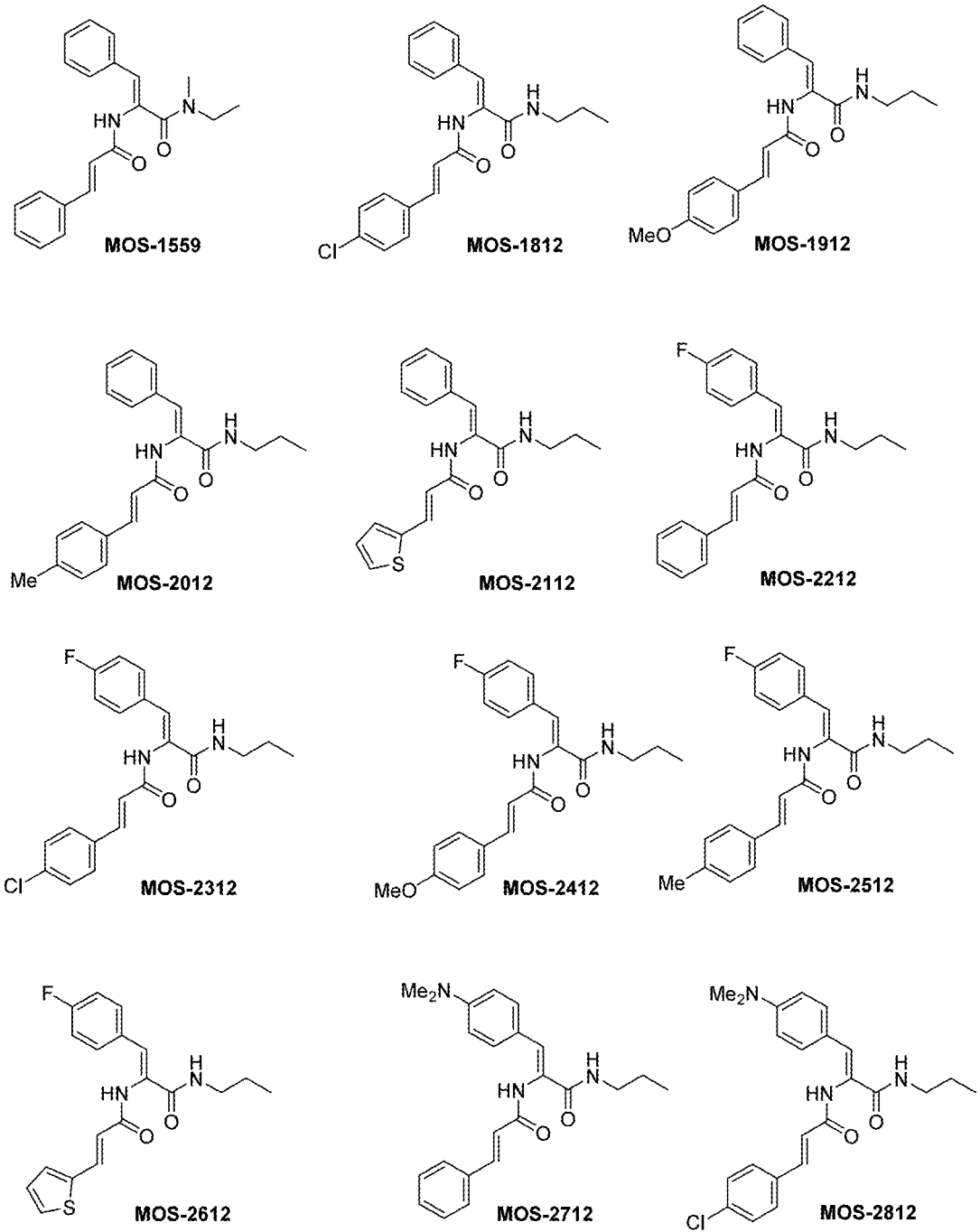
Figure 2:
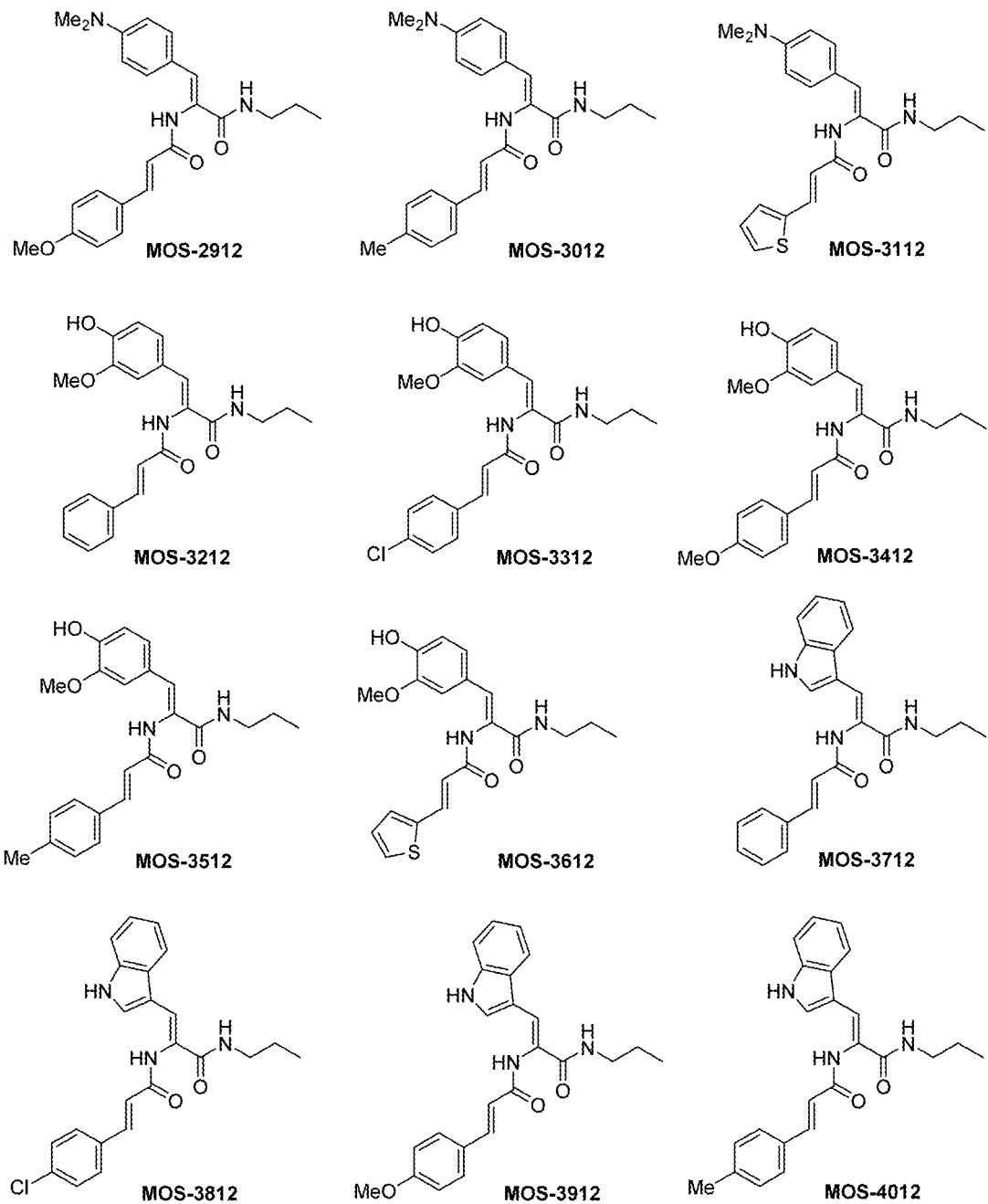
Figure 2:
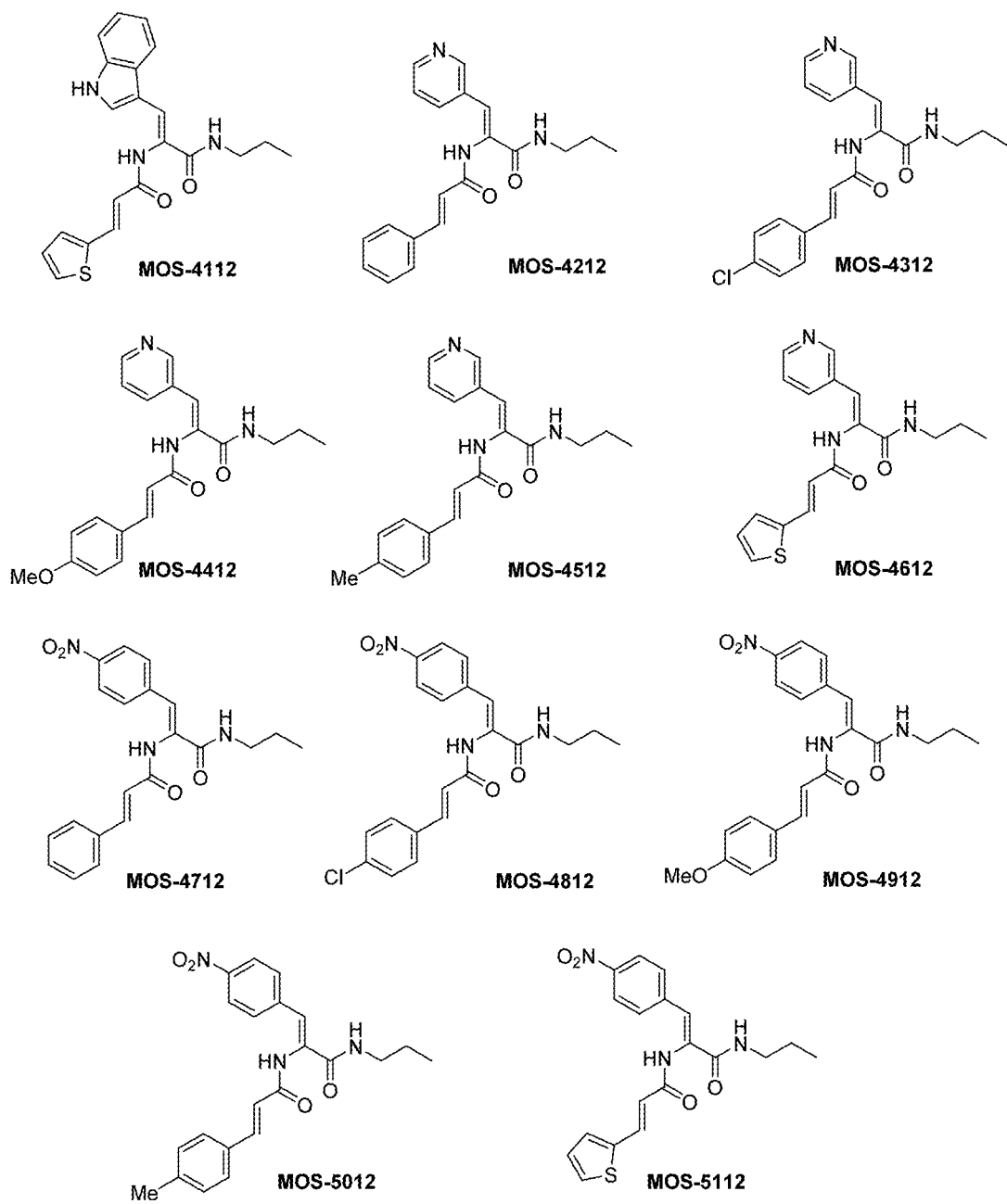

The synthetic pathway, described in FIG. 1C, utilized Erlenmeyer chemistry for azlactone synthesis. See El-Araby, M. E.; Omar, A. M.; Khayat, M. T.; Assiri, H. A.; Al-Abd, A. M., Molecular Mimics of Classic P-Glycoprotein Inhibitors as Multidrug Resistance Suppressors and Their Synergistic Effect on Paclitaxel. PLoS One 2017, 12 (1), e0168938, incorporated herein by reference in its entirety. In this scheme, non-commercially available cinnamic acid analogues 2 were prepared by condensation of the corresponding aldehyde (1, $R_1$CHO) with malonic acid. See Zhang, P.; Hu, H.-R.; Bian, S.-H.; Huang, Z.-H.; Chu, Y.; Ye, D.-Y., Design, synthesis and biological evaluation of benzothiazepinones (BTZs) as novel non-ATP competitive inhibitors of glycogen synthase kinase-3β (GSK-30). European journal of medicinal chemistry 2013, 61, 95-103, incorporated herein by reference in its entirety. After conversion to the cinnamoylglycine analogs (3), cyclocondensation was affected by their reaction with the corresponding aldehydes ($R_2$CHO) to afford the 2-arylvinyl-4-benzylidene-5-oxazolinone derivatives (azlactones, 4) under Erlenmeyer conditions. The key azlactone intermediate 4 was subsequently reacted with a variety of aliphatic and aromatic amines to furnish the final compounds (FIG. 2 and Table 1).

Generally, the aliphatic and benzylic amines reacted with the azlactone smoothly at room temperature in ethanol. The less reactive aromatic amines needed microwave heating in the presence of N,N-dimethylformamide (DMF) as a solvent.

Biological Screening

1. Antiproliferative Activities of bis-(3-arylpropenamide) Derivatives

Compounds in this study were tested against colorectal cancer cell line HCT-116, using sulforhodamine-B (SRB) assay. See Skehan, P.; Storeng, R.; Scudiero, D.; Monks, A.; McMahon, J.; Vistica, D.; Warren, J. T.; Bokesch, H.; Kenney, S.; Boyd, M. R., New colorimetric cytotoxicity assay for anticancer-drug screening. J Natl Cancer Inst 1990, 82 (13), 1107-12, incorporated herein by reference in its entirety. The subset of compounds (Codes MOS-1503 to 1559), having fixed phenyl groups at $R_1$ and $R_2$ positions (FIG. 2), demonstrated moderate to weak antiproliferative activities (Table 1). However, it was clear that compounds bearing hydrophobic aliphatic groups such as MOS-1505 and MOS-1512 are clearly favored in providing anticancer activities. Compounds having non-polar groups on $R_3$ position were more potent than those having polar groups such as MOS-1511, MOS-1532, MOS-1536. The N-aryl substituents were less advantageous in both potency and solubility. To zoom on N-aliphatic compounds, we observed that MOS-1505 N-(1-adamantyl) in this subset was the analogue with $IC_{50}$=14.7±0.3 µM against HCT116 colorectal cancer (CRC) cell lines. Unfortunately, MOS-1505 had poor solubility (ClogP6.08). Meanwhile, compound 1512 was slightly less active ($IC_{50}$=32.0±2.6 µM) but showed a better solubility profile (C Log P 4.48).

TABLE 1

Cytotoxic activities of final compounds on colon cancer cell lines

| Code | $R^1$ | $R^2$ | $R^3$ | HCT-116* | CACO-2* | HT-29* |
|---|---|---|---|---|---|---|
| 1503 | Ph | Ph | NH-cyclopentyl | 48.5 ± 3.1 | ND | ND |
| 1505 | Ph | Ph | NH-(1-adamantyl) | 14.7 ± 0.3 | ND | ND |
| 1507 | Ph | Ph | NH-(3-pyridyl) | >100 | ND | ND |
| 1508 | Ph | Ph | $NH_2$ | >100 | ND** | ND |
| 1511 | Ph | Ph | NH-(4-methyl-1-piperazinyl) | >100 | ND | ND |
| 1512 | Ph | Ph | NH—(n-Pr) | 32.0 ± 2.6 | 38.0 ± 0.87 | 35.5 ± 1.7 |
| 1513 | Ph | Ph | NH-(3-CN—Ph) | >100 | ND | ND |
| 1528 | Ph | Ph | NH-(4-F—Ph) | 91.9 ± 4.4 | ND | ND |
| 1530 | Ph | Ph | NH-furfuryl | >100 | ND | ND |
| 1531 | Ph | Ph | NH-(2-morpholinoethyl) | >100 | ND | ND |
| 1532 | Ph | Ph | NH-(2-hydroxyethyl) | >100 | ND | ND |
| 1536 | Ph | Ph | 4-morpholinyl | >100 | ND | ND |
| 1555 | Ph | Ph | 1-pyrrolidinyl | >100 | ND | ND |
| 1556 | Ph | Ph | NH—(m-Bu) | 67.2 ± 6.3 | ND | ND |
| 1557 | Ph | Ph | NH-sec-Bu) | 52.4 ± 7.1 | ND | ND |
| 1558 | Ph | Ph | NH—Et | >100 | ND | ND |
| 1559 | Ph | Ph | N(Me)Et | 28.8 ± 1.0 | ND | ND |
| 1812 | 4-ClPh | Ph | NH—(n-Pr) | 10.3 ± 0.34 | 10.7 ± 0.5 | 7.90 ± 0.43 |
| 1912 | 4-MeOPh | Ph | NH—(n-Pr) | 34.1 ± 1.8 | 18.5 ± 1.5 | 55.3 ± 3.2 |
| 2012 | 4-MePh | Ph | NH—(n-Pr) | 35.2 ± 0.54 | 12.7 ± 0.67 | 54.1 ± 0.42 |
| 2112 | 2-thienyl | Ph | NH—(n-Pr) | 43.0 ± 1.5 | 27.8 ± 1.3 | 43.2 ± 2.3 |
| 2212 | Ph | 4-FPh | NH—(n-Pr) | 15.2 ± 1.2 | 13.2 ± 1.0 | 7.20 ± 0.31 |
| 2312 | 4-ClPh | 4-FPh | NH—(n-Pr) | 3.80 ± 0.24 | 2.60 ± 0.233 | 4.00 ± 0.14 |
| 2412 | 4-MeOPh | 4-FPh | NH—(n-Pr) | 29.3 ± 1.2 | 45.73 ± 1.2 | 86.5 ± 2.9 |
| 2512 | 4-MePh | 4-FPh | NH—(n-Pr) | 6.70 ± 0.36 | 5.10 ± 0.17 | 11.80 ± 0.18 |
| 2612 | 2-thienyl | 4-FPh | NH—(n-Pr) | 17.3 ± 0.13 | 10.7 ± 0.68 | 7.68 ± 0.05 |
| 2712 | Ph | 4-($Me_2$N)Ph | NH—(n-Pr) | 6.95 ± 0.46 | 4.24 ± 0.09 | 6.8 ± 0.05 |
| 2812 | 4-ClPh | 4-($Me_2$N)Ph | NH—(n-Pr) | 20.7 ± 0.32 | 17.0 ± 0.8 | 9.52 ± 0.42 |
| 2912 | 4-MeOPh | 4-($Me_2$N)Ph | NH—(n-Pr) | 12.4 ± 0.25 | 15.3 ± 0.05 | 36.9 ± 0.25 |
| 3012 | 4-MePh | 4-($Me_2$N)Ph | NH—(n-Pr) | 22.1 ± 0.10 | 29.4 ± 0.08 | 39.6 ± 0.22 |
| 3112 | 2-thienyl | 4-($Me_2$N)Ph | NH—(n-Pr) | 11.6 ± 0.39 | 27.7 ± 3.7 | 66.5 ± 0.10 |

TABLE 1-continued

Cytotoxic activities of final compounds on colon cancer cell lines

| Code | $R^1$ | $R^2$ | $R^3$ | HCT-116* | CACO-2* | HT-29* |
|---|---|---|---|---|---|---|
| 3212 | Ph | 3-MeO-4-OHPh | NH—(n-Pr) | >100 | 6.32 ± 0.02 | 9.14 ± 0.23 |
| 3312 | 4-ClPh | 3-MeO-4-OHPh | NH—(n-Pr) | 37.8 ± 1.8 | 6.1 ± 0.44 | 5.4 ± 0.34 |
| 3412 | 4-MeOPh | 3-MeO-4-OHPh | NH—(n-Pr) | 38.4 ± 2.1 | 18.0 ± 1.2 | 48.6 ± 0.4 |
| 3512 | 4-MePh | 3-MeO-4-OHPh | NH—(n-Pr) | 26.3 ± 1.3 | 20.9 ± 1.0 | 15.1 ± 0.67 |
| 3612 | 2-thienyl | 3-MeO-4-OHPh | NH—(n-Pr) | 24.8 ± 1.4 | 28.3 ± 1.3 | 48.3 ± 1.9 |
| 3712 | Ph | 3-indolyl | NH—(n-Pr) | 1.65 ± 0.05 | 2.1 ± 0.03 | 2.36 ± 0.04 |
| 3812 | 4-ClPh | 3-indolyl | NH—(n-Pr) | 3.51 ± 0.21 | 3.35 ± 0.05 | 3.41 ± 0.03 |
| 3912 | 4-MeOPh | 3-indolyl | NH—(n-Pr) | 4.35 ± 0.29 | 2.07 ± 0.03 | 2.49 ± 0.04 |
| 4012 | 4-MePh | 3-indolyl | NH—(n-Pr) | 3.39 ± 0.10 | 2.3 ± 0.08 | 3.12 ± 0.06 |
| 4112 | 2-thienyl | 3-indolyl | NH—(n-Pr) | 2.85 ± 1.5 | 0.89 ± 0.04 | 1.65 ± 0.07 |
| 4212 | Ph | 3-pyridyl | NH—(n-Pr) | 73.0 ± 2.5 | 66.0 ± 2.2 | >100 |
| 4312 | 4-ClPh | 3-pyridyl | NH—(n-Pr) | 49.4 ± 1.9 | 47.3 ± 1.9 | 36.0 ± 1.7 |
| 4412 | 4-MeOPh | 3-pyridyl | NH—(n-Pr) | 52.1 ± 1.6 | 38.1 ± 2.0 | 72.7 ± 6.4 |
| 4512 | 4-MePh | 3-pyridyl | NH—(n-Pr) | >100 | 27.0 ± 1.8 | >100 |
| 4612 | 2-thienyl | 3-pyridyl | NH—(n-Pr) | >100 | 41.8 ± 1.4 | 68.8 ± 6.9 |
| 4712 | Ph | 4-NO$_2$Ph | NH—(n-Pr) | 17.3 ± 1.3 | 44.2 ± 2.7 | 23.2 ± 1.9 |
| 4812 | 4-ClPh | 4-NO$_2$Ph | NH—(n-Pr) | >100 | >100 | 36.9 ± 1.5 |
| 4912 | 4-MeOPh | 4-NO$_2$Ph | NH—(n-Pr) | >100 | >100 | 74.3 ± 3.6 |
| 5012 | 4-MePh | 4-NO$_2$Ph | NH—(n-Pr) | >100 | >100 | >100 |
| 5112 | 2-thienyl | 4-NO$_2$Ph | NH—(n-Pr) | >100 | 34.2 ± 1.1 | >100 |
| tCA | | | | 12.4 ± 1.2 | ND | ND |
| Doxo | | | | 0.6 ± 0.10 | 0.14 ± .01 | 0.3 ± 0.01 |

Figure 3A:
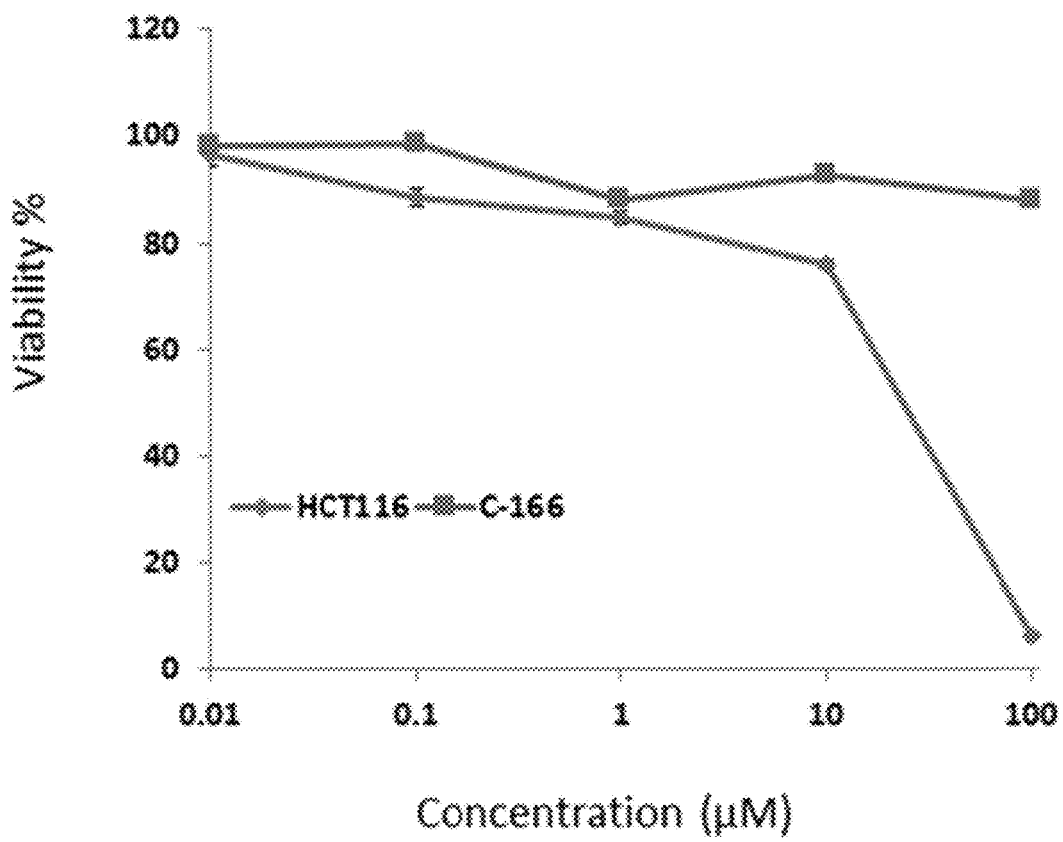
FIG. 3A is a graph illustrating the dose-response curve of compound 1512 on HCT-116 cell lines and C-166 cell line.

*IC$_{50}$ values in μM ± Standard Error of Means (SEM).
**ND, Not Determined.
tCA—trans-cinnamaldehyde
Doxo—doxorubicin MOS-1512 showed significantly low cancer cell resistance (R-value=8.2%), and high selectivity in killing cancer cells (HCT-116, Caco-2 and HT-29) versus highly proliferative normal cells (C-166 mouse skin fibroblasts) (FIG. 3A). See El-Araby, M. E.; Omar, A. M.; Khayat, M. T.; Assiri, H. A.; Al-Abd, A. M., Molecular Mimics of Classic P-Glycoprotein Inhibitors as Multidrug Resistance Suppressors and Their Synergistic Effect on Paclitaxel. PLoS One 2017, 12 (1), e0168938, incorporated herein by reference in its entirety.

Figure 3B:
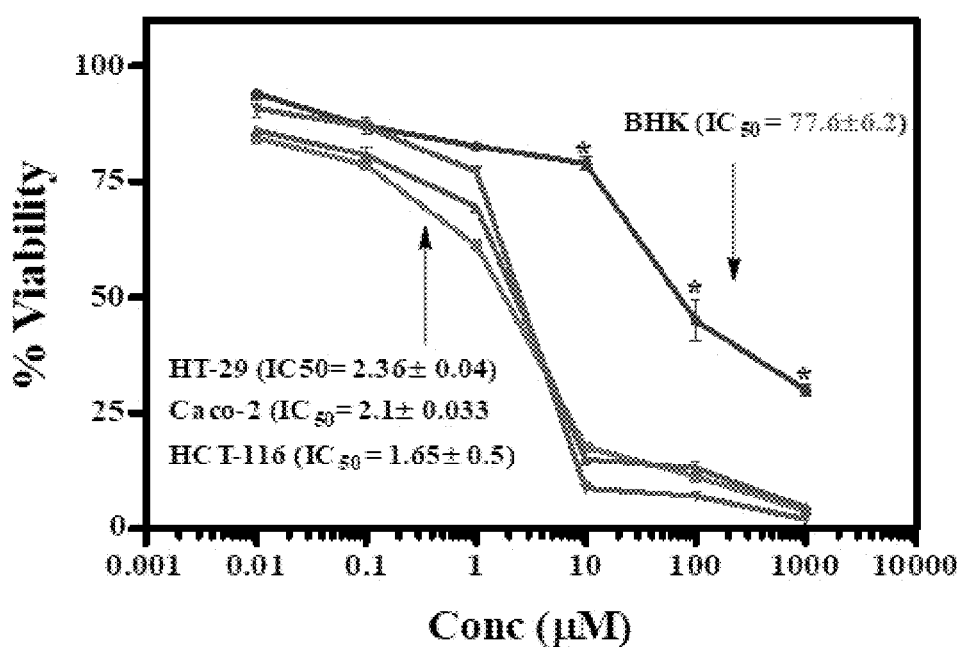
FIG. 3B is a graph illustrating the cytotoxic effect of 4112 against human colon adenocarcinoma cancer cells (HCT-116, Caco-2 and HT-29) vs. normal baby hamster kidney cells (BHK). All cells were exposed to different concentrations of 4112 for 72 h. The cell viability concentration curves were plotted, and the IC50 were determined. *denotes significance at P<0.001.

Based on the favorable pharmacologic and physicochemical properties of MOS-1512, it was selected as a new lead for the second subset of compounds (MOS-1812 to MOS-5112). The compounds in this series contained variable groups at $R^1$ and $R^2$ that were all tested against the three cancer cell lines (HCT-116, Caco-2 and HT-29). Some of the compounds showed high potencies similar to the reference drug doxorubicin (Table 1). For instance, MOS-2312, MOS-2812, MOS-3712, MOS-3812, MOS-3912, MOS-4012 and MOS-4112 demonstrated excellent cytotoxic activities against CRC cell lines (under 5 μM). For instance, compound MOS-4112 killed cancer cells HCT-116, Caco-2, and HT-29 cells in high potencies (IC$_{50}$ of 2.85±1.5, 0.89±0.04 and 1.65±0.07 μM, respectively) that are comparable to doxorubicin (0.6±0.1 0.14±0.05, and 0.3±0.01 μM, respectively). Compound MOS-4112 also had desirable selectivity against cancer cells versus baby hamster kidney (BHK) cell lines (IC$_{50}$=77.6±6.2 μM)(FIG. 3B). Also, potent compound 3712 is noteworthy, which exhibited IC$_{50}$ of 1.65±0.05, 2.1±0.03 M and 2.36±0.04 against HCT-116, Caco-2, and HT-29 cells, respectively.

2. Induction of Apoptosis in HCT-116 Cancer Cell Lines Upon Treatment with MOS-1512 and MOS-4112

Figure 4A:
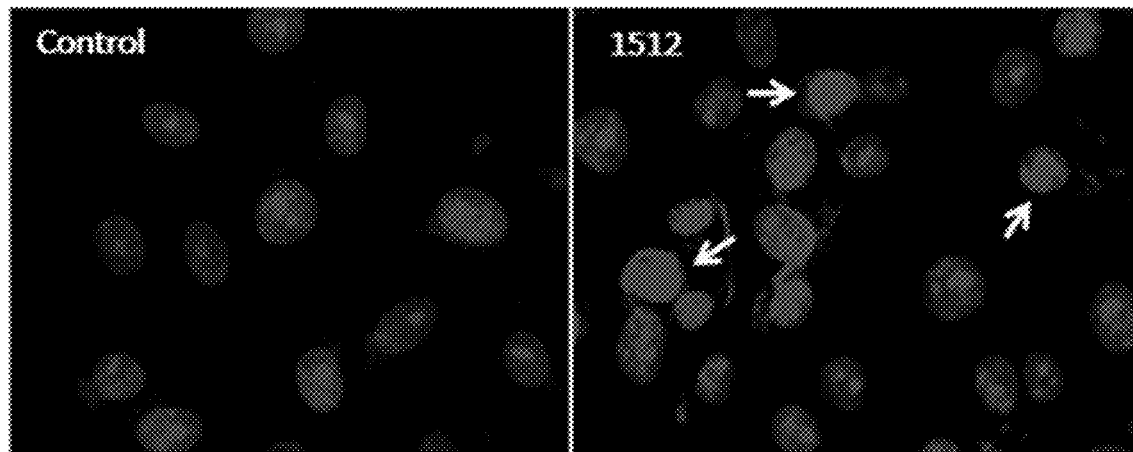
FIG. 4A illustrates the effect of 1512 at 32 μM ($IC_{50}$ concentration) on the nuclear structures of HCT-116 cells compared to control (untreated cells), where treated cells show nuclear condensation and fragmentation along with the condensed blue fluorescence of 4',6'-diamidino-2-phenylindole (DAPI), and arrows point to apoptotic cells.

Several assays were performed to determine the apoptotic effect of the early lead MOS-1512 as well as the potent derivative MOS-4112 on HCT-116 cells. First, the effect of 1512 on morphological changes of HCT-116 was monitored by staining the cell with the dye 4′,6′-diamidino-2-phenylindole (DAPI) after 48 hours of treatment with 32 μM of 1512 (IC$_{50}$ concentration). A very strong blue fluorescence was observed, indicative of increased cell membrane permeability and uptake of the dye, indicating that 1512 is able to disrupt the integrity of the cell to induce apoptosis (FIG. 4A). See Drutovic, D.; Chripkova, M.; Pilatova, M.; Kruzliak, P.; Perjesi, P.; Sarissky, M.; Lupi, M.; Damia, G.; Broggini, M.; Mojzis, J., Benzylidenetetralones, cyclic chalcone analogues, induce cell cycle arrest and apoptosis in HCT116 colorectal cancer cells. Tumour Biol 2014, 35 (10), 9967-75, incorporated herein by reference in its entirety.

Figure 4B:
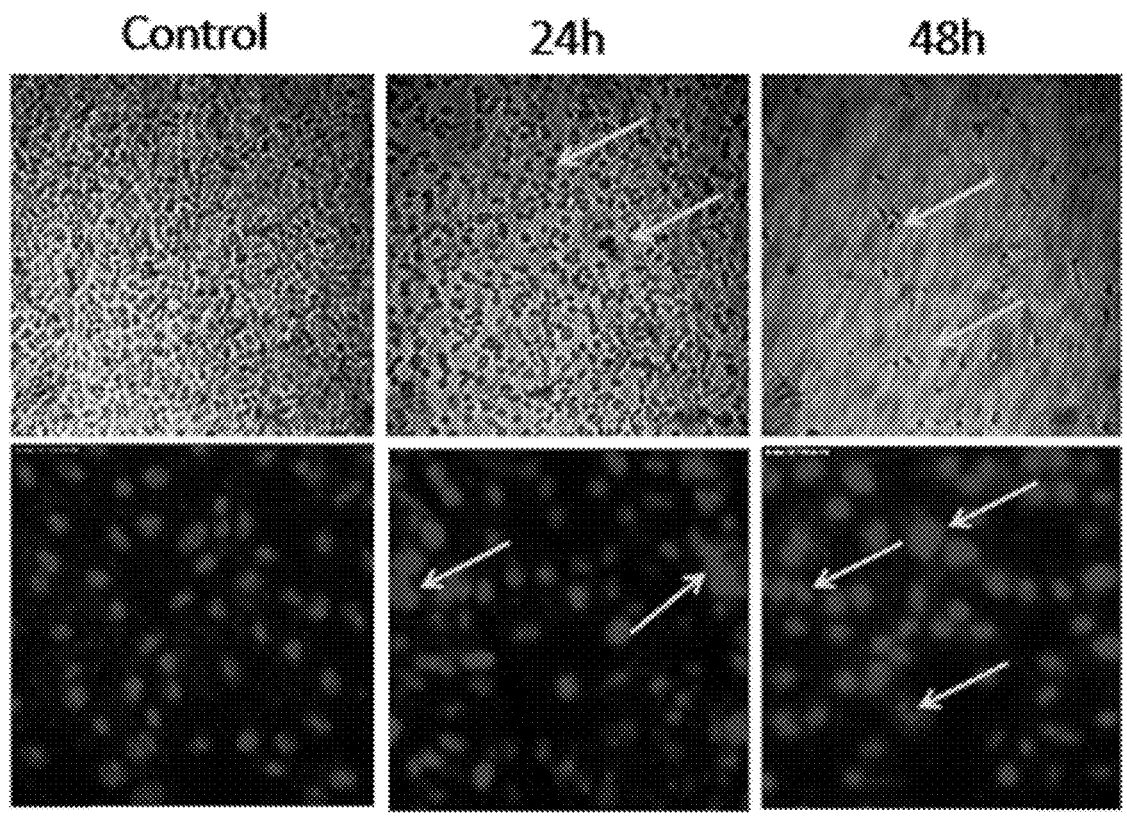
FIG. 4B illustrates morphological changes in HCT-116 cells following exposure to compound 4112, where the cells were left untreated (control) or treated with the $IC_{50}$ for 24 and 48 h—the pictures at top show the morphological changes examined under light microscope and the images at the bottom show the nuclei stained with DAPI and visualized under fluorescence microscope—arrows point to apoptotic cells.

DAPI staining test was also performed after incubation of HCT-116 cells with 4112 at 2.85 μM (the IC$_{50}$ value), and the results at 24 and 48 h shown in FIG. 4B. The percentage of cells with fragmented DNA and condensed nuclei greatly increased after 48 h compared to 24 h.

3. Cell Cycle Distribution Upon Treatment with MOS-4112

The effect of 4112 on HCT-116 cell cycle distribution was examined at the respective IC$_{50}$ concentrations for 24 h using a FACS Calibur flow cytometer. The exposure of the cells to 4112 led to a significant increase in the proportion of cells in pre-G1 phase (Up to 9-fold compared to the control). Accumulation of cells in pre-G1 phase, likely as a result of degradation or fragmentation of genetic material indicates a possible role for apoptosis through compound-induced growth inhibition.

Figure 5:
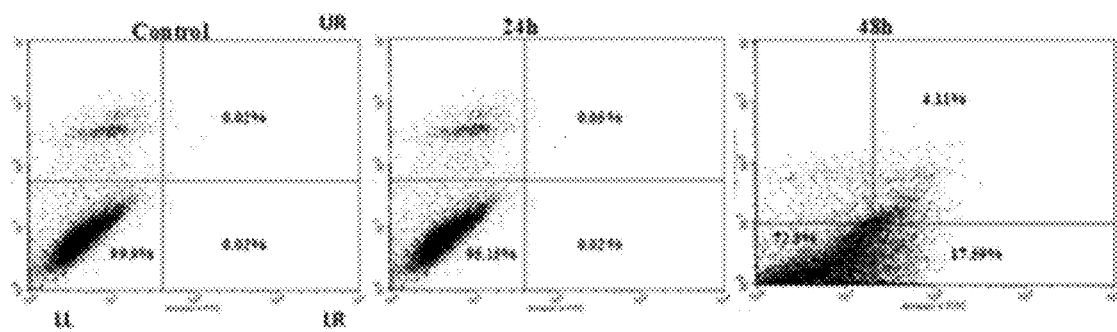
FIG. 5 illustrates the effect of 4112 on HCT-116 cell cycle progression: Key LL=viable cells, LR=early apoptotic cells, UR=late apoptosis.

In the subsequent similar experiment, 4112-treated HCT-116 cells were monitored for apoptotic changes at 24 h and 48 h. Cell cycle populations for the treated cells were determined by flow cytometry analysis after staining with Annexin V/Propidium iodide (FIG. 5) and revealed a large time-dependent increase in the percentage of HCT-116 apoptotic cells. At 24 hours, there was very little change in cell viability, while after 48 hours, viable cells have decreased to 72% (down from 99.9%). In the context, cell populations in both early and late apoptosis increased from almost zero to 17.5% and 4.1%, respectively.

4. Elevation of Oxidative Stress Indicators within HCT-116 Cells Upon Treatment with MOS-4112.

Figure 6:
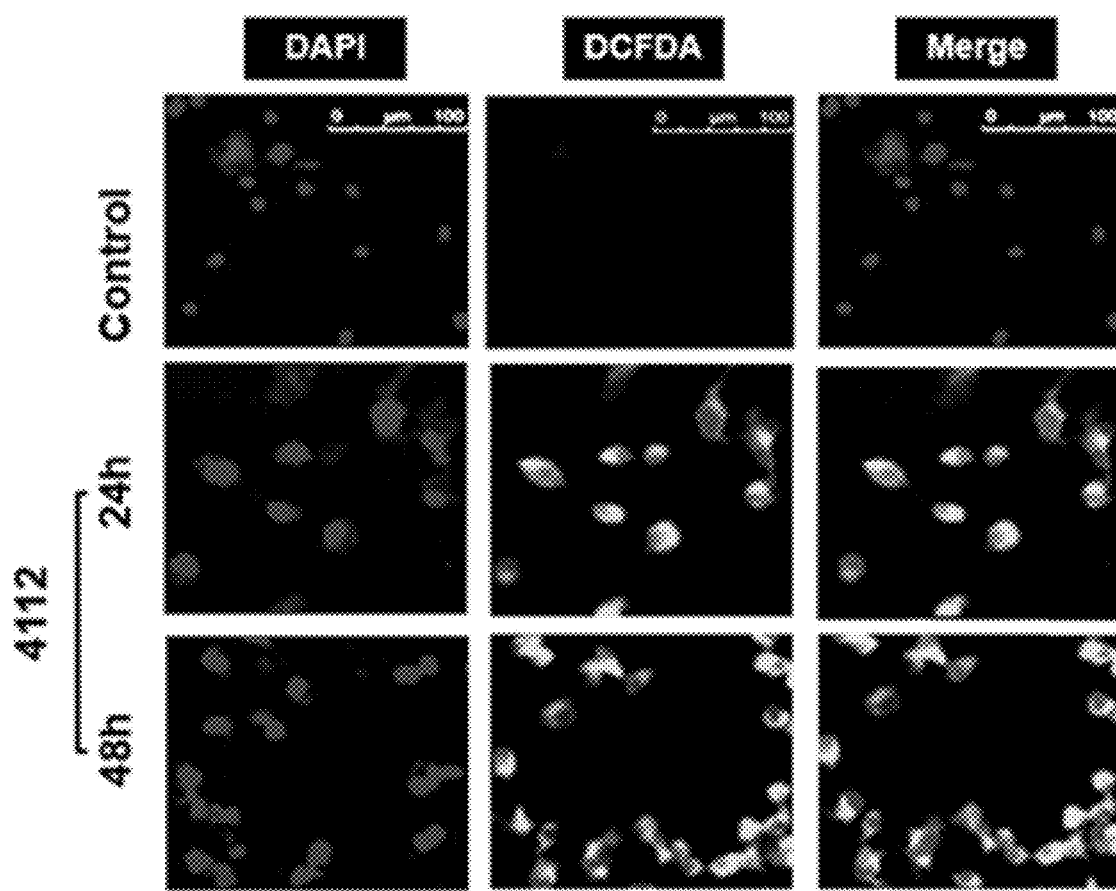
FIG. 6 illustrates the effect of 4112 on ROS production from HCT-116 cells using DCFDA staining, with green fluorescence (middle) representing DCFDA staining, while DAPI (left) was used as counter nuclear staining—scale bar of 100 μm.

The elevation of oxidative stress inside cancer cells, consequent to treatment with 4112, was investigated via monitoring ROS release over time (24 and 48 h). In this test, the 2′,7′-dichlorofluorescin diacetate (DCFDA) dye was used to detect various ROS species and emit green fluorescence. It was clear that compound MOS-4112 causes accumulation of ROS, compared to control (untreated cells) and it is proportional to the time of exposure (FIG. 6).

5. Inhibition of Cancer Stem Cell Proliferation in HT-29 Cancer Cell Lines Upon Treatment with MOS-3712 and MOS-4112

Figure 7:
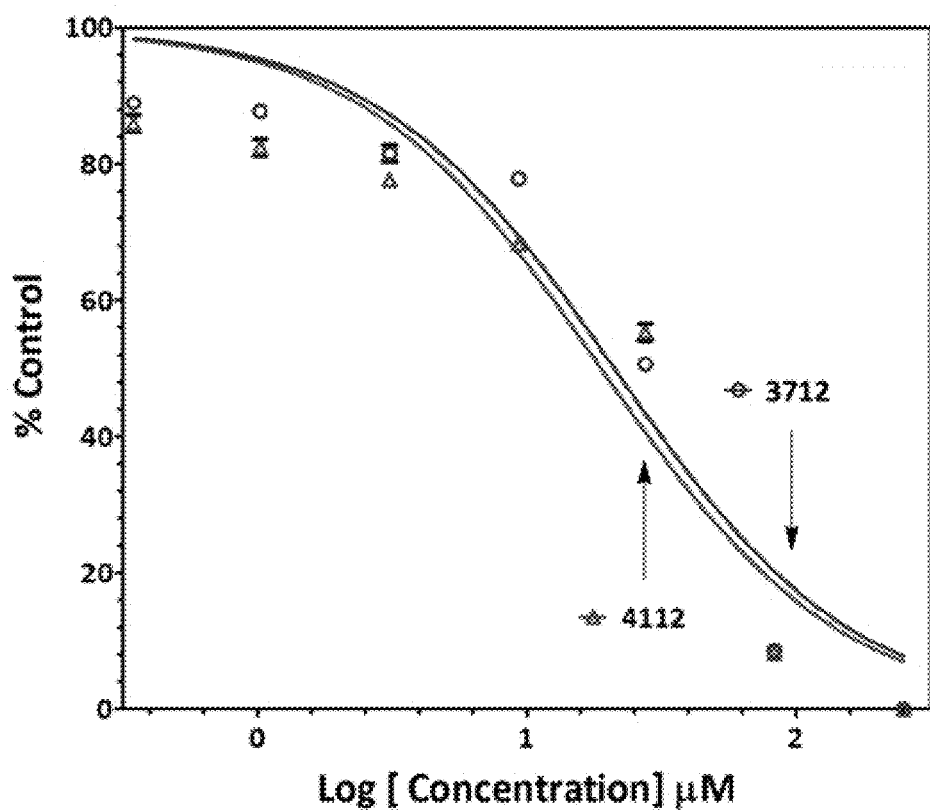
FIG. 7 is a graph illustrating the dose-response curve of HT-29 cell spheroids (expressed as % of vehicle treated cells) by increasing concentration of 3712 (circle) and 4112 (triangle).

Compound 4112 and another potent compound 3712 were also evaluated for their ability to inhibit cancer stem cell proliferation using a primary (1°) colonosphere formation assay. In this assay, HT-29 colon cancer cells were grown in low adhesion plates to form spheres as previously described. See Patel, N. J.; Karuturi, R.; Al-Horani, R. A.; Baranwal, S.; Patel, J.; Desai, U. R.; Patel, B. B., Synthetic, non-saccharide, glycosaminoglycan mimetics selectively target colon cancer stem cells. *ACS Chem Biol* 2014, 9 (8), 1826-33, incorporated herein by reference in its entirety. Wells treated with the inventive compounds were compared to vehicle treated cells for primary sphere growth inhibition after 5 days of incubation. Results, as illustrated in FIG. 7, showed a dose-dependent inhibition of colon cancer spheroids formation (>50 m). The $IC_{50}$ of the two compounds were 21.12±1.3 µM and 18.85±1.1 µM for 3712 and 4112 respectively, reflecting similar closeness in potency as in HT-29 monolayer cell line assay (2.36±0.04 µM and 1.65±0.07 µM, respectively). Of note, monolayer growth conditions are ideally suited for examining cellular proliferation, whereas spheroid growth conditions examine cancer stem cell growth and self-renewal properties. Hence, differential potency of the molecules in the two condition is reflective of their effects on two different phenotypes.

6. Lethal Dose Toxicity Test with Compounds MOS-1512, MOS-3712 and MOS-4112

Since compounds with electrophilic properties, e.g., MA are usually involved in a variety of toxic effects on mammalians, the general acute toxicity of 1512, 3712 and 4112 was investigated by determining the in vivo lethal dose ($LD_{50}$) according to the Globally Harmonized Classification System (GHS) and following the Organization for Economic Cooperation and Development (OECD) guideline 423 (modified, adopted Mar. 23, 2006). As observed in the cellular assay, the compound safety was confirmed, as the $LD_{50}$ for all compounds were between 2000-5000 mg/kg (Category 5). See Spielmann, H.; Genschow, E.; Liebsch, M.; Halle, W., Determination of the starting dose for acute oral toxicity (LD50) testing in the up and down procedure (UDP) from cytotoxicity data. *ATLA* 1999, 27 (6), 957-966, incorporated herein by reference in its entirety.

Brief Summary of Results

The compounds showed selective toxicity against cancer cell lines (in particular colorectal cancer cells) and cancer stem cells (CSC) over noncancerous cells (C-166 and BHK), low animal toxicity, and a clear cell death mechanism. The two most potent compounds, 3712 and 4112 exhibited significant anti-proliferative effects on colorectal cancer cell lines CaCo-2, HCT-116 and HT-29.

Experimental

All melting points were uncorrected and measured using the capillary melting point instrument B1 9100 (Barnstead Electrothermal, UK). Infrared spectra were recorded on a Thermo Scientific Niccolet iS10 FT-IR Spectrometer (King Fahd Center for Medical Research, King Abdulaziz University, Jeddah, Saudi Arabia). Only the important IR stretching bands were listed, including NH, OH, CH, C=O, C=N and/or C=C. In FT-IR, all samples were measured neat. $^1$H NMR spectra were determined on an AVANCE-III 600 MHz and AVANCE-III HD 850 MHz spectrometers (Bruker, Germany), and chemical shifts are expressed as ppm against TMS as an internal reference (King Fahd Center for Medical Research and Faculty of Science, King Abdulaziz University, Jeddah, Saudi Arabia). LC/MS analyses were performed on an Agilent 6320 Ion Trap HPLC-ESI-MS/DAD (Santa Clara, Calif., USA) with the following settings: The analytes were separated using an Macherey-Nagel Nucleodur-C18 column (150 mm length×4.6 mm i.d., 5 µm) (Macherey-Nagel GMBH & Co. KG, Duren, Germany). Mobile phase; isocratic elution using a mixture of isopropanol and 0.01M ammonium acetate in water (65:35, v/v). The flow rate was 0.4 mL/min; total run time=20 min. Purities are reported according to percentage of Peak Areas at wavelength 280 nm. High-resolution mass spectrometry (HRMS) was performed in the Faculty of Science, King Abdulaziz University on Impact II™ Q-TOF spectrometer (Bruker, Germany). Microanalyses were operated using Vario, an Elmentar apparatus (Shimadzu, Japan), Organic Microanalysis Unit, Cairo University, Giza, Egypt. Column chromatography was performed on a silica gel 60 (particle size 0.06 mm-0.20 mm).

Chemical Synthesis

The previously reported intermediate azlactone 4a (see FIG. 1C, intermediate 4, where $R^1$ and $R^2$ are phenyl, i.e., 4-((Z)-benzylidene)-2-((E)-styryl)oxazol-5(4H)-one) (Fahmy, A.; Orabi, M., Reactions of 4-arylidene-2-styryl-5 (4)-oxazolones and related compounds, *Indian Journal of Chemistry* 1972, 10 (10), 961-964), was prepared according to procedures mentioned below, and their physical and spectral properties were confirmed. Purity of compounds were first assessed qualitatively using Thin Layer Chromatography (TLC), $^1$H NMR and quantitatively using LC/MS (UV detection). The compounds were screened only if purity was confirmed to be above 95%. The compounds subjected to all biological screenings were used as a single Z isomer as detected by TLC, LC/MS and NMR.

(Z)-2-cinnamamido-N-cyclopentyl-3-phenylacrylamide (1503)

Azlactone 4a (10 mmol, 2.773 g) was dissolved in 50 mL ethanol, cyclopentylamine (20 mmol, 2.0 mL) was then added, and the mixture was stirred for 2 h. The solvent was removed under reduced pressure. The residue was treated with ice-cooled dilute HCl resulting in precipitation of a off-white solid product. The crude product was purified by crystallization from ethanol. The purified product 1503 was an off-white solid, (0.45 g, 60%), Mp 239° C. $^1$H NMR (600 MHz, acetone-$d_6$) $\delta_H$ ppm 8.85 (s, 1H), 7.59-7.67 (m, 2H), 7.55 (d, J=7.53 Hz, 2H), 7.40-7.47 (m, 3H), 7.37 (t, J=7.53 Hz, 2H), 7.28-7.32 (m, 1H), 7.09 (br. s., 1H), 6.96 (d, J=15.81 Hz, 1H), 4.24-4.32 (m, 1H), 1.90-1.98 (m, 2H), 1.71 (br. s., 2H), 1.54-1.62 (m, 4H).

(Z)—N-(1-adamantanyl)-2-cinnamamido-3-phenylacrylamide (1505)

This compound was prepared according to the procedure described for the synthesis of 1503 starting from azlactone 4a (2 mmol, 0.554 g) and 1-aminoadamantane (2 mmol, 0.308 g). The product 1505 was a white solid (0.75 g, 88%), Mp 272° C. H NMR (600 MHz, acetone-d$_6$) δ$_H$ ppm 8.86 (s, 1H), 7.62-7.68 (m, 3H), 7.54 (d, J=7.53 Hz, 2H), 7.40-7.47 (m, 3H), 7.37 (t, J=7.53 Hz, 2H), 7.27-7.32 (m, 1H), 7.05 (s, 1H), 6.98 (d, J=15.43 Hz, 1 H),2.17 (m, 1H), 2.13 (br. s., 6H), 2.00-2.03 (m, 1H), 1.95-1.97 (m, 1H), 1.73 (br. s., 6H), 1.57-1.59 (m, 1H).

(Z)-2-[(E)-cinnamamido]-3-phenyl-N-(3-pyridyl)acrylamide (1507)

In the reaction tube of a microwave reactor (SynthLab), azlactone 4a (2 mmol, 0.554 g) and 3-aminopyridine (2 mmol, 0.188 g) were mixed with 5 mL DMF. The reaction was heated to 200° C. while stirring in a Milestone microwave reactor for 10 min. After cooling, the mixture was added slowly to ice-cold water. The resulting solid was collected by filtration, washed with water and purified using silica gel chromatography (petroleum ether/dichloromethane (DCM)/MeOH, gradient) to give 1507 as a white solid (0.206 g, 30%), Mp>250° C. (dec.). $^1$H NMR (600 MHz, Acetone-d$_6$) δ$_H$ ppm 9.79 (1H, br s), 9.31 (1H, br s), 8.91 (1H, s), 8.31 (1H, dd, J=6.52, 1.13 Hz), 8.27 (1H, d, J=8.66 Hz), 7.69-7.61 (5H, m), 7.48-7.39 (5H, m), 7.38-7.32 (2H, m), 7.21 (1H, s), 7.03 (1H, d, J=15.81 Hz), LC-MS (ESI), RT=7.4 min, m/z 370.2 [M+H]$^+$.

N—[(Z)-3-amino-3-oxo-1-phenylprop-1-en-2-yl]-(E)-cinnamamide (1508)

Azlactone 4a (2 mmol, 0.554 g) was stirred in 5 mL solution of ammonia (2M) in ethanol for 2 h. The product was precipitated as white powder which was filtered, washed with water several times followed by ethanol and dichloromethane. Crystallization from aqueous methanol provided a white solid of 1508 Mp>250° C. (dec.) H NMR (DMSO-d6) d$_H$ ppm 10.11 (br. s., 1H), 7.75 (br. s., 1H), 7.61 (d, J=6.78 Hz, 2H), 7.55 (d, j=7.53 Hz, 2H), 7.35-7.53 (m, 6H), 7.31 (d, J=7.15 Hz, 1H), 7.16 (br. s., 1H), 7.10 (s, 1H), 6.91 (d, J=15.81 Hz, 1H).

(Z)-2-[(E)-cinnamamido]-N-(4-methyl-1-piperazinyl)-3-phenyl-acrylamide (1511)

This compound was prepared according to the procedure described for the synthesis of 1503 starting from azlactone 4a (2 mmol, 0.554 g) and 1-amino-4-methylpiperazine (4 mmol, 0.49 mL). The product 1511 was an off-white power, (305 mg, 39%), Mp. 190° C.; 1H NMR (600 MHz, DMSO-d6) δH ppm 9.83 (s, 1H), 9.58 (s, 1H), 7.62 (d, J=7.53 Hz, 2H), 7.54-7.58 (m, J=7.91 Hz, 2H), 7.52 (d, J=15.81 Hz, 1H), 7.44-7.48 (m, 2H), 7.39-7.44 (m, 3H), 7.30-7.35 (m, 1H), 6.91 (d, J=15.81 Hz, 1H), 6.75 (br. s., 1H), 3.43 (br. s., 2H), 3.14-3.22 (m, 4H), 3.10 (br. s., 2H), 2.77 (br. s., 3H).

(Z)-2-[(E)-cinnamamido]-3-phenyl-N-propylacrylamide (1512)

This compound was prepared according to the procedure described for the synthesis of 1503 starting from azlactone 4a (2 mmol, 0.554 g) and n-propylamine (2 mmol, 0.166 mL). The product 1512 was a white solid (542 mg, 81%), Mp 207° C. $^1$H NMR (850 MHz, DMSO-d$_6$) δ$_H$ 9.69 (s, 1H), 8.12 (t, J=5.97 Hz, 1H), 7.62 (d, J=7.78 Hz, 2H), 7.55 (d, J=7.78 Hz, 2H), 7.50 (d, J=16.09 Hz, 1H), 7.46 (t, J=7.79 Hz, 2H), 7.42 (t, J=7.79 Hz, 1H), 7.38 (t, J=7.79 Hz, 2H), 7.31 (t, J=7.79 Hz, 1H), 7.00 (s, 1H), 6.87 (d, J=16.09 Hz, 1H), 3.12 (q, J=6.75 Hz, 2H), 1.49 (dt, J=7.27 and 6.9 Hz, 2H), 0.88 (t, J=7.53 Hz, 3H); $^{13}$C NMR (214 MHz, DMSO-d$_6$) δ 165.1, 164.7, 140.0, 134.8, 134.3, 130.5, 129.9, 129.4, 129.1, 128.6, 128.6, 127.8, 126.9, 121.6, 41.0, 39.8, 39.7, 39.6, 39.5, 39.4, 39.3, 39.2, 22.3, 11.5; LC-MS (ESI), RT=3.6 min, m/z 335.1 [M+H]$^+$. Anal. Calcd for (C$_{21}$H$_{22}$N$_2$O$_2$): C, 75.42; H, 6.63; N, 8.38 Found C, 75.37; H, 6.59; N, 8.29.

(Z)-2-[(E)-cinnamamido]-N-(3-cyanophenyl)-3-phenyl-acrylamide (1513)

This compound was prepared according to the procedure used in the synthesis of compound 1503 starting from the azlactone 4a (2 mmol, 0.554 g) and 3-aminobenzonitrile (2 mmol, 0.236 g). The product 1513 as a white solid (0.352 g, 47%), Mp 235-237° C. $^1$H NMR (600 MHz, DMSO-d$_6$) δ$_H$ 10.52 (1H, br s), 10.05 (1H, br s), 8.19 (s, 1H), 8.01 (1H, d, J=7.78 Hz), 7.66-7.60 (m, 4H), 7.58-7.50 (m, 3H), 7.48-7.40 (m, 5H), 7.36 (m, 1H), 6.98 (s, 1H), 6.93 (1H, d, J=16.09 Hz).

(Z)-2-[(E)-cinnamamido]-N-(4-fluorophenyl)-3-phenylacrylamide (1528)

This compound was prepared according to the procedure used in the synthesis of compound 1503 starting from the azlactone 4a (2 mmol, 0.554 g) and 4-fluoroaniline (2 mmol, 0.192 mL). The final compound 1528 was collected as a white solid (0.471 g, 65%), Mp 200° C. $^1$H NMR (600 MHz, DMSO-d$_6$) δ$_H$ ppm 10.18 (1H, s), 9.92 (1H, s), 7.74-7.68 (2H, m), 7.62 (4H, t, J=6.96 Hz), 7.51 (1H, d, J=15.81 Hz), 7.48-7.39 (7H, m), 7.35 (1H, m), 7.17 (2H, m), 6.96 (s, 1H), 6.91 (1H, d, J=15.81 Hz); IR (FT-IR, cm$^{-1}$): 3214.5, 3059.3, 2979.2, 1647.5, 1614.2, 1505.4.

(Z)-2-[(E)-cinnamamido]-N-(2-furylmethyl)-3-phenyl-acrylamide (1530)

This compound was prepared according to the procedure described for the synthesis of 1503 starting from azlactone 4a (2 mmol, 0.554 g) and furfurylamine (2 mmol, 0.176 mL). The product 1530 was an off-white solid, (0.45 g, 60%), Mp 198-199° C. $^1$H NMR (600 MHz, DMSO-d$_6$) δ$_H$ 9.76 (1H, s), 8.62 (1H, t, J=5.8 Hz), 7.63 (2H, m), 7.55-7.60 (3H, m), 7.53 (1H, d, J=15.8 Hz), 7.46 (2H, m), 7.41 (1H, d, J 7.5 Hz), & 0.39 (2H, t, J 7.7 Hz), 7.32 (1H, m), 7.10 (1H, s), 6.88 (1H, d, J=15.8 Hz), 6.41 (1H, m), 6.32 (1H, m), 4.37 (2H, d, J=5.65 Hz); IR (FT-IR, cm$^{-1}$): 3394.3, 3065.2, 2955.9, 1705.5, 1625.7, 1508.2; LC-MS (ESI) RT=3.6 min, m % z 373.1[M+H]$^+$. Anal. Calcd for (C$_{23}$H$_{20}$N$_2$O$_3$): C, 74.18; H, 5.41; N, 7.52; Found C, 73.79; H, 5.08; N, 7.65.

(Z)-2-[(E)-cinnamamido]-N-(2-morpholinoethyl)-3-phenyl-acrylamide (1531)

This compound was prepared according to the procedure described for the synthesis of 1503 starting from azlactone 4a (2 mmol, 0.554 g) and 2-(4-morpholinyl)ethylamine (5 mmol, 0.65 mL). The product 1531 was an off-white solid, (0.61 g, 75%), Mp 169° C. $^1$H NMR (600 MHz, DMSO-d$_6$) δ$_H$ 9.74 (s, 1H), 7.96 (br s, 1H), 7.63 (d, J=7.15 Hz, 2H), 7.56 (d, J=7.53 Hz, 2H), 7.53 (d, J=15.81 Hz, 1H), 7.37-7.50 (m, 5H), 7.29-7.36 (m, 1H), 7.07 (s, 1H), 6.88 (d, J=16.19 Hz, 1H), 3.52-3.61 (m, 4H), 3.25-3.32 (m, 2H), 2.37-2.47 (m, 6H). LC-MS (ESI) RT=3.7 min, m/z 406.2 [M+H]$^+$.

(Z)-2-[(E)-cinnamamido]-N-(2-hydroxyethyl)-3-phenyl-acrylamide (1532)

Ethanolamine (10 mmol, 0.6 m) was placed in a conical flask and stirred, added Azlactone 4a (2 mmol, 0.554 g) portion wise while stirring. Reaction was left to go to completion for two hours. The mixture was treated with ice-cooled water containing 10 mL 1M HCl and the precipitated product was collected by filtration. Purification was carried out by crystallization in ethanol to furnish 1532 as a white fluffy solid (0.43 g, 63.9%), Mp 204° C., $^1$H NMR (850 MHz, DMSO-$d_6$) $\delta_H$ 9.72 (s, 1H), 8.06 (t, J=5.71 Hz, 1H), 7.62 (d, J=7.79 Hz, 2H), 7.55 (d, J=7.79 Hz, 2H), 7.51 (d, J=15.57 Hz, 1H), 7.49-7.44 (m, 2H), 7.42 (d, J=7.27 Hz, 1H), 7.39 (t, J=7.79 Hz, 2H), 7.29-7.34 (m, 1H), 6.88 (d, J=16.09 Hz, 1H) 7.05 (s, 1H), 4.65 (t, J=5.71 Hz, 1H), 3.47 (q, J=5.88 Hz, 2H), 3.24 (q, J=6.23 Hz, 2H). LC-MS (ESI) RT=3.48 min, m/z 337.0 [M+H]$^+$.

N—[(Z)-3-morpholino-3-oxo-1-phenylprop-1-en-2-yl]cinnamamide (1536)

This compound was prepared according to the procedure described for the synthesis of 1503 starting from azlactone 4a (2 mmol, 0.554 g) and morpholine (4 mmol, 0.39 mL). The product 1536 was an off-white power, (0.514 g, 71%), Mp. 185° C.; 1H NMR (600 MHz, DMSO-d6) $\delta_H$ 10.07 (s, 1H), 7.56-7.63 (m, 6H), 7.40-7.48 (m, 6H), 7.27-7.36 (m, 1H), 6.93 (d, J=15.81 Hz, 1H), 6.19 (s, 1H), 3.53 (br. s., 4H), 3.35 (br. s., 4H).

N—[(Z)-3-(1-pyyrrolidinyl)-3-oxo-1-phenylprop-1-en-2-yl]cinnamamide (1555)

This compound was prepared according to the procedure described for the synthesis of 1503 starting from azlactone 4a (2 mmol, 0.554 g) and pyrrolidine (2 mmol, 0.165 mL). The product 1555 was a white power, (0.580 g, 84%), Mp. 194° C.; $^1$H NMR (600 MHz, DMSO-$d_6$) $\delta_H$ 10.00 (s, 1H), 7.52-7.64 (m, 6H), 7.37-7.49 (m, 6H), 7.30-7.33 (m, 1H), 6.91 (d, J=15.81 Hz, 1H), 6.32 (s, 1H), 3.58 (t, J=6.02 Hz, 2H), 3.37 (t, J=6.59 Hz, 2H), 1.82-1.87 (m, 4H).

(Z)—N-(n-butyl)-2-[(E)-cinnamamido]-3-phenylacrylamide (1556)

This compound was prepared according to the procedure described for the synthesis of 1503 starting from azlactone 4a (2 mmol, 0.554 g) and n-butylamine (2 mmol, 0.176 mL). The product 1556 was an off-white solid, (0.45 g, 60%), Mp 198-199° C. $^1$H NMR (600 MHz, DMSO-$d_6$) $\delta_H$ 9.69 (s, 1H), 8.10 (t, J=5.83 Hz, 1H), 7.62 (d, J=7.15 Hz, 2H), 7.56 (d, J=7.53 Hz, 2H), 7.51 (d, J=15.81 Hz, 1H), 7.44-7.48 (m, 2H), 7.36-7.44 (m, 3H), 7.31 (t, J=7.34 Hz, 1H), 7.01 (s, 1H), 6.88 (d, J=16.19 Hz, 1H), 3.17 (q, J=6.78 Hz, 2H), 1.47 (quin, J=7.25 Hz, 2H), 1.32 (sxt, J=7.38 Hz, 2H), 0.90 (t, J=7.34 Hz, 3H).

(Z)—N-(sec-butyl)-2-cinnamamido-3-phenylacrylamide (1557)

This compound was prepared according to the procedure described for the synthesis of 1503 starting from azlactone 4a (2 mmol, 0.554 g) and sec-butylamine (2 mmol, 0.202 mL). The product 1557 was an off-white solid, (0.51 g, 73%), Mp 229° C. $^1$H NMR (600 MHz, DMSO-$d_6$) $\delta_H$ ppm 9.66 (s, 1H), 7.84 (d, J=8.66 Hz, 1H), 7.62 (t, J=7.15 Hz, 2H), 7.56 (d, J=7.91 Hz, 2H), 7.52 (d, J=15.81 Hz, 1H), 7.49-7.41 (m, 3H), 7.39 (t, J=7.72 Hz, 2H), 7.34-7.28 (m, 1H), 6.94-6.86 (m, 2H), 3.81 (dt, J=13.93, 7.34 Hz, 1H), 1.39-1.59 (m, 2H), 1.11 (d, J 6.78 Hz, 3H), 0.84-0.93 (m, 3H).

(Z)-2-[(E)-cinnamamido]-N-ethyl-3-phenylacrylamide (1558)

This compound was prepared according to the procedure described for the synthesis of 1503 starting from azlactone 4a (2 mmol, 0.554 g) and ethylamine (1 mL of 40% in water). The product 1558 was an off-white solid, (0.39 g, 61%), Mp 190° C. $^1$H NMR (600 MHz, DMSO-$d_6$) $\delta_H$ ppm 1.08 (t, J=7.34 Hz, 3H) 3.19 (dd, J=7.15, 6.02 Hz, 2H) 6.87 (d, J=15.81 Hz, 1H) 7.02 (s, 1H) 7.28-7.33 (m, 1H) 7.39 (t, J=7.72 Hz, 2H) 7.43 (d, J=7.15 Hz, 1H) 7.44-7.49 (m, 2H) 7.51 (d, J=16.19 Hz, 1H) 7.55 (d, J=7.53 Hz, 2H) 7.62 (d, J=7.15 Hz, 2H) 8.11-8.17 (m, 1H), 9.68 (s, 1H).

(Z)-2-cinnamamido-N-ethyl-N-methyl-3-phenylacrylamide (1559)

This compound was prepared according to the procedure described for the synthesis of 1503 starting from azlactone 4a (2 mmol, 0.554 g) and N-ethyl-N-Methylamine (2 mmol, 0.171 mL). The product 1559 was a white solid (0.61 g, 91%), Mp 169° C. $^1$H NMR (600 MHz, DMSO-$d_6$) $\delta_H$ ppm 10.01 (br. s., 1H), 7.61 (d, J=7.15 Hz, 2H), 7.52-7.59 (m, 3H), 7.37-7.49 (m, 5H), 7.27-7.34 (m, 1H), 6.94 (d, J=15.81 Hz, 1H), 6.09-6.20 (s, 1H), 3.08 (s, 3H), 2.85 (q, J=7.1 Hz, 2H), 1.12 (t, J=6.9 Hz, 3H).

Ethyl (Z)-2-cinnamamido-3-phenylacrylate (15EE)

The azlactone 4a (2 mmol, 0.554 g) was heated under reflux in absolute ethanol in presence of 5 mg of 4-dimethylaminopyridine (DMAP) for 3 hours. The solvent was removed by vacuum evaporation and residue was partitioned between dichloromethane and 1M HCl. The organic layer was washed with water then brine, dried with sodium sulfated and evaporated under vacuum to give the product 15EE (ethyl ester) as an off-white solid (0.51 g, 79%), Mp 153° C. $^1$H NMR (600 MHz, CDCl$_3$) $\delta_H$ 8.97 (br. s., 1H), 7.62-7.69 (m, 5H), 7.34-7.50 (m, 6H), 7.30 (s, 1H), 6.99 (d, J=15.81 Hz, 1H), 4.27 (q, J=7.03 Hz, 2H), 1.31 (t, J=7.15 Hz, 3H).

(Z)—N-(n-propyl)-2-(benzoylamino)-3-phenylacrylamide (1612)

This compound was prepared according to the procedure described for the synthesis of 1503 starting from 4-benzylidene-2-phenyloxazol-5(4H)-one (0.25 g, 1 mmol) and n-propylamine (0.16 mL, 2 mmol). The product 1612 was an off-white solid, (0.27 g, 81%), Mp 169° C. $^1$H NMR (850 MHz, DMSO-$d_6$) $\delta_H$ 10.17 (br s, 1H), 8.32 (br s, 1H), 8.00 (d, J=7.27 Hz, 1H), 7.88-7.86 (m, 1H), 7.61-7.55 (m, 1H), 7.53-7.47 (m, 1H), 7.40 (d, J=8.30 Hz, 1H), 7.20-7.28 (m, 2H), 3.11 (m, J=6.75 Hz, 2H), 1.47 (m, 1H), 0.86 (t, J=7.27 Hz, 3H). LC-MS (ESI) RT=4.52 min, m/z 309.0 [M+H]$^+$.

(2Z,4E)-2-cinnamamido-5-phenyl-N-propylpenta-2,4-dienamide (1712)

Compound 1712 (El-Araby, M. E.; Omar, A. M.; Khayat, M. T.; Assiri, H. A.; Al-Abd, A. M., Molecular Mimics of Classic P-Glycoprotein Inhibitors as Multidrug Resistance Suppressors and Their Synergistic Effect on Paclitaxel. *PLoS One* 2017, 12 (1), e0168938, incorporated herein by reference in its entirety) was prepared according to the procedure described for the synthesis of 1503 starting from (Z)-4-[(E)-3-(phenylallylidene)-2-(E)-styryl]oxazol-5(4H)-one (0.3 g, 1 mmol) and n-propylamine (0.16 mL, 2 mmol). The product 1712 was a light yellow solid, (0.314 g, 87%), Mp 186° C. $^1$H NMR (850 MHz, DMSO-d$_6$) $\delta_H$ 9.69 (s, 1H), 8.02 (t, J=5.71 Hz, 1H), 7.64 (d, J=7.27 Hz, 2H), 7.55-7.52 (m, 3H), 7.47-7.45 (m, 2H), 7.42-7.40 (m, 1H), 7.38-7.35 (m, 2H), 7.31-7.28 (t, J=7.26 Hz, 1H), 7.05-7.00 (dd, 1H, J=15.8 and 10.7 Hz), 6.92-6.87 (m, 2H), 6.73 (d, J=10.90 Hz, 1H), 3.12-3.08 (q, J=8.6 Hz, 2H), 1.50-1.44 (m, 2H), 0.94 (t, J=7.53 Hz, 1H), 0.87 (t, J=7.27 Hz, 3H), LC-MS (ESI) RT=5.25 min, m/z 361.1 [M+H]$^+$ (The compound contained 24.2% of E-isomer (2E,4E)-2-cinnamamido-5-phenyl-N-propylpenta-2,4-dienamide according to LC-MS (UV) determination. All data are reported for the Z isomer.

(Z)-2-[(E)-3-(4-chlorophenyl)acrylamido]-3-phenyl-N-propylacrylamide (1812)

This compound was prepared according to the procedure described for the synthesis of 1503 starting from 4-[(Z)-benzylidene]-2-[(E)-4-chlorostyryl]oxazol-5(4H)-one (0.310 g, 1 mmol) and n-propylamine (0.16 mL, 2 mmol). The product 1812 was a white solid (325 mg, 88%), Mp 190-191° C. IR (KBr, v$_{max}$ cm$^{-1}$) 3281, 2958, 1651, 1611; $^1$H NMR (850 MHz, DMSO-d$_6$) $\delta_H$ 9.71 (br. s., 1H), 8.12 (t, J=5.71 Hz, 1H), 7.64 (d, J=8.30 Hz, 2H), 7.46-7.58 (m, 4H), 7.38 (t, J=7.79 Hz, 2H), 7.31 (t, J=7.79 Hz, 1H), 7.00 (s, 1H), 6.87 (d, J=16.09 Hz, 1H), 3.12 (q, J=6.75 Hz, 2H), 1.49 (sxt, J=7.27 Hz, 2H), 0.88 (t, J=7.27 Hz, 3H); $^{13}$C NMR (214 MHz, DMSO-d$_6$) $\delta_C$ 165.1, 164.5, 138.7, 134.3, 133.8, 130.4, 129.5, 129.4, 129.2, 128.7, 128.6, 127.0, 122.4, 41.1, 39.8, 39.7, 39.6, 39.5, 39.4, 39.3, 39.2, 22.4, 11.5; LC/MS (ESI), RT=4.8 min, m/z 369 (M+1), 370 (M+2).

(Z)-2-[(E)-3-(4-methoxyphenyl)acrylamido]-3-phenyl-N-propylacrylamide (1912)

This compound was prepared according to the procedure described for the synthesis of 1503 starting from 4-[(Z)-benzylidene]-2-[(E)-4-methoxystyryl]oxazol-5(4H)-one (0.305 g, 1 mmol) and n-propylamine (0.16 mL, 2 mmol). The product 1912 was a white solid (303 mg, 83%), Mp 184-185° C. IR (KBr, v$_{max}$ cm$^{-1}$) 3229, 2964, 1650, 1625; $^1$H NMR (600 MHz, DMSO-d$_6$) $\delta_H$ 9.62 (s, 1H), 8.12 (t, J=5.65 Hz, 1H), 7.51-7.62 (m, 4H), 7.45 (d, J=15.43 Hz, 1H), 7.38 (t, J=7.72 Hz, 2H), 7.31 (t, J=7.79 Hz, 1H), 7.02 (d, J=8.66 Hz, 2H), 6.97 (s, 1H), 6.72 (d, J=15.81 Hz, 1H), 3.81 (s, 3H), 3.11 (q, J=6.40 Hz, 2H), 1.48 (sxt, J=7.30 Hz, 2H), 0.87 (t, J=7.34 Hz, 3H); $^{13}$C NMR (214 MHz, DMSO-d$_6$) $\delta_C$ 165.1, 164.9, 160.6, 139.7, 134.4, 130.7, 129.4, 129.3, 128.6, 128.5, 127.3, 126.6, 119.0, 114.5, 55.4, 41.0, 39.8, 39.7, 39.6, 39.5, 39.4, 39.3, 39.2, 22.4, 11.5; LC/MS (ESI), RT=3.5 min, m/z 365 (M+1).

(Z)-3-phenyl-N-propyl-2-[(E)-3-(p-tolyl)acrylamido]acrylamide (2012)

This compound was prepared according to the procedure described for the synthesis of 1503 starting from 4-[(Z)-benzylidene]-2-[(E)-4-methylstyryl]oxazol-5(4H)-one (0.289 g, 1 mmol) and n-propylamine (0.16 mL, 2 mmol). The product 2012 was an off-white solid (321 mg, 92%), Mp 175-176° C. IR (KBr, v$_{max}$ cm$^{-1}$) 3296, 3172, 2967, 1646, 1610; $^1$H NMR (850 MHz, DMSO-d$_6$) $\delta_H$ 9.65 (br. s., 1H), 8.11 (t, J=5.45 Hz, 1H), 7.48-7.57 (m, 4H), 7.46 (d, J=15.57 Hz, 1H), 7.37-7.40 (m, 2H), 7.27-7.34 (m, 2H), 7.26 (d, J=7.78 Hz, 1H), 6.98-7.01 (m, 1H), 6.82 (d, J=15.57 Hz, 1H), 3.09-3.13 (m, 2H), 1.48 (td, J=7.20, 14.14 Hz, 2H), 0.87 (t, J=7.27 Hz, 3H); 13C NMR (214 MHz, DMSO-d$_6$) $\delta_C$ 165.2, 164.9, 140.1, 139.8, 134.4, 132.1, 130.6, 129.8, 129.4, 128.7, 127.9, 127.5, 126.9, 120.6, 41.1, 39.8, 39.7, 39.6, 39.5, 39.4, 39.3, 39.2, 22.5, 21.1, 11.6; LC/MS (ESI), RT=4.3 min, m/z 349 (M+1).

(Z)-3-phenyl-N-propyl-2-[(E)-3-(thien-2-yl)acrylamido]acrylamide (2112)

This compound was prepared according to the procedure described for the synthesis of 1503 starting from 4-[(Z)-benzylidene]-2-[(E)-2-(thien-3-yl)vinyl]oxazol-5(4H)-one (0.281 g, 1 mmol) and n-propylamine (0.16 mL, 2 mmol). The product 2112 was an off-white solid (263 mg, 77%), Mp 195-196° C. IR (KBr, v$_{max}$ cm$^{-1}$) 3296, 3172, 2967, 1646, 1610; $^1$H NMR (850 MHz, DMSO-d$_6$) $\delta_H$ 9.65 (s, 1H), 8.10 (t, J=5.71 Hz, 1H), 7.61-7.68 (m, 2H), 7.53 (d, J=7.79 Hz, 2H), 7.43 (d, J=3.11 Hz, 1H), 7.39 (t, J=7.79 Hz, 2H), 7.31 (t, J=7.79 Hz, 1H), 7.14 (dd, J=3.37, 4.93 Hz, 1H), 6.99 (s, 1H), 6.62 (d, J=15.57 Hz, 1H), 3.11 (q, J=6.75 Hz, 2H), 1.48 (sxt, J=7.27 Hz, 2H), 0.87 (t, J=7.53 Hz, 3H); $^{13}$C NMR (214 MHz, DMSO-d$_6$) $\delta_C$ 165.0, 164.4, 139.8, 134.3, 133.0, 131.3, 130.5, 129.3, 128.6, 128.6, 128.5, 128.5, 126.9, 120.3, 41.0, 39.8, 39.7, 39.6, 39.5, 39.4, 39.3, 39.2, 22.4, 11.5; LC/MS (ESI), RT=3.4 min, m/z 341 (M+1).

(Z)-2-cinnamamido-3-(4-fluorophenyl)-N-propylacrylamide (2212)

This compound was prepared according to the procedure described for the synthesis of 1503 starting from 4-[(Z)-4-fluorobenzylidene]-2-[(E)-styryl]oxazol-5(4H)—(0.293 g, 1 mmol) and n-propylamine (0.16 mL, 2 mmol). The product 2212 was an off-white solid (290 mg, 82%), Mp 192-193° C. IR (KBr, v$_{max}$ cm$^{-1}$) 3360, 3026, 2950, 1650, 1610; $^1$H NMR (DMSO-d$_6$) $\delta_H$ ppm 9.68 (s, 1H), 8.12 (s, 1H), 7.56-7.67 (m, 4H), 7.50 (d, J=16.09 Hz, 1H), 7.44-7.47 (m, 2H), 7.42 (d, J=7.78 Hz, 1H), 7.23 (t, J=8.82 Hz, 2H), 7.01 (s, 1H), 6.86 (d, J=16.09 Hz, 1H), 3.12 (q, J=6.75 Hz, 2H), 1.45-1.52 (m, 2H), 0.87 (t, J=7.53 Hz, 3H); LC/MS (ESI), RT=3.9 min, m/z 353 (M+1).

(Z)-2-[(E)-3-(4-chlorophenyl)acrylamido]-3-(4-fluorophenyl)-N-propylacrylamide (2312)

This compound was prepared according to the procedure described for the synthesis of 1503 starting from 2-[(E)-4-chlorostyryl]-4-[(Z)-4-fluorobenzylidene]oxazol-5(4H)-one (0.327 g, 1 mmol) and n-propylamine (0.16 mL, 2 mmol). The product 2312 was an off-white solid (341 mg, 88%), Mp 187-188° C. IR (KBr, v$_{max}$ cm$^{-1}$) 3360, 3002, 2949, 1650, 1610; $^1$H NMR (850 MHz, DMSO-d$_6$) $\delta_H$ 9.69 (s, 1H), 8.12 (t, J=5.71 Hz, 1H), 7.64 (d, J=8.30 Hz, 2H), 7.60 (dd, J=5.71, 8.82 Hz, 2H), 7.46-7.55 (m, 3H), 7.20-7.26 (m, 2H), 7.01 (s, 1H), 6.85 (d, J=16.09 Hz, 1H), 3.11 (q, J=6.40 Hz, 2H), 1.48 (sxt, J=7.27 Hz, 2H), 0.87 (t, J=7.27 Hz, 3H); $^{13}$C NMR (214 MHz, DMSO-d$_6$) $\delta_C$ 164.9, 164.4, 138.7, 134.3, 133.7, 131.5, 130.9, 130.1, 129.5, 129.2, 125.9, 122.4, 115.6, 115.5, 41.0, 39.8, 39.7, 39.6, 39.5, 39.4, 39.3, 39.2, 22.4, 11.5; LC/MS (ESI), RT=5.1 min, m/z 387 (M+1), 388 (M+2).

(Z)-3-(4-fluorophenyl)-2-[(E)-3-(4-methoxyphenyl) acrylamido]-N-propylacrylamide (2412)

This compound was prepared according to the procedure described for the synthesis of 1503 starting from 4-[(Z)-4-fluorobenzylidene)]-2-[(E)-4-methoxystyryl]oxazol-5(4H)-one (0.323 g, 1 mmol) and n-propylamine (0.16 mL, 2 mmol). The product 2412 was a white solid (355 mg, 93%), Mp 199-200° C. IR (KBr, $v_{max}$ cm$^{-1}$) 3285, 2961, 1649, 1608; $^1$H NMR (600 MHz, DMSO-d$_6$) $\delta_H$ 9.61 (s, 1H), 8.12 (t, J=5.65 Hz, 1H), 7.56-7.61 (m, 4H), 7.45 (d, J=15.81 Hz, 1H), 7.20-7.26 (m, 2H), 7.02 (d, J=8.66 Hz, 2H), 6.98 (s, 1H), 6.71 (d, J=15.81 Hz, 1H), 3.81 (s, 3H), 3.11 (q, J=6.65 Hz, 2H), 1.48 (sxt, J=7.30 Hz, 2H), 0.87 (t, J=7.53 Hz, 3H); $^{13}$C NMR (214 MHz, DMSO-d$_6$) $\delta_C$ 165.1, 164.9, 160.7, 139.9, 131.5, 131.0, 130.4, 129.5, 127.3, 125.6, 119.0, 115.6, 115.5, 114.6, 55.4, 41.0, 39.8, 39.7, 39.6, 39.5, 39.4, 39.3, 39.2, 22.4, 11.5; LC/MS (ESI), RT=3.8 min, m/z 383 (M+1).

(Z)-3-(4-fluorophenyl)-N-propyl-2-[(E)-3-(p-tolyl) acrylamido]acrylamide (2512)

This compound was prepared according to the procedure described for the synthesis of 1503 starting from 4-[(Z)-4-fluorobenzyidene)]-2-[(E)-4-methylstyryl]oxazol-5(4H)-one (0.307 g, 1 mmol) and n-propylamine (0.16 mL, 2 mmol). The product 2512 was an off-white solid (289 mg, 79%), Mp 164-165° C. IR (KBr, $v_{max}$ cm$^{-1}$) 3302, 3208, 2970, 1649, 1640; $^1$H NMR (850 MHz, DMSO-d$_6$) $\delta_H$ 9.64 (s, 1H), 8.11 (t, J=5.71 Hz, 1H), 7.60 (dd, J=5.71, 8.82 Hz, 2H), 7.50 (d, J=8.30 Hz, 2H), 7.46 (d, J=16.09 Hz, 1H), 7.26 d, J=8.30 Hz, 2H), 7.20-7.25 (m, 2H), 7.00 (s, 1H), 6.81 (d, J=15.57 Hz, 1H), 3.12 (q, J=6.75 Hz, 2H), 2.35 (s, 3H), 1.48 (sxt, J=7.27 Hz, 2H), 0.87 (t, J=7.27 Hz, 3H); $^{13}$C NMR (214 MHz, DMSO-d$_6$) $\delta_C$ 165.0, 164.8, 140.0, 139.7, 132.0, 131.5, 131.0, 130.3, 129.7, 127.8, 125.7, 120.5, 115.6, 115.5, 41.0, 39.8, 39.7, 39.6, 39.5, 39.4, 39.3, 39.2, 22.4, 21.1, 11.5; LC/MS (ESI), RT=3.7 min, m/z 367 (M+1).

(Z)-3-(4-fluorophenyl)-N-propyl-2-[(E)-3-(thien-2-yl)acrylamido]acrylamide (2612)

This compound was prepared according to the procedure described for the synthesis of 1503 starting from 4-([(Z)-4-fluorobenzylidene)-2-[(E)-2-(thien-3-yl)vinyl]oxazol-5(4H)-one (0.299 g, 1 mmol) and n-propylamine (0.16 mL, 2 mmol). The product 2612 was a yellow solid (279 mg, 78%), Mp 142-143° C. IR (KBr, $v_{max}$ cm$^{-1}$) 3302, 3143, 2961, 1650, 1610; $^1$H NMR (850 MHz, DMSO-d$_6$) ppm 9.63 (s, 1H) 8.11 (t, J=5.71 Hz, 1H) 7.61-7.68 (m, 2H) 7.58 (dd, J=8.04, 5.97 Hz, 2H) 7.43 (d, J=3.11 Hz, 1H) 7.23 (t, J=8.56 Hz, 2H) 7.11-7.16 (m, 1H) 7.00 (s, 1H) 6.60 (d, J=15.57 Hz, 1H) 3.11 (q, J=6.40 Hz, 2H) 1.48 (sxt, J=7.27 Hz, 2H) 0.87 (t, J=7.53 Hz, 3H); $^{13}$C NMR (214 MHz, DMSO-d$_6$) $\delta_C$ 165.0, 164.4, 139.8, 133.1, 131.6, 131.5, 131.4, 130.9, 130.2, 128.6, 128.5, 126.3, 125.9, 120.3, 41.0, 39.8, 39.7, 39.6, 39.5, 39.4, 39.3, 39.2, 22.4, 11.5; LC/MS (ESI), RT=3.5 min, m/z 359 (M+1).

(Z)-2-cinnamamido-3-[4-(dimethylamino)phenyl]-N-propylacrylamide (2712)

This compound was prepared according to the procedure described for the synthesis of 1503 starting from 4-[(Z)-4-(dimethylamino)benzylidene]-2-[(E)-styryl]oxazol-5(4H)-one (0.318 g, 1 mmol) and n-propylamine (0.16 mL, 2 mmol). The product 2712 was an off-white solid (328 mg, 87%), Mp 207-208° C. IR (KBr, $v_{max}$ cm$^{-1}$) 3087, 2933, 1659; $^1$H NMR (600 MHz, DMSO-d$_6$) $\delta_H$ 9.51 (s, 1H), 7.91 (t, J=5.84 Hz, 1H), 7.63 (d, J=7.15 Hz, 2H), 7.45-7.52 (m, 3H), 7.40-7.44 (m, 3H), 7.04 (s, 1H), 6.90 (d, J=15.81 Hz, 1H), 6.70 (d, J=9.03 Hz, 2H), 3.11 (q, J=6.75 Hz, 2H), 2.92 (s, 6H), 1.46 (sxt, J=7.23 Hz, 2H), 0.86 (t, J=7.34 Hz, 3H); $^{13}$C NMR (214 MHz, DMSO-d$_6$) $\delta_C$ 169.6, 168.0, 142.5, 141.1, 135.8, 134.7, 131.2, 129.3, 129.0, 128.7, 128.1, 127.5, 126.3, 111.0, 41.6, 40.7, 39.8, 39.7, 39.6, 39.5, 39.4, 39.3, 39.2, 22.3, 11.4; LC/MS (ESI), RT=3.8 min, m/z 378 (M+1).

(Z)-2-[(E)-3-(4-chlorophenyl)acrylamido]-3-[4-(dimethylamino)phenyl]-N-propylacrylamide (2812)

This compound was prepared according to the procedure described for the synthesis of 1503 starting from 2-[(E)-4-chlorostyryl]-4-[(Z)-4-(dimethylamino)benzylidene]oxazol-5(4H)-one (0.353 g, 1 mmol) and n-propylamine (0.16 mL, 2 mmol). The product 2812 was a yellow solid (371 mg, 90%), Mp 243-244° C. IR (KBr, $v_{max}$ cm$^{-1}$) 3067, 2912, 1648, 1609; $^1$H NMR (600 MHz, DMSO-d$_6$) $\delta_H$ 9.53 (s, 1H), 7.92 (t, J=6.02 Hz, 1H), 7.65 (d, J=8.66 Hz, 2H), 7.53 (d, J=8.28 Hz, 2H), 7.50 (d, J=15.81 Hz, 1H), 7.42 (d, J=9.03 Hz, 2H), 7.04 (s, 1H), 6.90 (d, J=15.81 Hz, 1H), 6.69 (d, J=9.03 Hz, 2H), 3.10 (q, J=6.40 Hz, 2H), 2.93 (s, 6H), 1.46 (sxt, J=7.23 Hz, 2H), 0.86 (t, J=7.34 Hz, 3H); 13C NMR (214 MHz, DMSO-d$_6$) $\delta_C$ 166.5, 163.1, 140.1, 137.9, 134.6, 133.4, 131.2, 129.4, 129.3, 128.8, 128.6, 128.2, 127.8, 127.5, 41.3, 40.5, 39.8, 39.7, 39.6, 39.5, 39.4, 39.3, 39.2, 22.4, 11.4; LC/MS (ESI), RT=5.9 min, m/z 412 (M+1), 413 (M+2).

(Z)-3-[4-(dimethylamino)phenyl]-2-[(E)-3-(4-methoxyphenyl)acrylamido]-N-propylacrylamide (2912)

This compound was prepared according to the procedure described for the synthesis of 1503 starting from 4-[(Z)-4-(dimethylamino)benzylidene]-2-[(E)-4-methoxystyryl]-oxazol-5(4H)-one (0.348 g, 1 mmol) and n-propylamine (0.16 mL, 2 mmol). The product 2912 was a yellow solid (346 mg, 85%), Mp 236-237° C. IR (KBr, $v_{max}$ cm$^{-1}$) 3070, 2952, 1647, 1603; $^1$H NMR (600 MHz, DMSO-d$_6$) $\delta_H$ 9.41 (s, 1H), 7.88 (t, J=5.83 Hz, 1H), 7.58 (d, J=9.04 Hz, 2H), 7.40-7.47 (m, 3H), 7.01-7.04 (m, 3H), 6.75 (d, J=15.81 Hz, 1H), 6.69 (d, J=9.03 Hz, 2H), 3.81 (s, 3H), 3.10 (q, J=6.40 Hz, 2H), 2.92 (s, 6H), 1.46 (sxt, J=7.30 Hz, 2H), 0.86 (t, J=7.34 Hz, 3H); $^{13}$C NMR (214 MHz, DMSO-d$_6$) $\delta_C$ 164.3, 163.1, 158.6, 142.3, 134.5, 133.1, 131.9, 131.4, 129.4, 128.6, 119.0, 114.6, 113.9, 113.2, 55.3, 41.5, 40.5, 39.8, 39.7, 39.6, 39.5, 39.4, 39.3, 39.2, 22.1, 11.3; LC/MS (ESI), RT=3.7 min, m/z 408 (M+1).

(Z)-3-[4-(dimethylamino)phenyl]-N-propyl-2-[(E)-3-(p-tolyl)acrylamido]acrylamide (3012)

This compound was prepared according to the procedure described for the synthesis of 1503 starting from 4-[(Z)-4-(dimethylamino)benzylidene]-2-[(E)-4-methylstyryl]oxazol-5(4H)-one (0.332 g, 1 mmol) and n-propylamine (0.16 mL, 2 mmol). The product 3012 was a yellow solid (341 mg, 87%), Mp 218-219° C. IR (KBr, $v_{max}$ cm$^{-1}$) 3268, 2952, 1647, 1601; $^1$H NMR (850 MHz, DMSO-d$_6$) $\delta$ ppm 9.51 (br. s., 1H) 7.96 (t, J=5.97 Hz, 1H) 7.45-7.52 (m, 3H) 7.26 (m, J=7.78 Hz, 2H) 7.21 (s, 1H) 7.04 (s, 1H) 6.99 (d, J=8.30 Hz, 1H) 6.84 (d, J=15.57 Hz, 1H) 6.76 (d, J=8.30 Hz, 1H) 3.11 (q, J=6.57 Hz, 2H) 2.51 (br. s., 6H) 2.34 (s, 3H) 1.47 (sxt, J=7.16 Hz, 2H) 0.85-0.87 (m, 3H); LC/MS (ESI), RT=5.0 min, m/z 392 (M+1).

(Z)-3-[4-(dimethylamino)phenyl]-N-propyl-2-[(E)-3-(thien-2-yl)acrylamido]acrylamide (3112)

This compound was prepared according to the procedure described for the synthesis of 1503 starting from 4-[(Z)-4-(dimethylamino)benzylidene]-2-[(E)-2-(thien-3-yl)vinyl]-oxazol-5(4H)-one (0.324 g, 1 mmol) and n-propylamine (0.16 mL, 2 mmol). The product 3112 was an off-white solid (352 mg, 92%), Mp 208-209° C. IR (KBr, $v_{max}$ cm$^{-1}$) 3296, 2948, 1643, 1605; $^1$H NMR (600 MHz, DMSO-d$_6$) $\delta_H$ 9.47 (s, 1H), 7.90 (t, J=5.83 Hz, 1H), 7.61-7.68 (m, 2H), 7.44 (d, J=3.39 Hz, 1H), 7.40 (d, J=9.04 Hz, 2H), 7.15 (dd, J=3.58, 5.08 Hz, 1H), 7.03 (s, 1H), 6.70 (d, J=9.03 Hz, 2H), 6.64 (d, J=15.81 Hz, 1H), 3.09 (q, J=6.40 Hz, 2H), 2.93 (s, 6H), 1.46 (sxt, J=7.30 Hz, 2H), 0.85 (t, J=7.34 Hz, 3H); LC/MS (ESI), RT=3.5 min, m/z 384 (M+1).

(Z)-2-cinnamamido-3-(4-hydroxy-3-methoxyphenyl)-N-propylacrylamide (3212)

This compound was prepared according to the procedure described for the synthesis of 1503 starting from 4-[(Z)-4-hydroxy-3-methoxybenzylidene]-2-[(E)-styryl]oxazol-5(4H)-one (0.321 g, 1 mmol) and n-propylamine (0.16 mL, 2 mmol). The product 3212 was an off-white solid (323 mg, 85%), Mp 199-200° C. IR (KBr, $v_{max}$ cm$^{-1}$) 3292, 2971, 1650, 1610; $^1$H NMR (600 MHz, DMSO-d$_6$) $\delta_H$ 8.02 (br. s., H), 7.61 (d, J=7.15 Hz, 2H), 7.39-7.55 (m, 4H), 7.21 (s, 1H), 7.04 (s, 1H), 6.91 (d, J=16.19 Hz, 1H), 6.77 (d, J=8.28 Hz, 1H), 3.69 (s, 3H), 3.11 (q, J=6.65 Hz, 2H), 1.47 (sxt, J=7.15 Hz, 2H), 0.86 (t, J=7.34 Hz, 3H); $^{13}$C NMR (214 MHz, DMSO-d$_6$) $\delta_C$ 165.2, 164.8, 147.5, 147.3, 139.8, 134.9, 129.9, 129.2, 128.6, 127.7, 127.2, 125.5, 123.8, 121.8, 115.5, 112.9, 55.4, 41.0, 39.8, 39.7, 39.6, 39.5, 39.4, 39.3, 39.2, 22.5, 11.5; LC/MS (ESI), RT=2.9 min, m/z 381 (M+1).

(Z)-2-[(E)-3-(4-chlorophenyl)acrylamido]-3-(4-hydroxy-3-methoxyphenyl)-N-propylacrylamide (3312)

This compound was prepared according to the procedure described for the synthesis of 1503 starting from 2-[(E)-4-chlorostyryl]-4-[(Z)-4-hydroxy-3-methoxybenzylidene]-oxazol-5(4H)-one (0.355 g, 1 mmol) and n-propylamine (0.16 mL, 2 mmol). The product 3312 was a yellow solid (356 mg, 86%), Mp 136-137° C. IR (KBr, $v_{max}$ cm$^{-1}$) 3566, 2988, 2902, 1650; $^1$H NMR (600 MHz, DMSO-d$_6$) $\delta_H$ 9.61 (br. s., 1H), 8.01 (t, J=5.83 Hz, 1H), 7.64 (d, J=8.28 Hz, 2H), 7.48-7.56 (m, 3H), 7.20 (d, J=2.26 Hz, 1H), 7.04 (s, 1H), 6.99 (dd, J=1.88, 8.28 Hz, 1H), 6.90 (d, J=16.19 Hz, 1H), 6.76 (d, J=8.28 Hz, 1H), 3.68 (s, 3H), 3.11 (q, J=6.65 Hz, 2H), 1.47 (sxt, J=7.23 Hz, 2H), 0.86 (t, J=7.34 Hz, 3H); LC/MS (ESI), RT=3.4 min, m/z 415 (M+1), 416 (M+2).

(Z)-3-(4-hydroxy-3-methoxyphenyl)-2-[(E)-3-(4-methoxyphenyl)acrylamido]-N-propylacrylamide (3412)

This compound was prepared according to the procedure described for the synthesis of 1503 starting from 4-[(Z)-4-hydroxy-3-methoxybenzylidene]-2-[(E)-4-methoxystyryl]-oxazol-5(4H)-one (0.351 g, 1 mmol) and n-propylamine (0.16 mL, 2 mmol). The product 3412 was an orange solid (332 mg, 81%), Mp 180-181° C. IR (KBr, $v_{max}$ cm$^{-1}$) 3567, 2989, 2955, 1655; $^1$H NMR (600 MHz, DMSO-d$_6$) $\delta_H$ 9.49 (br. s., 1H), 7.97 (t, J=6.02 Hz, 1H), 7.56 (d, J=8.28 Hz, 2H), 7.46 (d, J=15.81 Hz, 1H), 7.21 (d, J=1.88 Hz, 1H), 7.00-7.03 (m, 3H), 6.99 (dd, J=1.88, 8.28 Hz, 1H), 6.77 (d, J=6.78 Hz, 1H), 6.75 (s, 1H), 3.81 (s, 3H), 3.68 (s, 3H), 3.11 (q, J=6.65 Hz, 2H), 1.47 (sxt, J=7.23 Hz, 2H), 0.86 (t, J=7.34 Hz, 3H); LC/MS (EST), RT=2.7 min, m/z 411 (M+1).

(Z)-3-(4-hydroxy-3-methoxyphenyl)-N-propyl-2-[(E)-3-(p-tolyl)acrylamido]acrylamide (3512)

This compound was prepared according to the procedure described for the synthesis of 1503 starting from 4-[(Z)-4-hydroxy-3-methoxybenzylidene]-2-[(E)-4-methylstyryl]-oxazol-5(4H)-one (0.335 g, 1 mmol) and n-propylamine (0.16 mL, 2 mmol). The product 3512 was a yellow solid (296 mg, 75%), Mp 183-184° C. IR (KBr, $v_{max}$ cm$^{-1}$) 3566, 3213, 2947, 1663; $^1$H NMR (600 MHz, DMSO-d$_6$) $\delta_H$ 9.54 (s, 1H), 9.39 (br. s., 1H), 8.00 (t, J=5.65 Hz, 1H), 7.44-7.53 (m, 3H), 7.27 (d, J=7.91 Hz, 2H), 7.21 (s, 1H), 7.03 (s, 1H), 6.99 (dd, J=1.88, 8.28 Hz, 1H), 6.85 (d, J=15.81 Hz, 1H), 6.76 (d, J=8.28 Hz, 1H), 3.68 (s, 3H), 3.10 (q, J=6.65 Hz, 2H), 2.35 (s, 3H), 1.47 (sxt, J=7.23 Hz, 2H), 0.86 (t, J=7.34 Hz, 3H); $^{13}$C NMR (214 MHz, DMSO-d) $\delta_C$ 165.1, 164.9, 147.5, 147.3, 139.7, 139.6, 132.1, 129.7, 128.5, 127.7, 127.3, 125.5, 123.7, 120.8, 115.4, 112.9, 55.3, 41.0, 39.8, 39.7, 39.6, 39.5, 39.4, 39.3, 39.2, 22.5, 11.5; LC/MS (ESI), RT=3.3 min, m/z 395 (M+1).

(Z)-3-(4-hydroxy-3-methoxyphenyl)-N-propyl-2-[(E)-3-(thien-2-yl)acrylamido]acrylamide (3612)

This compound was prepared according to the procedure described for the synthesis of 1503 starting from 4-[(Z)-4-hydroxy-3-methoxybenzylidene]-2-[(E)-2-(thien-3-yl)vinyl]-oxazol-5(4H)-one (0.327 g, 1 mmol) and n-propylamine (0.16 mL, 2 mmol). The product 3612 was a yellow solid (340 mg, 88%), Mp 192-93° C. IR (KBr, $v_{max}$ cm$^{-1}$) 3560, 3105, 2954, 1648, 1603; $^1$H NMR (600 MHz, DMSO-d$_6$) $\delta_H$ 9.54 (br. s., 1H), 7.99 (t, J=5.83 Hz, 1H), 7.63-7.68 (m, 2H), 7.43 (d, J=3.39 Hz, 1H), 7.19 (d, J=1.88 Hz, 1H), 7.13-7.16 (m, 1H), 7.04 (s, 1H), 6.98 (dd, J=1.88, 8.28 Hz, 1H), 6.76 (d, J=7.91 Hz, 1H), 6.66 (d, J=15.81 Hz, 1H), 3.69 (s, 3H), 3.11 (q, J=6.65 Hz, 2H), 1.46 (sxt, J=7.23 Hz, 2H), 0.86 (t, J=7.34 Hz, 3H); LC/MS (ESI), RT=2.7 min, m/z 387 (M+1).

(Z)-2-cinnamamido-3-(1H-indol-3-yl)-N-propylacrylamide (3712)

This compound was prepared according to the procedure described for the synthesis of 1503 starting from (Z)-4-[(1H-indol-3-yl)methylene]-2-[(E)-styryl]oxazol-5(4H)-one (0.314 g, 1 mmol) and n-propylamine (0.16 mL, 2 mmol). The product 3712 was a white solid (287 mg, 77%), Mp 249-250° C. IR (KBr, $v_{max}$ cm$^{-1}$) 3401, 3057, 2956, 1650, 1608; $^1$H NMR (600 MHz, DMSO-d$_6$) $\delta_H$ 11.56 (br. s., 1H), 9.46 (s, 1H), 7.98 (t, J=5.83 Hz, 1H), 7.74 (d, J=7.91 Hz, 1H), 7.63-7.67 (m, 3H), 7.42-7.55 (m, 6H), 7.17 (t, J=7.53 Hz, 1H), 7.12 (t, J=7.53 Hz, 1H), 6.98 (d, J=15.81 Hz, 1H), 3.14 (q, J=6.53 Hz, 2H), 1.50 (sxt, J=7.23 Hz, 2H), 0.88 (t, J=7.34 Hz, 3H); $^{13}$C NMR (214 MHz, DMSO-d$_6$) $\delta_C$ 164.5, 164.2, 141.5, 135.5, 134.8, 129.6, 129.3, 129.1, 129.0, 128.7, 127.9, 124.9, 124.6, 122.1, 120.0, 118.2, 111.9, 110.0, 41.0, 39.8, 39.7, 39.6, 39.5, 39.4, 39.3, 39.2, 22.3, 11.5; LC/MS (ESI), RT=3.3 min, m/z 374 (M+1).

(Z)-2-[(E)-3-(4-chlorophenyl)acrylamido]-3-(1H-indol-3-yl)-N-propylacrylamide (3812)

This compound was prepared according to the procedure described for the synthesis of 1503 starting from (Z)-4-[(1H-indol-3-yl)methylene]-2-[(E)-4-chlorostyryl]oxazol-5(4H)-one (0.348 g, 1 mmol) and n-propylamine (0.16 mL, 2 mmol). The product 3812 was an orange solid (330 mg, 81%), Mp 210-211° C. IR (KBr, $v_{max}$ cm$^{-1}$) 3208, 1650, 1615; $^1$H NMR (600 MHz, DMSO-d$_6$) $\delta_H$ 11.56 (br. s., 1H), 9.47 (s, 1H), 7.98 (t, J=5.83 Hz, 1H), 7.73 (d, J=7.91 Hz, 1H), 7.68 (d, J=8.66 Hz, 2H), 7.65 (d, J=2.63 Hz, 1H), 7.50-7.56 (m, 4H), 7.43 (d, J=7.91 Hz, 1H), 7.17 (t, J=7.15 Hz, 1H), 7.12 (t, J=7.34 Hz, 1H), 6.98 (d, J=15.81 Hz, 1H), 3.14 (q, J=6.53 Hz, 2H), 1.50 (sxt, J=7.30 Hz, 2H), 0.88 (t, J=7.53 Hz, 3H); $^{13}$C NMR (214 MHz, DMSO-d$_6$) $\delta_C$ 165.7, 165.3, 140.5, 138.1, 135.7, 134.2, 132.3, 132.2, 130.7, 130.6, 130.5, 130.1, 129.8, 125.1, 123.9, 122.7, 113.7, 111.5, 110.1, 41.6, 39.8, 39.7, 39.6, 39.5, 39.4, 39.3, 39.2, 23.0, 11.6; LC/MS (ESI), RT=4.2 min, m/z 408 (M+1), 409 (M+2).

(Z)-3-(1H-indol-3-yl)-2-[(E)-3-(4-methoxyphenyl)acrylamido]-N-propylacrylamide (3912)

This compound was prepared according to the procedure described for the synthesis of 1503 starting from (Z)-4-[(1H-indol-3-yl)methylene]-2-[(E)-4-methoxystyryl]oxazol-5(4H)-one (0.344 g, 1 mmol) and n-propylamine (0.16 mL, 2 mmol). The product 3912 was an orange solid (335 mg, 83%), Mp 225-226° C. IR (KBr, $v_{max}$ cm$^{-1}$) 3181, 1650, 1615; $^1$H NMR (600 MHz, DMSO-d$_6$) $\delta_H$ 11.55 (br. s., 1H), 9.36 (s, 1H), 7.95 (t, J=5.83 Hz, 1H), 7.73 (d, J=7.91 Hz, 1H), 7.64 (d, J=2.26 Hz, 1H), 7.60 (d, J=8.66 Hz, 2H), 7.46-7.50 (m, 2H), 7.43 (d, J=7.91 Hz, 1H), 7.17 (t, J=7.53 Hz, 1H), 7.12 (t, J=7.53 Hz, 1H), 7.03 (d, J=8.66 Hz, 2H), 6.84 (d, J=15.81 Hz, 1H), 3.82 (s, 3H), 3.14 (q, J=6.27 Hz, 2H), 1.49 (sxt, J=7.23 Hz, 2H), 0.88 (t, J=7.34 Hz, 3H); $^{13}$C NMR (214 MHz, DMSO-d$_6$) $\delta_C$ 166.0, 164.3, 160.6, 141.5, 138.5, 137.1, 132.3, 131.9, 131.4, 129.2, 123.5, 122.2, 121.0, 120.6, 114.6, 113.9, 112.5, 112.3, 55.8, 41.5, 39.8, 39.7, 39.6, 39.5, 39.4, 39.3, 39.2, 22.6, 11.5; LC/MS (ESI), RT=3.2 min, m/z 404 (M+1).

(Z)-3-(1H-indol-3-yl)-N-propyl-2-[(E)-3-(p-tolyl)acrylamido]acrylamide (4012)

This compound was prepared according to the procedure described for the synthesis of 1503 starting from (Z)-4-[(1H-indol-3-yl)methylene]-2-[(E)-4-methylstyryl]oxazol-5(4H)-one (0.328 g, 1 mmol) and n-propylamine (0.16 mL, 2 mmol). The product 4012 was a yellow solid (345 mg, 89%), Mp 192-193° C. IR (KBr, $v_{max}$ cm$^{-1}$) 3220, 2950, 1651, 1595; $^1$H NMR (600 MHz, DMSO-d$_6$) $\delta_H$ 11.56 (br. s., 1H), 9.42 (s, 1H), 7.97 (t, J=5.83 Hz, 1H), 7.73 (d, J=7.91 Hz, 1H), 7.65 (s, 1H), 7.54 (d, J=7.91 Hz, 2H), 7.47-7.52 (m, 2H), 7.43 (d, J=7.91 Hz, 1H), 7.28 (d, J=7.91 Hz, 2H), 7.17 (t, J=7.53 Hz, 1H), 7.12 (t, J=7.53 Hz, 1H), 6.93 (d, J=15.81 Hz, 1H), 3.14 (q, J=6.40 Hz, 2H), 2.36 (s, 3H), 1.50 (sxt, J=7.30 Hz, 2H), 0.88 (t, J=7.53 Hz, 3H); $^{13}$C NMR (214 MHz, DMSO-d$_6$) $\delta_C$ 165.1, 164.6, 141.5, 139.6, 135.5, 129.8, 129.6, 129.2, 127.9, 127.7, 127.6, 122.2, 121.3, 121.1, 118.2, 112.5, 111.9, 110.0, 40.9, 39.8, 39.7, 39.6, 39.5, 39.4, 39.3, 39.2, 22.6, 21.0, 11.5; LC/MS (ESI), RT=3.7 min, m/z 388 (M+1).

(Z)-3-(1H-indol-3-yl)-N-propyl-2-[(E)-3-(thien-2-yl)acrylamido]acrylamide (4112)

This compound was prepared according to the procedure described for the synthesis of 1503 starting from (Z)-4-[(H-indol-3-yl)methylene]-2-[(E)-2-(thien-3-yl)vinyl]oxazol-5(4H)-one (0.320 g, 1 mmol) and n-propylamine (0.16 mL, 2 mmol). The product 4112 was a yellow solid (326 mg, 86%), Mp 244-245° C. IR (KBr, $v_{max}$ cm$^{-1}$) 3567, 3997, 2950, 1650; H NMR (600 MHz, DMSO-d$_6$) $\delta_H$ 11.56 (br. s., 1H), 9.41 (s, 1H), 7.96 (t, J=5.83 Hz, 1H), 7.72 (d, J=7.91 Hz, 1H), 7.65-7.70 (m, 2H), 7.64 (d, J=1.88 Hz, 1H), 7.50 (s, 1H), 7.42-7.46 (m, 2H), 7.14-7.19 (m, 2H), 7.12 (t, J=7.53 Hz, 1H), 6.73 (d, J=15.43 Hz, 1H), 3.13 (q, J=6.40 Hz, 2H), 1.49 (sxt, J=7.23 Hz, 2H), 0.88 (t, J=7.53 Hz, 3H); $^{13}$C NMR (214 MHz, DMSO-d$_6$) $\delta_C$ 163.8, 163.2, 139.7, 138.1, 136.5, 136.2, 133.4, 133.3, 132.4, 129.1, 128.3, 123.6, 122.9, 122.2, 121.1, 120.6, 112.3, 107.4, 41.4, 39.8, 39.7, 39.6, 39.5, 39.4, 39.3, 39.2, 22.3, 11.3; LC/MS (ESI), RT=3.1 min, m/z 380 (M+1).

(Z)-2-cinnamamido-N-propyl-3-(pyridin-3-yl)acrylamide (4212)

This compound was prepared according to the procedure described for the synthesis of 1503 starting from (Z)-4-(pyridin-3-ylmethylene)-2-[(E)-styryl]oxazol-5(4H)-one (0.276 g, 1 mmol) and n-propylamine (0.16 mL, 2 mmol). The product 4212 was a white solid (248 mg, 74%), Mp 189-190° C. IR (KBr, $v_{max}$ cm$^{-1}$) 3258, 2964, 1649, 1610; $^1$H NMR (600 MHz, DMSO-d$_6$) $\delta_H$ 9.82 (s, 1H), 8.70 (d, J=2.26 Hz, 1H), 8.47 (dd, J=1.69, 4.71 Hz, 1H), 8.25 (t, J=5.65 Hz, 1H), 7.92 (td, J=1.74, 8.19 Hz, 1H), 7.60-7.66 (m, 2H), 7.51 (d, J=15.81 Hz, 1H), 7.39-7.49 (m, 4H), 7.00 (s, 1H), 6.86 (d, J=16.19 Hz, 1H), 3.13 (q, J=6.40 Hz, 2H), 1.49 (sxt, J=7.30 Hz, 2H), 0.88 (t, J=7.34 Hz, 3H); 13C NMR (214 MHz, DMSO-d$_6$) $\delta_C$ 164.7, 164.5, 150.1, 148.9, 140.3, 135.9, 134.7, 132.2, 130.5, 129.9, 129.1, 127.8, 123.7, 123.2, 121.4, 41.0, 39.8, 39.7, 39.6, 39.5, 39.4, 39.3, 39.2, 22.4, 11.5; LC/MS (ESI), RT=2.7 min, m/z 336 (M+1).

(Z)-2-[(E)-3-(4-chlorophenyl)acrylamido]-N-propyl-3-(pyridin-3-yl)acrylamide (4312)

This compound was prepared according to the procedure described for the synthesis of 1503 starting from (Z)-2-[(E)-4-chlorostyryl]-4-(pyridin-3-ylmethylene)oxazol-5(4H)-one (0.310 g, 1 mmol) and n-propylamine (0.16 mL, 2 mmol). The product 4312 was a white solid (288 mg, 78%), Mp 191-192° C. IR (KBr, $v_{max}$ cm$^{-1}$) 3261, 2964, 1649, 1609; $^1$H NMR (600 MHz, DMSO-d$_6$) $\delta_H$ 9.83 (br. s., 1H), 8.70 (d, J=2.26 Hz, 1H), 8.47 (dd, J=1.69, 4.71 Hz, 1H), 8.25 (t, J=5.46 Hz, 1H), 7.92 (d, J=7.91 Hz, 1H), 7.63 (d, J=7.15 Hz, 2H), 7.51 (d, J=15.81 Hz, 1H), 7.44-7.48 (m, 2H), 7.40-7.44 (m, 2H), 7.00 (s, 1H), 6.86 (d, J=15.81 Hz, 1H), 3.13 (q, J=6.53 Hz, 2H), 1.49 (sxt, J=7.30 Hz, 2H), 0.88 (t, J=7.34 Hz, 3H).

(Z)-2-[(E)-3-(4-methoxyphenyl)acrylamido]-N-propyl-3-(pyridin-3-yl)acrylamide (4412)

This compound was prepared according to the procedure described for the synthesis of 1503 starting from (Z)-2-[(E)-4-methoxystyryl]-4-(pyridin-3-ylmethylene)oxazol-5(4H)- one (0.306 g, 1 mmol) and n-propylamine (0.16 mL, 2 mmol). The product 4412 was a white solid (300 mg, 82%), Mp 185-186° C. IR (KBr, $v_{max}$ cm$^{-1}$) 3273, 3220, 2964, 1648, 1616; $^1$H NMR (600 MHz, DMSO-d$_6$) $\delta_H$ 9.72 (s, 1H), 8.69 (s, 1H), 8.47 (dd, J=1.69, 4.71 Hz, 1H), 8.22 (t, J=5.27 Hz, 1H), 7.91 (dd, J=1.32, 8.09 Hz, 1H), 7.57 (d, J=8.66 Hz, 2H), 7.46 (d, J=15.43 Hz, 1H), 7.41 (dd, J=4.71, 8.09 Hz, 1H), 7.02 (d, J=8.66 Hz, 2H), 6.97 (s, 1H), 6.71 (d, J=15.81 Hz, 1H), 3.81 (s, 3H), 3.13 (q, J=6.53 Hz, 2H), 1.49 (sxt, J=7.23 Hz, 2H), 0.88 (t, J=7.34 Hz, 3H); $^{13}$C NMR (214 MHz, DMSO-d$_6$) $\delta_C$ 164.8, 164.4, 160.7, 150.1, 148.9, 140.1, 135.9, 132.3, 130.6, 129.5, 127.3, 123.7, 123.0, 118.8, 114.6, 55.4, 41.0, 39.8, 39.7, 39.6, 39.5, 39.4, 39.3, 39.2, 22.4, 11.5; LC/MS (ESI), RT=2.7 min, m/z 366 (M+1).

(Z)—N-propyl-3-(pyridin-3-yl)-2-[(E)-3-(p-tolyl)acrylamido]acrylamide (4512)

This compound was prepared according to the procedure described for the synthesis of 1503 starting from (Z)-2-[(E)-4-methylstyryl]-4-(pyridin-3-ylmethylene)oxazol-5(4H)-one (0.290 g, 1 mmol) and n-propylamine (0.16 mL, 2 mmol). The product 4512 was a white solid (272 mg, 78%), Mp 190-191° C. IR (KBr, $v_{max}$ cm$^{-1}$) 3270, 2967, 1648, 1608; $^1$H NMR (600 MHz, DMSO-d$_6$) $\delta_H$ 9.77 (s, 1H), 8.69 (d, J=1.88 Hz, 1H), 8.47 (dd, J=1.69, 4.71 Hz, 1H), 8.23 (t, J=5.83 Hz, 1H), 7.92 (td, J=1.60, 8.09 Hz, 1H), 7.52 (d, J=7.91 Hz, 2H), 7.47 (d, J=15.81 Hz, 1H), 7.41 (dd, J=4.33, 8.09 Hz, 1H), 7.27 (d, J=7.91 Hz, 2H), 6.98 (s, 1H), 6.80 (d, J=15.81 Hz, 1H), 3.12 (q, J=6.65 Hz, 2H), 2.35 (s, 3H), 1.49 (sxt, J=7.30 Hz, 2H), 0.88 (t, J=7.34 Hz, 3H); $^{13}$C NMR (214 MHz, DMSO-d$_6$) $\delta_C$ 164.7, 164.6, 150.1, 148.9, 140.3, 139.8, 135.9, 132.3, 132.0, 130.6, 129.7, 127.8, 123.7, 123.1, 120.4, 41.1, 39.8, 39.7, 39.6, 39.5, 39.4, 39.3, 39.2, 22.4, 21.1, 11.5; LC/MS (ESI), RT=3.1 min, m/z 350 (M+1).

(Z)—N-propyl-3-(pyridin-3-yl)-2-[(E)-3-(thien-2-yl)acrylamido]acrylamide (4612)

This compound was prepared according to the procedure described for the synthesis of 1503 starting from (Z)-4-(pyridin-3-ylmethylene)-2-[(E)-2-(thien-3-yl)vinyl]oxazol-5(4H)-one (0.282 g, 1 mmol) and n-propylamine (0.16 mL, 2 mmol). The product 4612 was an off-white solid (300 mg, 88%), Mp 182-183° C. IR (KBr, $v_{max}$ cm$^{-1}$) 3270, 2967, 1647, 1605; $^1$H NMR (600 MHz, DMSO-d$_6$) $\delta_H$ 9.78 (br. s., 1H), 8.68 (d, J=1.88 Hz, 1H), 8.47 (dd, J=1.51, 4.89 Hz, 1H), 8.23 (t, J=5.84 Hz, 1H), 7.91 (td, J=1.79, 8.09 Hz, 1H), 7.62-7.70 (m, 2H), 7.39-7.47 (m, 2H), 7.15 (dd, J=3.58, 5.08 Hz, 1H), 6.99 (s, 1H), 6.60 (d, J=15.81 Hz, 1H), 3.12 (q, J=6.65 Hz, 2H), 1.49 (sxt, J=7.23 Hz, 2H), 0.88 (t, J=7.53 Hz, 3H); $^{13}$C NMR (214 MHz, DMSO-d$_6$) $\delta_C$ 164.6, 164.2, 150.1, 148.9, 139.7, 135.9, 133.3, 132.1, 131.5, 131.5, 130.5, 128.6, 123.7, 123.2, 120.1, 41.0, 39.8, 39.7, 39.6, 39.5, 39.4, 39.3, 39.2, 22.3, 11.5; LC/MS (ESI), RT=2.8 min, m/z 342 (M+1).

(Z)-2-cinnamamido-3-(4-nitrophenyl)-N-propylacrylamide (4712)

This compound was prepared according to the procedure described for the synthesis of 1503 starting from 4-[(Z)-4-nitrobenzylidene]-2-[(E)-styryl]oxazol-5(4H)-one (0.320 g, 1 mmol) and n-propylamine (0.16 mL, 2 mmol). The product 4712 was a white solid (341 mg, 90%), Mp 211-212° C. IR (KBr, $v_{max}$ cm$^{-1}$) 3294, 2958, 1647, 1619; $^1$H NMR (600 MHz, DMSO-d$_6$) $\delta_H$ 9.94 (br. s., 1H), 8.34 (t, J=5.84 Hz, 1H), 8.23 (d, J=8.66 Hz, 2H), 7.77 (d, J=9.03 Hz, 2H), 7.62 (d, J=7.15 Hz, 2H), 7.51 (d, J=15.81 Hz, 1H), 7.43-7.48 (m, 3H), 6.96 (s, 1H), 6.86 (d, J=16.19 Hz, 1H), 3.13 (q, J=6.65 Hz, 2H), 1.50 (sxt, J=7.30 Hz, 2H), 0.89 (t, J=7.53 Hz, 3H); $^{13}$C NMR (214 MHz, DMSO-d$_6$) $\delta_C$ 164.7, 164.3, 146.4, 141.7, 140.5, 134.7, 133.8, 130.2, 130.0, 129.1, 127.8, 123.7, 123.0, 121.3, 41.1, 39.8, 39.7, 39.6, 39.5, 39.4, 39.3, 39.2, 22.3, 11.5; LC/MS (ESI), RT=3.7 min, m/z 380 (M+1).

(Z)-2-[(E)-3-(4-chlorophenyl)acrylamido]-3-(4-nitrophenyl)-N-propylacrylamide (4812)

This compound was prepared according to the procedure described for the synthesis of 1503 starting from 2-[(E)-4-chlorostyryl]-4-[(Z)-4-nitrobenzylidene]oxazol-5(4H)-one (0.355 g, 1 mmol) and n-propylamine (0.16 mL, 2 mmol). The product 4812 was a yellow solid (363 mg, 88%), Mp 199-200° C. IR (KBr, $v_{max}$ cm$^{-1}$) 3070, 2967, 1648, 1622, 1530, 1350; $^1$H NMR (600 MHz, DMSO-d$_6$) $\delta_H$ 9.95 (s, 1H), 8.34 (t, J=5.46 Hz, 1H), 8.23 (d, J=9.04 Hz, 2H), 7.77 (d, J=9.04 Hz, 2H), 7.65 (d, J=8.66 Hz, 2H), 7.50-7.55 (m, 3H), 6.97 (s, 1H), 6.86 (d, J=15.81 Hz, 1H), 3.13 (q, J=6.53 Hz, 2H), 1.50 (sxt, J=7.23 Hz, 2H), 0.89 (t, J=7.53 Hz, 3H); $^{13}$C NMR (214 MHz, DMSO-d$_6$) $\delta_C$ 164.7, 164.1, 146.4, 141.7, 139.1, 134.4, 133.7, 133.7, 130.2, 129.5, 129.2, 123.7, 123.1, 122.1, 41.1, 39.8, 39.7, 39.6, 39.5, 39.4, 39.3, 39.2, 22.3, 11.5; LC/MS (ESI), RT=4.9 min, m/z 414 (M+1), 415 (M+2).

(Z)-2-[(E)-3-(4-methoxyphenyl)acrylamido]-3-(4-nitrophenyl)-N-propylacrylamide (4912)

This compound was prepared according to the procedure described for the synthesis of 1503 starting from 2-[(E)-4-methoxystyryl]-4-[(Z)-4-nitrobenzylidene]oxazol-5(4H)-one (0.350 g, 1 mmol) and n-propylamine (0.16 mL, 2 mmol). The product 4912 was a yellow solid (348 mg, 85%), Mp 235-236° C. IR (KBr, $v_{max}$ cm$^{-1}$) 3264, 2967, 1644, 1608, 1520, 1335; $^1$H NMR (600 MHz, DMSO-d$_6$) $\delta_H$ 9.84 (br. s., 1H), 8.31 (t, J=5.65 Hz, 1H), 8.23 (d, J=9.04 Hz, 2H), 7.77 (d, J=8.66 Hz, 2H), 7.57 (d, J=8.66 Hz, 2H), 7.46 (d, J=15.81 Hz, 1H), 7.02 (d, J=8.66 Hz, 2H), 6.93 (s, 1H), 6.71 (d, J=15.81 Hz, 1H), 3.81 (s, 3H), 3.13 (q, J=6.40 Hz, 2H), 1.50 (sxt, J=7.23 Hz, 2H), 0.89 (t, J=7.53 Hz, 3H); $^{13}$C NMR (214 MHz, DMSO-d$_6$) $\delta_C$ 164.8, 164.6, 160.7, 146.3, 141.8, 140.3, 134.0, 130.1, 129.5, 127.2, 123.7, 122.6, 118.7, 114.5, 55.4, 41.1, 39.8, 39.7, 39.6, 39.5, 39.4, 39.3, 39.2, 22.3, 11.5.

(Z)-3-(4-nitrophenyl)-N-propyl-2-[(E)-3-(p-tolyl)acrylamido]acrylamide (5012)

This compound was prepared according to the procedure described for the synthesis of 1503 starting from 2-[(E)-4-methylstyryl]-4-[(Z)-4-nitrobenzylidene]oxazol-5(4H)-one (0.334 g, 1 mmol) and n-propylamine (0.16 mL, 2 mmol). The product 5012 was a yellow solid (350 mg, 89%), Mp 206-207° C. IR (KBr, $v_{max}$ cm$^{-1}$) 3257, 2964, 1647, 1621, 1515, 1340; $^1$H NMR (600 MHz, DMSO-d$_6$) $\delta_H$ 9.89 (s, 1H), 8.33 (t, J=5.65 Hz, 1H), 8.23 (d, J=9.04 Hz, 2H), 7.77 (d, J=9.04 Hz, 2H), 7.45-7.52 (m, 3H), 7.27 (d, J=7.91 Hz, 2H), 6.95 (s, 1H), 6.80 (d, J=15.81 Hz, 1H), 3.13 (q, J=6.53 Hz, 2H), 2.35 (s, 3H), 1.50 (sxt, J=7.30 Hz, 2H), 0.89 (t, J=7.34 Hz, 3H); $^{13}$C NMR (214 MHz, DMSO-d$_6$) $\delta_C$ 164.8, 164.5, 146.4, 141.8, 140.5, 139.9, 133.9, 131.9, 130.1, 129.7, 127.9, 123.7, 122.8, 120.3, 41.1, 39.8, 39.7, 39.6, 39.5, 39.4, 39.3, 39.2, 22.3, 21.1, 11.5; LC/MS (ESI), RT=5.8 min, m/z 394 (M+1).

(Z)-3-(4-nitrophenyl)-N-propyl-2-[(E)-3-(thien-2-yl)acrylamido]acrylamide (5112)

This compound was prepared according to the procedure described for the synthesis of 1503 starting from 4-[(Z)-4-nitrobenzylidene]-2-[(E)-2-(thien-3-yl)vinyl]oxazol-5(4H)-one (0.326 g, 1 mmol) and n-propylamine (0.16 mL, 2 mmol). The product 5112 was a yellow solid (320 mg, 83%), Mp 187-188° C. IR (KBr, $v_{max}$ cm$^{-1}$) 3272, 2964, 1650, 1609, 1510, 1335; $^1$H NMR (600 MHz, DMSO-d$_6$) $\delta_H$ 9.89 (s, 1H), 8.32 (t, J=5.65 Hz, 1H), 8.24 (d, J=9.04 Hz, 2H), 7.76 (d, J=9.03 Hz, 2H), 7.64-7.69 (m, 2H), 7.45 (d, J=3.39 Hz, 1H), 7.15 (dd, J=3.58, 5.08 Hz, 1H), 6.95 (s, 1H), 6.60 (d, J=15.43 Hz, 1H), 3.12 (q, J=6.40 Hz, 2H), 1.50 (sxt, J=7.30 Hz, 2H), 0.89 (t, J=7.53 Hz, 3H); $^{13}$C NMR (214 MHz, DMSO-d$_6$) $\delta_C$ 164.7, 164.1, 146.4, 141.7, 139.7, 133.7, 133.6, 131.6, 130.1, 128.7, 128.6, 123.7, 123.0, 120.0, 41.1, 39.8, 39.7, 39.6, 39.5, 39.4, 39.3, 39.2, 22.3, 11.5; LC/MS (ESI), RT=4.9 min, m/z 386 (M+1).

Biological Screening Methods
Materials for Cell Culture

Different cell lines were originally purchased from American type culture collection (ATCC, Wesel, Germany) and grown in the tissue culture lab of the Egyptian company for production of vaccines, sera and drugs (Vacsera, Giza, Egypt). The cells were transferred to our laboratory and maintained in the appropriate media as following. HCT-116, CACO-2, and HT-29 (human colon cancer cell lines) were maintained in Roswell Park Memorial Institute medium (RPMI1640) (Invitrogen, Carlsbad, Calif.). The mouse skin fibroblasts (C-166) and Baby Hamster Kidney fibroblasts (BHK) were grown in Dulbecco Modified Eagle's medium (DMEM). Both media were supplemented with 1% of 100 mg/mL of streptomycin, 100 units/mL of penicillin and 10% of heat-inactivated fetal bovine serum (Invitrogen, Carlsbad, Calif.) in a humidified, 5% (v/v) CO2 atmosphere at 37° C.

Cytotoxicity Assay

The sulforhodamine B (SRB) assays were performed according to Skehan, P.; Storeng, R.; Scudiero, D.; Monks, A.; McMahon, J.; Vistica, D.; Warren, J. T.; Bokesch, H.; Kenney, S.; Boyd, M. R., New colorimetric cytotoxicity assay for anticancer-drug screening. *J Natl Cancer Inst* 1990, 82 (13), 1107-12, incorporated herein by reference in its entirety. Briefly, exponentially growing cells were trypsinized, counted and seeded at the appropriate densities (5000 cells/100 μL/well) into 96-well microtiter plates. Cells were incubated in a humidified atmosphere at 37° C. for 24 h. Then, the cells were exposed to different compounds at the desired concentrations, (0.01, 0.1, 1, 10, and 100 μM) or to 1% dimethyl sulfoxide (DMSO) for 72 h. At the end of the treatment period, the media were removed, and the cells were fixed with 10% trichloroacetic acid at 4° C. for 1 hr. Following, the cells were washed with tap water four times and incubated with SRB 0.4% for 30 min. Excess dye was removed by washing repeatedly with 1% (vol/vol) acetic acid. The protein-bound dye was dissolved in 10 mM Tris base solution for (optical density) OD determination at 510 nm using a SpectraMax plus Microplate Reader (Molecular Devices, CA). Cell viability was expressed relative to the untreated control cells.

Nuclear Fragmentation by DAPI Staining

Cells were cultured on sterile 22 mm$^2$ cover slips (Harvard Apparatus, MA, USA) in sterile six well plates at a density of 2×10$^5$ cells/well. 24 h after seeding, cells were exposed to IC$_{50}$ of the tested compound in fresh medium for 24 h. At the end of the exposure, cells attached to cover slips were washed with phosphate-buffered saline (PBS) and fixed with 3.7% paraformaldhyde for 10 min, permeabilized with 0.25% Triton X-100 in tris-buffered saline-Tween 20 (TBST) containing 0.01% Tween 20 for 10 min, and blocked for 1 hr with 5% goat serum in TBST. The fixed and permeabilized cells nuclei were denatured with 2 N HCl (300 μl) for 10 min, washed three times more, and treated with 0.1 μg/ml 4',6'-diamidino-2-phenylindole, dihydrochloride (DAPI) (Sigma-Aldrich, St. Louis, Mo., USA) (1:1000) in (phosphate-buffered saline-Tween 20 (PBST) for 1 hr. After staining, the cells were washed twice with PBS. The cover slips were then mounted on a glass slide with anti-fade mounting medium and viewed with an epifluorescence microscope, Leica, DM 5500 B (Leica, Buffalo Grove, Ill., USA) at a magnification of 60×, and data were captured digitally and quantified using the microscope provided software.

Cell Morphology

Cells were cultured on sterile 22 mm$^2$ cover slips (Harvard Apparatus, MA, USA) in sterile six well plates at a density of 2×10$^5$ cells/well. 24 h after seeding, cells were exposed to IC$_{50}$ of the tested compounds in fresh medium for 24 h. At the end of the exposure, cells attached to cover slips were washed with PBS and visualized under leica light microscope (Leica, Buffalo Grove, Ill., USA).

Cell Cycle Analysis

To analyze the DNA content by flow cytometry, HCT-116 cells were seeded at a density of 3×10$^6$ cell/T 75 flask for 24 h and then exposed to different compounds at their IC$_{50}$ values for 24 h. The cells were collected by trypsinization, washed with phosphate buffered saline (PBS) and fixed in ice-cold absolute alcohol. Thereafter, cells were stained using Cycletest™ Plus DNA Reagent Kit (BD Biosciences, San Jose, Calif.) according to the manufacturer's instructions. Cell cycle distribution was determined using a FACS Calibur flow cytometer (BD Biosciences, San Jose, Calif.).

Primary (1°) Colonosphere Formation Assay

For primary sphere formation, cells were plated in non-treated, low adhesion, 96 wells plate at the concentration of 100 cells/100 μL/well in stem cell media (SCM) that consisted of DMEM:F12:AA (Gibco), supplemented with 1×B27 (Gibco), 20 ng/mL epidermal growth factor, and 10 ng/mL fibroblast growth factor (Sigma). After 4 h of incubation, vehicle (control) or 3712 and 4112 at the desired concentrations were added to each well (at least in triplicates for each sample). On day five, numbers of spheres ranging from 50 to 150 mm in diameter were counted using phase contrast microscope and percent inhibition was calculated compared to control.

Determination of ROS Accumulation

To determine the effect of the newly synthesized compounds on the cellular redox status, two different free radical sensitive probe dichlorofluorescin diacetate (DCFDA) was used. Cells were cultured on sterile 22 mm$^2$ cover slips (Harvard Apparatus, MA, USA) in sterile six well plates at a density of 2×10$^5$ cells/well. 24 h after seeding, cells were exposed to IC$_{50}$ of the tested compounds in fresh medium for 24 h. At the end of the exposure, cells attached to cover slips were washed thrice with PBS and incubated with DCFDA 10 μM for 30 min at 37° C. in the dark. Thereafter, cells were washed thrice with PBS and the cover slips were then mounted on a glass slide with anti-fade mounting medium containing 4',6'-diamidino-2-phenylindole, dihydrochloride (DAPI) (Sigma-Aldrich, St. Louis, Mo., USA), which was used as counter stain and viewed with an epifluorescence microscope, Leica, DM 5500 B (Leica, Buffalo Grove, Ill., USA) at a magnification of 60×. Data were captured digitally and quantified using the microscope provided software.

Apoptotic Cell Determination

Apoptosis was determined by staining cells with Annexin V-fluorescein isothiocyanate (FITC) and counterstaining with propidium iodide (PI) using the Annexin V-FITC/PI apoptosis detection kit (BD Biosciences, San Diego, Calif., USA) according to the manufacturer's instructions. Briefly, $4 \times 10^6$ cell/T 75 flask were exposed to the $IC_{50}$ of tested compound for 24 and 48 h. The cells were collected by trypsinization and $0.5 \times 10^6$ cells were washed twice with phosphate-buffered saline (PBS) and stained with 5 µl Annexin V-FITC and 5 PI in 1× binding buffer (BD Biosciences, San Jose, Calif., USA) for 15 min at room temperature in the dark. Analyses were performed using FACS Calibur flow cytometer (BD Biosciences, San Jose, Calif., USA).

Determination of Acute Oral Toxicity ($LD_{50}$)

A. Animals and Compounds

The experiment was conducted on 12 healthy Swiss albino mice (males and females) weighing 22-27 g and aged 8 to 10 weeks obtained from the Animal Station, Pharmacology Dept, Faculty of Pharmacy, King Abdulaziz University, Jeddah. See Shoieb, S. M.; Esmat, A.; Khalifa, A. E.; Abdel-Naim, A. B., Chrysin attenuates testosterone-induced benign prostate hyperplasia in rats. *Food and Chemical Toxicology* 2018, 111, 650-659, incorporated herein by reference in its entirety. All animals were kept at the regulated temperature (average 23° C.), air quality (Central air conditioning) and light (12-h light/dark cycles). Animals were provided free access to food pellets ad libitum and water. The experimental procedure was approved by the Research Ethics Committee, Faculty of Pharmacy, King Abdulaziz University prior to starting the laboratory work. Animals were humanely treated according to international and scientific principles. Changes other than vitality of the animals such as behavioral and food consumption habits were not observed in this study.

The compounds 1512, 3712 and 4112 of purity 95% or more (LC/MS) were prepared for this study as 10% suspension in water containing 0.5% tween 80.

B. Acute Oral Toxicity Test

The animals were distributed randomly into four groups (3 mice at each group). One group did not receive any drug (control group). The second group received an oral dose of 2000 mg/Kg of the drug and observed after 24 h to count the deceased animals. According to the Guideline 423, when all animals were found alive, the same test was repeated (dose 2000 mg/kg) were given to the third group (3 animals) and observed for 24 h. All animals survived and therefore, a dose of 5000 mg/kg were administered to the fourth and final group.

The invention claimed is:

1. A compound of formula (I),

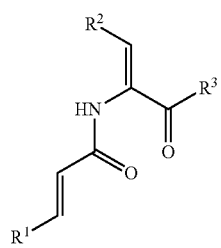

(I)

or a pharmaceutically acceptable salt, solvate, tautomer, or stereoisomer thereof, wherein:

$R^1$ is an optionally substituted aryl or an optionally substituted heteroaryl;

$R^2$ is an optionally substituted aryl or an optionally substituted heteroaryl; and wherein $R^3$ is n-propylamino.

2. The compound of formula (I) of claim 1, which is selected from the group consisting of

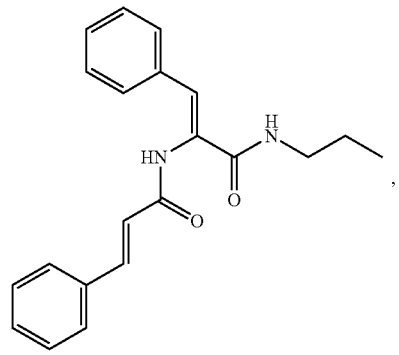

,

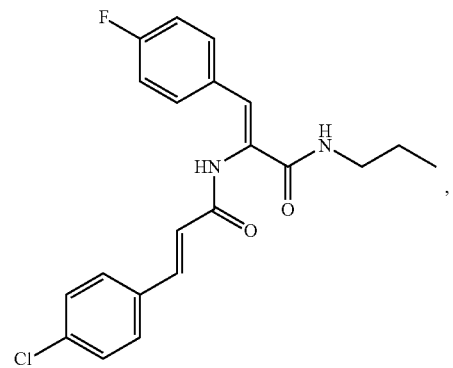

,

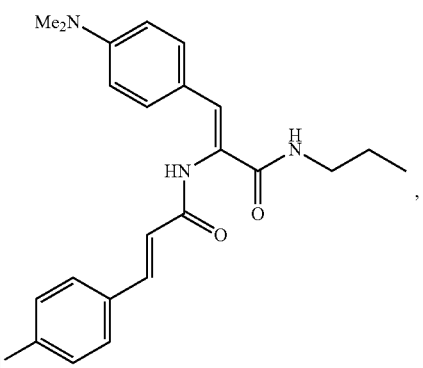

,

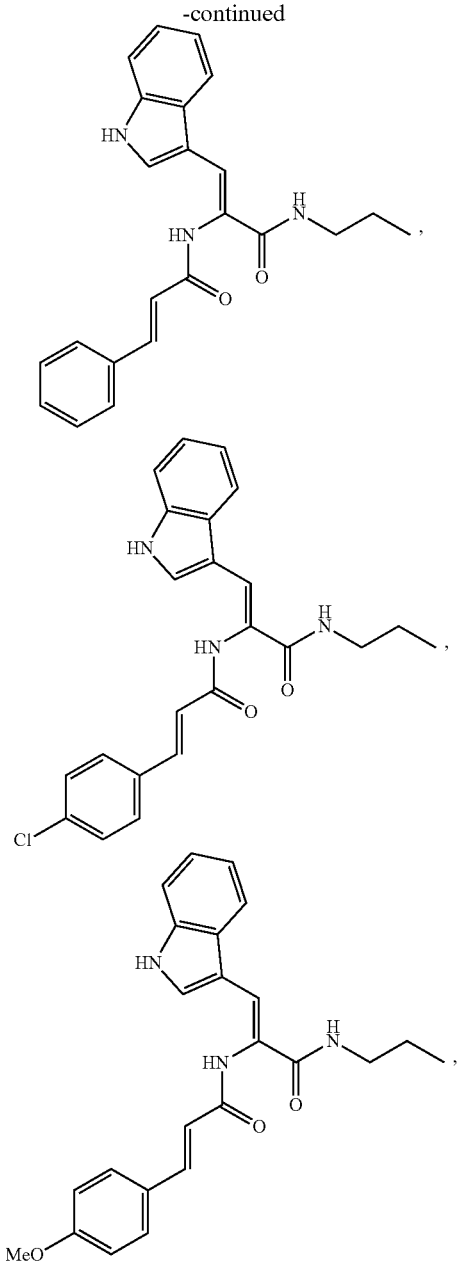
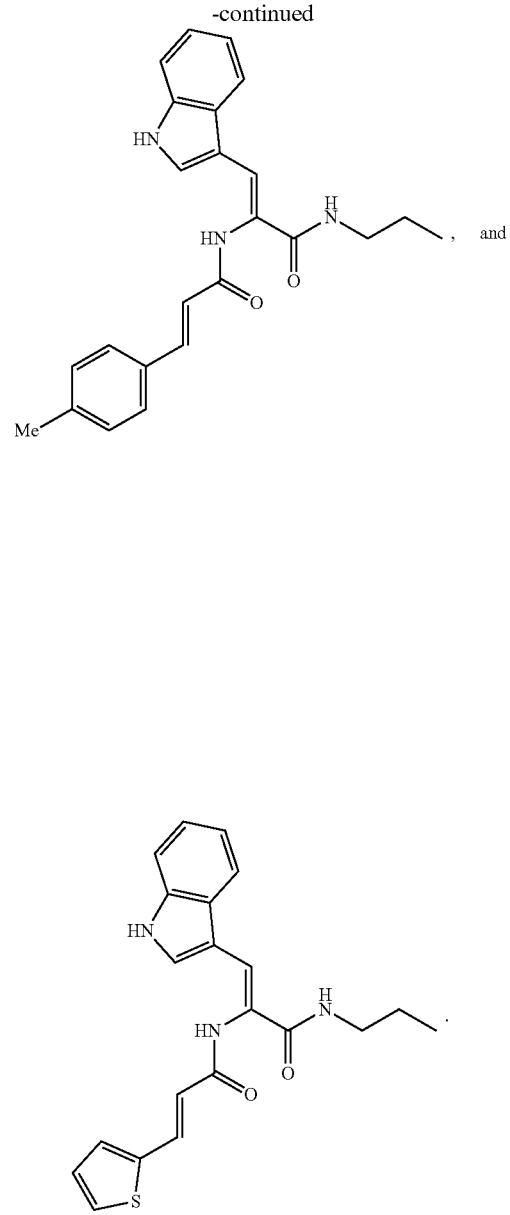
* * * * *